(12) United States Patent
Schlenker et al.

(10) Patent No.: US 12,723,191 B2
(45) Date of Patent: Sep. 1, 2026

(54) HEAVY-ATOM FREE SENSITIZERS FOR TRIPLET-TRIPLET ANNIHILATION UPCONVERSION SYSTEMS

(71) Applicant: University of Washington, Seattle, WA (US)

(72) Inventors: Cody Schlenker, Seattle, WA (US); Kathryn Corp, Seattle, WA (US); Sarah Pristash, Seattle, WA (US); Matthew Rigsby, Seattle, WA (US)

(73) Assignee: University of Washington, Seattle, WA (US)

( * ) Notice: Subject to any disclaimer, the term of this patent is extended or adjusted under 35 U.S.C. 154(b) by 795 days.

(21) Appl. No.: 18/245,860

(22) PCT Filed: Sep. 22, 2021

(86) PCT No.: PCT/US2021/051467

§ 371 (c)(1),
(2) Date: Mar. 17, 2023

(87) PCT Pub. No.: WO2022/093444

PCT Pub. Date: May 5, 2022

(65) Prior Publication Data

US 2023/0357630 A1 Nov. 9, 2023

Related U.S. Application Data

(60) Provisional application No. 63/083,499, filed on Sep. 25, 2020.

(51) Int. Cl.

| | |
|---|---|
| ***C09K 11/02*** | (2006.01) |
| ***C07C 323/65*** | (2006.01) |
| ***C09K 11/06*** | (2006.01) |

(52) U.S. Cl.

CPC ............ *C09K 11/02* (2013.01); *C07C 323/65* (2013.01); *C09K 11/06* (2013.01); *C09K 2211/1007* (2013.01); *C09K 2211/1011* (2013.01)

(58) Field of Classification Search

CPC . C09K 11/02; C09K 11/06; C09K 2211/1011; C09K 2211/1007; C07C 323/65

(Continued)

(56) References Cited

U.S. PATENT DOCUMENTS

| | | | |
|---|---|---|---|
| 2016/0237343 | A1 | 8/2016 | Baldo et al. |
| 2016/0351836 | A1 | 12/2016 | Forrest et al. |

(Continued)

FOREIGN PATENT DOCUMENTS

| | | | |
|---|---|---|---|
| CN | 107611281 | A | 1/2018 |
| JP | 2020111751 | | 7/2020 |

(Continued)

OTHER PUBLICATIONS

WO-2017154444-A1 English translation (Year: 2017).*

(Continued)

*Primary Examiner* — Anita Nassiri-Motlagh
(74) *Attorney, Agent, or Firm* — Christensen O'Connor Johnson Kindness PLLC

(57) ABSTRACT

The present disclosure features photon upconversion systems, including a sensitizer and an emitter, wherein the sensitizer absorbs an energy from an incident radiation, and the emitter accepts the energy from the sensitizer via triplet-triplet energy transfer, and emits at a lower wavelength than the incident radiation via a triplet-triplet annihilation process. The present disclosure also features devices including the photon upconversion systems.

19 Claims, 27 Drawing Sheets

(58) Field of Classification Search
USPC .................................................... 252/301.16
See application file for complete search history.

(56) References Cited

U.S. PATENT DOCUMENTS

| | | | |
|---|---|---|---|
| 2018/0311353 | A1 | 11/2018 | Kohane et al. |
| 2018/0314132 | A1 | 11/2018 | Bardeen |
| 2019/0085237 | A1 | 3/2019 | Miteva et al. |
| 2019/0275151 | A1 | 9/2019 | Campos et al. |
| 2020/0166502 | A1 | 5/2020 | Mai et al. |
| 2020/0295289 | A1 | 9/2020 | Lee et al. |
| 2021/0036249 | A1 | 2/2021 | Nienhaus et al. |

FOREIGN PATENT DOCUMENTS

| | | | |
|---|---|---|---|
| KR | 20160095953 | 8/2016 | |
| TW | 202019861 | 6/2020 | |
| TW | 202036952 A | 10/2020 | |
| WO | 2005047421 | 5/2005 | |
| WO | WO-2017154444 A1 * | 9/2017 | ............ H04N 25/70 |

OTHER PUBLICATIONS

Rosenberg, M., et al., "Excited State Aromaticity and Antiaromaticity: Opportunities for Photophysical and Photochemical Rationalizations," Chemical Reviews 114:5379-5425, 2014.
Roy, I., et al., "Photon Upconversion in a Glowing Metal-Organic Framework," Journal of the American Chemical Society 143(13):5053-5059, 2021.
Schulze, T.F., et al., "Efficiency Enhancement of Organic and Thin-Film Silicon Solar Cells with Photochemical Upconversion," The Journal of Physical Chemistry C 116:22794-22801, 2012.
Shockley, W., and H.J. Queisser, "Detailed Balance Limit of Efficiency of p-n Junction Solar Cells, Detailed Balance Limit of Efficiency of p-n Junction Solar Cells," Journal of Applied Physics 32(3):510-519, 1961.
Shokri, S., et al., "A Naphtho p quinodimethane Exhibiting Baird's (Anti)Aromaticity, Broken Symmetry, and Attractive Photoluminescence," The Journal of Organic Chemistry 82:10167-10173, 2017.
Shokri, S., et al., "Photon Upconversion Using Baird-Type (Anti)Aromatic Quinoidal Naphthalene Derivative as a Sensitizer," The Journal of Physical Chemistry C 121:23377-23382, 2017.
Sie, C.Z.W., and Z Ngaini, "Incorporation of Kojic Acid-Azo Dyes on TiO2 Thin Films for Dye Sensitized Solar Cells Applications," Hindawi Journal of Solar Energy vol. 2017, Article ID 2760301, 10 pages.
Simon, Y.C., and C. Weder, "Low-power photon upconversion through triplet-triplet annihilation in polymers," Journals of Materials Chemistry 22(39):20817-20830, 2012.
Singh-Rachford, T.N., et al., "Influence of Temperature on Low-Power Upconversion in Rubbery Polymer Blends," Journal of the American Chemical Society 131:12007-12014, 2009.
Singh-Rachford, T.N., and F.N. Castellano, "Low Power Visible-to-UV Upconversion," The Journal of Physical Chemistry A 113(20):5912-5917, 2009.
Singh-Rachford, T.N., and F.N. Castellano, "Pd(II) Phthalocyanine-Sensitized Triplet-Triplet Annihilation from Rubrene," The Journal of Physical Chemistry A 112:3550-3556, 2008.
Singh-Rachford, T.N., and F.N. Castellano, "Photon upconversion based on sensitized triplet-triplet annihilation," Coordination Chemistry Reviews 254:2560-2573, 2010.
Snellenburg, J.J., et al., "Glotaran: A Java-Based Graphical User Interface for the R Package TIMP," Journal of Statistical Software 49(3):1-22, Jun. 2012.
Song, Q., et al., "Organic Upconversion Display with an over 100% Photon-to-photon Upconversion Efficiency and a Simple Pixelless Device Structure," The Journal of Physical Chemistry Letters 9 (23):6818-6824, 2018.
Strassel, K., et al., "Shortwave infrared-absorbing squaraine dyes for all-organic optical upconversion devices," Science and Technology of Advanced Materials 22(1):194-204, 2021.
Strassel, K., et al., "Solution-Processed Organic Optical Upconversion Device," ACS Applied Materials & Interfaces 11 (26):23428-23435, 2019.
Strassel, K., et al., "Squaraine Dye for a Visibly Transparent All-Organic Optical Upconversion Device with Sensitivity at 1000 nm," ACS Applied Materials & Interfaces 10:11063-11069, 2018.
Taya, M., et al., "Overview on energy harvesting and storage systems (EHSS) for future AF vehicles," Proc. SPIE 6927, Electroactive Polymer Actuators and Devices (EAPAD) San Diego, California, Apr. 29, 2008, 9 pages.
Tilley, A.J., et al., "Ultrafast Triplet Formation in Thionated Perylene Diimides," Journal of Physical Chemistry C 118 (19):9996-10004, 2014.
Topel, S.D., et al., "Near IR excitation of heavy atom free Bodipy photosensitizers through the intermediacy of upconverting nanoparticles," 50:8896-8899, 2014.
Webster, S., et al., "Near-Unity Quantum Yields for Intersystem Crossing and Singlet Oxygen Generation in Polymethine-like Molecules: Design and Experimental Realization," The Journal of Physical Chemistry Letters 1:2354-2360, 2010.
Wei, D., et al., "A red thermally activated delayed fluorescence material as a triplet sensitizer for triplet-triplet annihilation up-conversion with high efficiency and low energy loss," The Journal of Materials Chemistry C 5:12374-12677, 2017.
Whited, M.T., et al., "Singlet and Triplet Excitation Management in a Bichromophoric Near-Infrared-Phosphorescent BODIPY-Benzoporphyrin Platinum Complex," Journal of the American Chemical Society 133(1):88-96, 2011.
Wu, W., et al., "Hetero Bodipy-dimers as heavy atom-free triplet photosensitizers showing a long-lived triplet excited state for triplet-triplet annihilation upconversion," Chemical Communications 49:9009-9011, 2013.
Wu, W., et al., "Organic Triplet Sensitizer Library Derived from a Single Chromophore (BODIPY) with Long-Lived Triplet Excited State for Triplet-Triplet Annihilation Based Upconversion," The Journal of Organic Chemistry 76:7056-7064, 2011.
Wang, X., et al. "Study of organic light-emitting diodes with exciplex and non-exciplex forming interfaces consisting of an ultrathin rubrene layer," Synthetic Metals 214:50-55, Apr. 2016.
Yanai, N., and N. Kimizuka, "New Triplet Sensitization Routes for Photon Upconversion: Thermally Activated Delayed Fluorescence Molecules, Inorganic Nanocrystals, and Singlet-to-Triplet Absorption," Accounts of Chemical Research 50:2487-2495, 2017.
Yum, J.-H., et al., "Efficient Far Red Sensitization of Nanocrystalline TiO2 Films by an Unsymmetrical Squaraine Dye," Journal of the American Chemical Society 129(34):10320-10321, 2007.
Zhang, D., et al., "Efficient and Stable Deep-Blue Fluorescent Organic Light-Emitting Diodes Employing a Sensitizer with Fast Triplet Upconversion," Advanced Materials vol. 32, Issue 19 (1908355), May 2020, 9 pages.
Zhao, J., et al., "Recent progress in heavy atom-free organic compounds showing unexpected intersystem crossing (ISC) ability," Organic Biomolecular Chemistry 16:3692-3701, 2018.
Zhou, N., et al., "Narrowband spectrally selective near-infrared photodetector based on up-conversion nanoparticles used in a 2D hybrid device," Journal of Materials Chemistry C 5(7):1591-1595, 2017.
International Search Report and Written Opinion mailed Jun. 3, 2022, issued in corresponding International Application No. PCT/US2021/51467 filed Sep. 22, 2021, 9 pages.
Cheng, Y.Y, et al., "On the efficiency limit of triplet-triplet annihilation for photochemical upconversion," Physical Chemistry Chemical Physics 12:66-71, 2010.
Duan, P., et al., "Photon Upconversion in Supramolecular Gel Matrices: Spontaneous Accumulation of Light-Harvesting Donor-Acceptor Arrays in Nanofibers and Acquired Air Stability," Journal of the American Chemical Society 137(5):1887-1894, Jan. 2015.
Tembo, M., "Enhancement of Photoconversion Efficiency of P3HT:PCBM Polymer Solar Cell Using Squarylium III Dye," Masters dissertation, University of Zambia, 2016, 72 pages.

(56) References Cited

OTHER PUBLICATIONS

Avlasevich, Y., et al., "Synthesis and applications of core-enlarged perylene dyes," Journal of Materials Chemistry 20:3814-3826, 2010.
Baird, N.C., "Quantum Organic Photochemistry. II. Resonance and Aromaticity in the Lowest 3TITT* State of Cyclic Hydrocarbons," Journal of the American Chemical Society 94(14):4941-4948, Jul. 1972.
Bharmoria, P., et al., "Triplet-triplet annihilation based near infrared to visible molecular photon upconversion," Chemical Society Reviews 49(18):6529-6792, Sep. 2020.
Cheng, Y.Y., et al., "Increased upconversion performance for thin film solar cells: a trimolecular composition," Chemical Science 7:559-568, 2016.
Corp, K.L., and C.W. Schlenker, "Ultrafast Spectroscopy Reveals Electron-Transfer Cascade That Improves Hydrogen Evolution with Carbon Nitride Photocatalysts," Journal of the American Chemical Society 139:7904-7912, 2017.
Cui, X., et al., "Zinc(II) tetraphenyltetrabenzoporphyrin complex as triplet photosensitizer for triplet-triplet annihilation upconversion," Chemical Communication 49(87):10195-10334, Nov. 2013.
Dou, Q., et al., "Bioimaging and biodetection assisted with TTA-UC materials," Drug Discovery Today 22 (9):1400-1411, Sep. 2017.
Duan, P., et al., "A bis-cyclometalated iridium complex as a benchmark sensitizer for efficient visible-to-UV photon upconversion," Chemical Communication 50:13111-13113, 2014.
Frazer, L., et al., "Optimizing the Efficiency of Solar Photon Upconversion," ACS Energy Letters 2:1346-1354, 2017.
Gholizadeh, E.M., et al., "Photochemical upconversion is suppressed by high concentrations of molecular sensitizers," Physical Chemistry Chemical Physics 20:19500-19506, 2018.
Gouterman, M., "Spectra of Porphyrins," Journal of Molecular Spectroscopy 6:138-163, 1961.
Gray, V., et al., "Triplet-triplet annihilation photon-upconversion: towards solar energy applications," Physical Chemistry Chemical Physics 16:10345-10652, 2014.
Ha, S.-J., et al., "Upconversion-Assisted Dual-Band Luminescent Solar Concentrator Coupled for High Power Conversion Efficiency Photovoltaic Systems," ACS Photonics 5:3621-3627, 2018.
Hagstrom, A.L., et al., "Flexible and Micropatternable Triplet-Triplet Annihilation Upconversion Thin Films for Photonic Device Integration and Anticounterfeiting Applications," ACS Applied Materials & Interfaces 10:8985-8992, 2018.
Islangulov, R.R., et al., "Noncoherent Low-Power Upconversion in Solid Polymer Films," Journal of the American Chemical Society 129:12652-12653, 2007.
Islangulov, R.R., and F.N. Castellano, Photochemical Upconversion: Anthracene Dimerization Sensitized to Visible Light by a Rull Chromophore, Angewandte Chemie Int. Ed. 45:5957-5959, 2006.
Ji, S., et al., "Ruthenium(II) Polyimine-Coumarin Dyad with Non-emissive 3IL Excited State as Sensitizer for Triplet-Triplet Annihilation Based Upconversion," Angewandte Chemie Int. Ed. 50:8283-8286, 2011.
Kanoh, M., et al., "Long-lived Triplet State Formation Caused by Intramolecular Energy Hopping in Diphenylanthracene Dyads Oriented to Undergo Efficient Triplet-Triplet Annihilation Upconversion," ChemRxiv, Oct. 2020, 7 pages.
Kashino, T., et al., "Bulk Transparent Photon Upconverting Films by Dispersing High-Concentration Ionic Emitters in Epoxy Resins," ACS Applied Materials & Interfaces 13(11):13676-13683, 2021.
Khnayzer. R.S., et al., "Upconversion-powered photoelectrochemistry" Chemical Communications 48:209-211, 2012.
Kim, J.-H., et al., "High Efficiency Low-Power Upconverting Soft Materials," Chemistry of Materials 24:2250-2252, 2012.
Kiseleva, N., et al., "Determination of Upconversion Quantum Yields Using Charge-Transfer State Fluorescence of Heavy-Atom-Free Sensitizer as a Self-Reference," The Journal of Physical Chemistry Letters 11(16):6560-6566, 2020.
Kiseleva, N., et al., "Lanthanide Sensitizers for Large Anti-Stokes Shift Near-Infrared to-Visible Triplet-Triplet Annihilation Photon Upconversion," Journal of Physical Chemistry Letters 11(7):2477-2481, 2020.
Law, K.-Y., "Squaraine Chemistry. Effects of Structural Changes on the Absorption and Multiple Fluorescence Emission of Bis[4-(dimethylamino)phenyl]squaraine and Its Derivatives," Journal of Physical Chemistry 91:5184-5193, 1987.
Li, C., et al., "Photocurrent Enhancement from Solid-State Triplet-Triplet Annihilation Upconversion of Low-Intensity, Low-Energy Photons," ACS Photonics 3:784-790, May 2016.
Liu, Q., et al., "Highly Photostable Near-IR-Excitation Upconversion Nanocapsules Based on Triplet-Triplet Annihilation for in Vivo Bioimaging Application," ACS Applied Materials & Interfaces 10:9883-9888, 2018.
Manna, M.K., et al., "New perspectives for triplet-triplet annihilation based photon upconversion using all-organic energy donor & acceptor chromophores," Chemical Communications 54:5809-5818, 2018.
McCusker, C.E., and F.N. Castellano, "Orange-to-blue and red-to-green photon upconversion with a broadband absorbing copper(I) MLCT sensitizer," Chemical Communications 49:3537-3539, 2013.
Monguzzi, A., et al., "Photocatalytic Water-Splitting Enhancement by Sub-Bandgap Photon Harvesting," ACS Applied Materials & Interfaces 9(46):40180-40186, 2017.
Monguzzi, A., et al., "Solid-State Sensitized Upconversion in Polyacrylate Elastomers," The Journal of Physical Chemistry C 120:2609-2614, 2016.
Niu, E., et al., "Fluorescence and Photochemistry of Dye Sensitizers in Nafion Membrane," Journal of Luminescence 40-41:563-564, 1988.
Oh, J., et al., "Spectroscopic Diagnosis of Excited-State Aromaticity: Capturing Electronic Structures and Conformations upon Aromaticity Reversal," Accounts of Chemical Research 51:1349-1358, 2018.
Oldenburg, M., et al., "Photon Upconversion at Crystalline Organic-Organic Heterojunctions," Advanced Materials 28(38):8477-8482, Oct. 2016.
Palmer, J.R., et al., "Visible-Light-Driven Triplet Sensitization of Polycyclic Aromatic Hydrocarbons Using Thionated Perinones," The Journal of Physical Chemistry Letters 11(13):5092-5099, 2020.
Peceli, D., et al., "Enhanced Intersystem Crossing Rate in Polymethine-Like Molecules: Sulfur-Containing Squaraines versus Oxygen-Containing Analogues," The Journal of Physical Chemistry A 117:2333-2346, 2013.
Peng, J., et al., "Developing efficient heavy-atom-free photosensitizers applicable to TTA upconversion in polymer films," Chemical Science 7:1233-1237, 2016.
Porter, G., and M.W. Windsor, "The triplet state in fluid media," Proceedings of the Royal Society of London. Series A 245:238-258, 1958.
Pristash, S.R., et al., "Heavy-Atom-Free Red-to-Yellow Photon Upconversion in a Thiosquaraine Composite," ACS Applied Energy Materials 3(1):19-28, 2020.
Qin, C., et al., "Novel Near-Infrared Squaraine Sensitizers for Stable and Efficient Dye-Sensitized Solar Cells," Advanced Functional Materials 24(20):3059-3066, 2014.
Qin, C., et al., "Squaraine Dyes for Dye-Sensitized Solar Cells: Recent Advances and Future Challenges," Chemistry—An Asian Journal 8(8):1706-1719, Aug. 2013.
Radiunas. E., et al., "Impact of t-butyl substitution in a rubrene emitter for solid state NIR-to-visible photon upconversion," Physical Chemistry Chemical Physics 22:7392-7403, 2020.
Radiunas, E., et al., "NIR-to-vis photon upconversion in rubrenes with increasing structural complexity," Journal of Materials Chemistry C 9(12):4359-4366, 2021.
Radiunas. E., et al., "Understanding the limitations of NIR-to-visible photon upconversion in phthalocyanine-sensitized rubrene systems," Journal of Materials Chemistry C 8:5525-5534, 2020.
Rao, G.H., et al., "Synthesis of Multichromophoric Asymmetrical Squaraine Sensitizer via C—H Arylation for See-through Photovoltaic," ACS Applied Energy Materials 1(9):4786-4793, 2018.

(56) References Cited

OTHER PUBLICATIONS

Rogers, J.E., et al., "Photophysical Characterization of a Series of Platinum(II)-Containing Phenyl-Ethynyl Oligomers," Journal of Physical Chemistry A 106:10108-10115, 2002.

Ronchi, A., et al., "High Photon Upconversion Efficiency with Hybrid Triplet Sensitizers by Ultrafast Hole-Routing in Electronic-Doped Nanocrystals," Advanced Materials vol. 32, Issue 37 (2002953), Sep. 2020, 7 pages.

* cited by examiner thiosquaraine rubrene

HEAVY-ATOM FREE SENSITIZERS FOR TRIPLET-TRIPLET ANNIHILATION UPCONVERSION SYSTEMS

CROSS-REFERENCES TO RELATED APPLICATIONS

This application is a National Stage of International Application No. PCT/US2021/051467, filed Sep. 22, 2021, which claims the benefit of U.S. Patent Application No. 63/083,499, filed Sep. 25, 2020, the disclosures of which are incorporated herein by reference in their entirety.

STATEMENT OF GOVERNMENT LICENSE RIGHTS

This invention was made with government support under Grant No. DGE-1256082, awarded by the National Science Foundation. The government has certain rights in the invention.

BACKGROUND

In the search for carbon-neutral renewable energy sources, solar photovoltaics remains the platform of greatest promise for meeting ever-increasing global demand. However, traditional solar cell efficiencies are inherently capped at the detailed balance limit outlined by Shockley and Queisser. This limit assumes that all incident sub-gap photons are transmitted, all above-gap photons generate carriers that thermalize to the semiconductor band edge, and all recombination losses occur radiatively. One potentially feasible strategy for possibly exceeding the Shockley-Queisser limit involves utilizing the sub-gap photons, which would otherwise be transmitted through the cell, by converting them into above-gap photons in a process known as photon upconversion. Photon upconversion can be achieved in a series of photophysical steps that generate high-energy photons through sequential absorption of multiple quanta of low energy light. Upconversion has attracted research interest in recent years for applications in photovoltaics, as well as photocatalysis, sensing and detection, and bioimaging.

Triplet-triplet annihilation (TTA) photon upconversion is a particularly attractive upconversion mechanism for light-harvesting applications due to its relatively low incident optical power requirements, i.e., it can be achieved with the non-coherent light from solar illumination. In the TTA upconversion mechanism, a sensitizer molecule absorbs a low-energy photon, which results in a singlet excitation on the chromophore, which subsequently undergoes intersystem crossing to form a triplet excited state. Triplet-triplet energy transfer (TTET) then occurs to an emitter molecule. Two emitter triplets can then annihilate via an overall spin-allowed electron exchange process to produce one emitter molecule in a singlet excited state and one emitter molecule in its singlet ground state. The singlet excited state radiatively relaxes, fluorescing at a higher energy than the incident absorbed photons. The wavelength of excitation and emission can thus be tuned by selecting an appropriate sensitizer/emitter combination.

Currently, the best TTA upconversion quantum efficiencies are achieved using transition metal or organometallic triplet sensitizers, wherein a heavy atom, typically a metal center, is required to induce large spin-orbit coupling constants. These organometallic complexes overwhelmingly rely on precious metals, such as Pt(II), Pd(II), Ir(III), or Ru(II). However, employing precious metals makes sensitizers costly, which may present a significant scalability barrier for widespread adoption in solar upconversion systems. This is particularly true if one contemplates utilizing a platinum sensitizer, for example, on the scale of hundreds of thousands of square kilometers. In many cases these complexes also rely on low-energy metal-to-ligand charge-transfer (MLCT) and porphyrin Q-band excitations with fairly weak extinction coefficients, which implies that excess material is required for maximum photon absorption at longer wavelengths. Finally, the influence of the heavy atom effect, in terms of its spin-orbit coupling interaction, has been observed to diminish with increasing conjugation length in precious metal complexes. Therefore, the efficiency of intersystem crossing is expected to diminish when extending the length of the chromophore's π-electron system to harvest sub-gap near-infrared (NIR) photons.

Considering the potential scalability challenges faced by light-harvesting upconversion systems that rely on precious metal centers, it is compelling to examine alternative molecular motifs. Organic sensitizers have the potential to be a comparatively lower-cost alternative to precious metal complexes, while maintaining facile synthesis and purification routes. Some success has been achieved in avoiding precious metals by using iodinated and brominated dyes, boron dipyrromethene, or "BODIPY," derivatives are some examples. However, introducing halogens as heavy-atom sensitizers carries the unintended consequence of decreasing the photostability of the sensitizer due to photolysis reactions associated with the arylhalide. For example, multiple iodo-BODIPY-derivatives have been shown to begin photobleaching over a period of a few hours of illumination. Despite this issue, there remain few examples of heavy atom-free organic upconversion sensitizers that avoid photoreactive halogens as a means of inducing intersystem crossing. There are reports of all-organic triplet sensitizers that operate through thermally activated delayed fluorescence, although these molecules typically have shorter triplet lifetimes that limit their energy transfer efficiencies. A handful of all-organic sensitizers exist that utilize nπ states to enhance intersystem crossing to closely-lying ππ triplet states, albeit usually with low extinction coefficients. The relationship between molecular structure and intersystem crossing efficiency for such all-organic chromophores comprises multiple factors, and it remains challenging to rationally design strongly-absorbing dyes that can act as efficient triplet sensitizers without incorporating heavy atoms.

Furthermore, stringent scalability and economic challenges persist in the face of emerging and established solar photovoltaic systems. New, potentially cost-effective, photon upconversion platforms, aimed at routinely meeting, or possibly exceeding, the Shockley-Queisser efficiency limit for the solar energy conversion efficiency of these systems are becoming increasingly compelling.

There is a need for triplet sensitizers that are free of heavy atoms that have high intersystem crossing efficiency and that are easily synthesized. The present disclosure fulfills these needs and provides further advantages.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a photon upconversion system, including: a photon upconversion system, comprising:

a sensitizer having a structure of Formula (I)

(I)

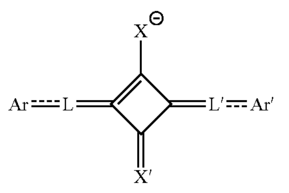

wherein:

X and X' are each independently selected from O, S, Se, and Te,

L is $(CRR')_n$, wherein:

R at each occurrence is independently H, halogen, $C_{1-10}$ alkyl, or $C_{1-10}$ haloalkyl, R' at each occurrence is absent, or independently H, halogen, $C_{1-10}$ alkyl, or $C_{1-10}$ haloalkyl, and n is an integer selected from 0, 1, 2, or 3;

L' is absent, or $(CR)_m$—$(CRR')_p$, wherein

R at each occurrence is independently H, halogen, $C_{1-10}$ alkyl, or $C_{1-10}$ haloalkyl, R' at each occurrence is absent, or independently H, halogen, $C_{1-10}$ alkyl, or $C_{1-10}$ haloalkyl, and m is 1; and p is an integer selected from 0, 1, or 2; and Ar and Ar' are each independently selected from aryl and heteroaryl, wherein said aryl and heteroaryl are each optionally substituted with 1, 2, 3, or 4 substituents independently selected from amino, $C_{1-10}$ alkyl, aryl, halo, OH, wherein each of said amino, $C_{1-10}$ alkyl, and aryl is optionally substituted with 1, 2, 3, or 4 substituents independently selected from amino, halo, $C_{1-10}$ alkyl, $C_{1-6}$ haloalkyl, and OH; wherein one of Ar and Ar' is positively charged; and an emitter, wherein the sensitizer absorbs an energy from an incident radiation, and the emitter accepts the energy from the sensitizer via triplet-triplet energy transfer, and emits at a lower wavelength than the incident radiation via a triplet-triplet annihilation process.

In another aspect, the present disclosure features a device, including the photon upconversion system described herein.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Definitions

Figure 1:
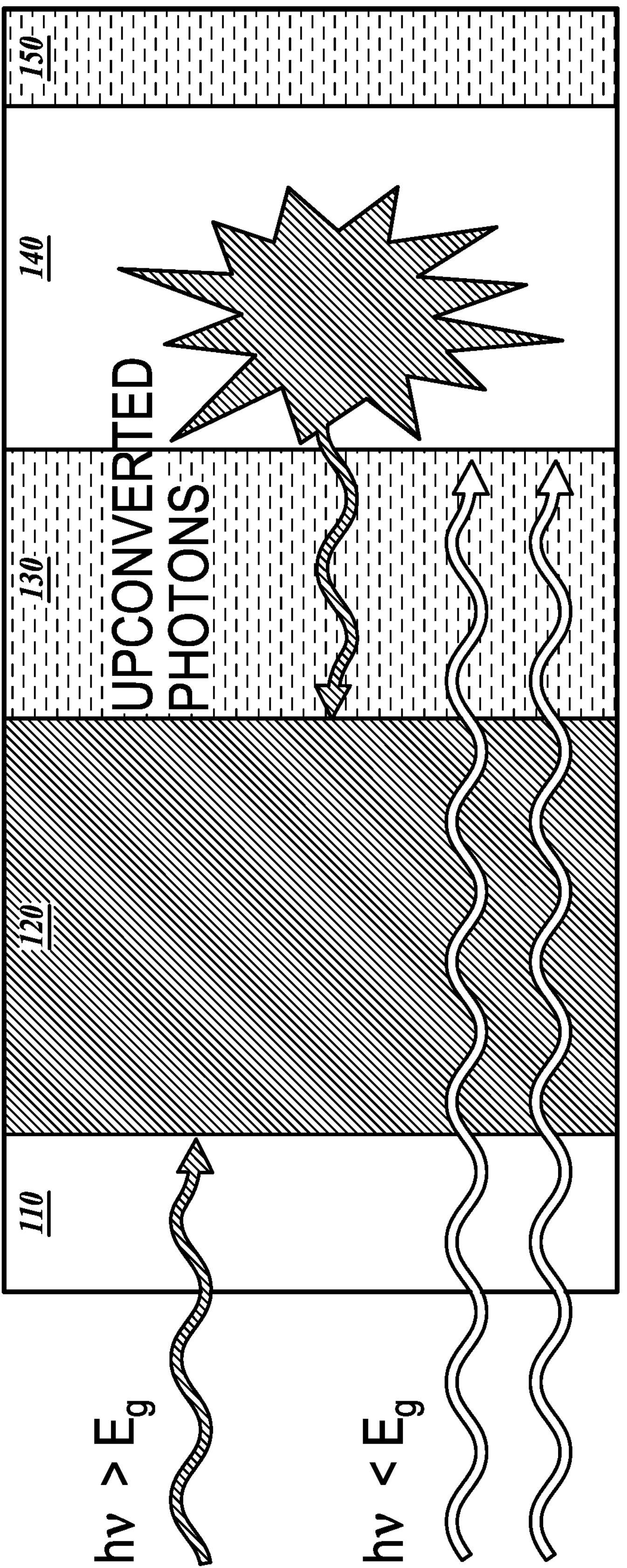
FIG. 1 is a schematic presentation of a photovoltaic device including an embodiment of the photon upconversion system of the present disclosure.

As used herein and unless otherwise indicated, the terms "a" and "an" are taken to mean "one", "at least one" or "one or more". Unless otherwise required by context, singular terms used herein shall include pluralities and plural terms shall include the singular.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. As an example, the term "optionally substituted with 1, 2, 3, 4, or 5" is intended to individually disclose optionally substituted with 1, 2, 3, 4, or 5; 1, 2, 3, or 4; 1, 2, or 3; 1 or 2; or 1 substituents.

It is further intended that the compounds of the disclosure are stable. As used herein "stable" refers to a compound that is sufficiently robust to survive isolation to a useful degree of purity from a reaction mixture.

It is further appreciated that certain features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

As used herein, the term "substituted" or "substitution" refers to the replacing of a hydrogen atom with a substituent other than H. For example, an "N-substituted piperidin-4-yl" refers to replacement of the H atom from the NH of the piperidinyl with a non-hydrogen substituent such as, for example, alkyl. The term "substituted" in reference to alkyl, alkylene, aryl, arylalkyl, alkoxy, heterocyclyl, heteroaryl, etc., for example, "substituted alkyl", "substituted alkylene", "substituted aryl", "substituted arylalkyl", "substituted heterocyclyl", and "substituted heteroaryl" means alkyl, alkylene, aryl, arylalkyl, heterocyclyl, heteroaryl respectively, in which one or more hydrogen atoms are each independently replaced with a non-hydrogen substituent. Typical substituents include, but are not limited to, alkyl, alkenyl, alkynyl, —Z, —R", —$O^-$, =O, —OR", —SR", —$S^-$, —$NR"_2$, —$N^+R"_3$, =NR", —$CZ_3$, —CN, —OCN, —SCN, —N=C=O, —NCS, —NO, —$NO_2$, =$N_2$, —$N_3$, —NHC(=O)R", —OC(=O)R", —NHC(=O)$NR"_2$, —S(=O)$_2$—, —S(=O)$_2$OH, —S(=O)$_2$R", —OS(=O)$_2$OR", —S(=O)$_2$$NR"_2$, —S(=O)R", —OP(=O)(OR")$_2$, —P(=O)(OR")$_2$, —P(=O)($O^-$)$_2$, —P(=O)(OH)$_2$, —P(O)(OR")($O^-$), —C(=O)R", —C(=O)Z, —C(S)R", —C(O)OR", —C(O)$O^-$, —C(S)OR", —C(O)SR", —C(S)SR", —C(O)$NR"_2$, —C(S)$NR"_2$, —C(=NR")$NR"_2$, where each Z is independently a halogen: F, Cl, Br, or I; and each R" is independently H, alkyl, aryl, arylalkyl, a heterocycle, or a protecting group. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

"Optionally substituted" groups can refer to, for example, functional groups that may be substituted or unsubstituted by additional functional groups. For example, when a group is unsubstituted, it can be referred to as the group name, for example alkyl or aryl. When a group is substituted with additional functional groups, it may more generically be referred to as substituted alkyl or substituted aryl.

Where a numerical range is disclosed herein, then such a range is continuous, inclusive of both the minimum and maximum values of the range, as well as every value between such minimum and maximum values. Still further, where a range refers to integers, every integer between the minimum and maximum values of such range is included. In addition, where multiple ranges are provided to describe a feature or characteristic, such ranges can be combined. That is to say that, unless otherwise indicated, all ranges disclosed herein are to be understood to encompass any and all subranges subsumed therein. For example, a stated range of from "1 to 10" should be considered to include 1 and 10, and any and all subranges between the minimum value of 1 and the maximum value of 10. Exemplary subranges of the range "1 to 10" include, but are not limited to, e.g., 1 to 6.1, 3.5 to 7.8, and 5.5 to 10.

It is intended that divalent groups, such as linking groups (e.g., alkylene, arylene, etc.) between a first and a second moieties, can be oriented in both forward and the reverse direction with respect to the first and second moieties, unless specifically described.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$ alkoxycarbonyloxy and —OC(O)$C_1$-$C_6$ alkyl indicate the same functionality; similarly arylalkyl and -alkylaryl indicate the same functionality.

As used herein, the term "alkyl" refers to a straight or branched chain saturated hydrocarbon containing from 1 to 24 carbon atoms, unless otherwise specified. Representative examples of alkyl include, but are not limited to, methyl (Me), ethyl (Et), propyl (e.g., n-propyl, iso-propyl), butyl (e.g., n-butyl, sec-butyl, iso-butyl, tert-butyl), pentyl (n-pentyl, isopentyl, neopentyl), n-hexyl, 3-methylhexyl, 2,2-dimethylpentyl, 2,3-dimethylpentyl, n-heptyl, n-octyl, n-nonyl, and n-decyl. In some embodiments, alkyl contains 1 to 20 carbon atoms, 1 to 16 carbon atoms, 1 to 12 carbon atoms, 1 to 8 carbon atoms, or 1 to 6 carbon atoms.

As used herein, the term "alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 16 carbon atoms, 1 to 12 carbon atoms, 1 to 10 carbon atoms, 1 to 8 carbon atoms, or 1 to 6 carbon atoms. Typical alkylene radicals include, but are not limited to, methylene ($—CH_2—$), 1,1-ethyl ($—CH(CH_3)—$), 1,2-ethyl ($—CH_2CH_2—$), 1,1-propyl ($—CH(CH_2CH_3)—$), 1,2-propyl ($—CH_2CH(CH_3)—$), 1,3-propyl ($—CH_2CH_2CH_2—$), 1,4-butyl ($—CH_2CH_2CH_2CH_2—$), and the like.

As used herein, the term "alkenyl" refers to a straight or branched chain hydrocarbon containing from 2 to 24 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl. In some embodiments, alkenyl contains 2 to 20 carbon atoms, 2 to 16 carbon atoms, 2 to 12 carbon atoms, 2 to 8 carbon atoms, or 2 to 6 carbon atoms.

As used herein, the term "alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 2 to 20 carbon atoms, 2 to 16 carbon atoms, 2 to 12 carbon atoms, 2 to 8 carbon atoms, or 2 to 6 carbon atoms. Typical alkenylene radicals include, but are not limited to, 1,2-ethylene ($—CH{=}CH—$).

As used herein, the term "alkynyl" refers to a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl. In some embodiments, alkynyl contains 2 to 20 carbon atoms, 2 to 16 carbon atoms, 2 to 12 carbon atoms, 2 to 8 carbon atoms, or 2 to 6 carbon atoms.

As used herein, the term "alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 2 to 20 carbon atoms, 2 to 16 carbon atoms, 2 to 12 carbon atoms, 2 to 8 carbon atoms, or 2 to 6 carbon atoms. Typical alkynylene radicals include, but are not limited to, acetylene ($—C{\equiv}C—$), propargyl ($—CH_2C{\equiv}C—$), and 4-pentynyl ($—CH_2CH_2CH_2C{\equiv}C—$).

As used herein, the term "amino" refers generally to a nitrogen radical which can be considered a derivative of ammonia, having the formula $—N(Y)_2$, where each "Y" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include $—NH_2$, $—N(alkyl)_2$, —NH(alkyl), $—N(carbocyclyl)_2$, —NH(carbocyclyl), $—N(heterocyclyl)_2$, —NH(heterocyclyl), $—N(aryl)_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with one alkyl group. The term "dialkylamino" refers to an amino group substituted with two alkyl groups. Nonlimiting examples of amino groups include $—NH_2$, $—NH(CH_3)$, $—N(CH_3)_2$, $—NH(CH_2CH_3)$, $—N(CH_2CH_3)_2$, —NH(phenyl), $—N(phenyl)_2$, —NH(benzyl), $—N(benzyl)_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), $—N(alkylene-C(O)—OH)_2$, $—N(alkylene-C(O)—O-alkyl)_2$, etc.

As used herein, the term "aryl" refers to monocyclic or polycyclic (e.g., having 2, 3 or 4 fused rings) aromatic hydrocarbon radical derived by the removal of one hydrogen atom from a single carbon atom of a parent aromatic ring system. For example, an aryl group can include example, phenyl, naphthyl, anthracenyl, phenanthrenyl, indanyl, indenyl, and the like. In some embodiments, aryl groups have from 6 to about 20 carbon atoms, 6 to 14 carbon atoms, or 6 to 10 carbon atoms.

As used herein, the term "arylene" refers to a linking aryl group.

As used herein, the term "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as spiro ring systems. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like.

As used herein, the term "cycloalkylene" refers to a linking cycloalkyl group.

As used herein, the term "heteroalkyl" refers to an alkyl group having at least one heteroatom such as sulfur, oxygen, or nitrogen. For example, if the carbon atom of the alkyl group which is attached to the parent molecule is replaced with a heteroatom (e.g., O, N, or S) the resulting heteroalkyl groups are, respectively, an alkoxy group (e.g., $—OCH_3$, etc.), an amine (e.g., $—NHCH_3$, $—N(CH_3)_2$, etc.), or a thioalkyl group (e.g., $—SCH_3$). If a non-terminal carbon atom of the alkyl group which is not attached to the parent molecule is replaced with a heteroatom (e.g., O, N, or S) the resulting heteroalkyl groups are, respectively, an alkyl ether (e.g., $—CH_2CH_2—O—CH_3$, etc.), an alkyl amine (e.g., $—CH_2NHCH_3$, $—CH_2N(CH_3)_2$, etc.), or a thioalkyl ether (e.g., $—CH_2—S—CH_3$). If a terminal carbon atom of the alkyl group is replaced with a heteroatom (e.g., O, N, or S), the resulting heteroalkyl groups are, respectively, a hydroxyalkyl group (e.g., $—CH_2CH_2—OH$), an aminoalkyl group (e.g., $—CH_2NH_2$), or an alkyl thiol group (e.g., $—CH_2CH_2—SH$). A heteroalkyl group can have, for example, 1 to 20 carbon atoms, 1 to carbon atoms, or 1 to 6 carbon atoms. A $C_1$-$C_6$ heteroalkyl group means a heteroalkyl group having 1 to 6 carbon atoms.

As used herein, the term "heteroalkylene" refers to a linking heteroalkyl group.

As used herein, the term "heteroaryl" refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, acridinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, the term "heteroarylene" refers to a linking heteroaryl group.

As used herein, the term "alkoxy" refers to an —O-alkyl group. Example alkoxy groups include methoxy, ethoxy, propoxy (e.g., n-propoxy and isopropoxy), t-butoxy, and the like.

As used herein, the term "cycloalkoxy" refers to an —O-cycloalkyl group.

As used herein, the term "heterocycloalkoxy" refers to an —O-heterocycloalkyl group.

As used herein, the term "aryloxy" refers to an —O-aryl group. Example aryloxy groups include phenyl-O—, substituted phenyl-O—, and the like.

As used herein, the term "heteroaryloxy" refers to an —O-heteroaryl group.

As used herein, the term "arylalkyl" refers to alkyl substituted by aryl and "cycloalkylalkyl" refers to alkyl substituted by cycloalkyl. An example arylalkyl group is benzyl.

As used herein, the term "heteroarylalkyl" refers to alkyl substituted by heteroaryl and "heterocycloalkylalkyl" refers to alkyl substituted by heterocycloalkyl.

As used herein, the term "halo" or "halogen" includes fluoro, chloro, bromo, and iodo.

As used herein, the term "anionic" refers to a functional group that is negatively charged, or ionizable to a negatively charged moiety under physiological conditions. Examples of anionic groups include carboxylate, sulfate, sulfonate, phosphate, etc.

As used herein, the term "cationic" refers to a moiety that is positively charged, or ionizable to a positively charged moiety under physiological conditions. Examples of cationic moieties include, for example, amino, ammonium, pyridinium, imino, sulfonium, quaternary phosphonium groups, etc.

As used herein, an "electron donating substituent" refers to a substituent that adds electron density to an adjacent pi ($\pi$)-system, making the $\pi$-system more nucleophilic. In some embodiments, an electron donating substituent has lone pair electrons on the atom adjacent to $\pi$-system. In some embodiments, electron donating substituents have $\pi$-electrons, which can donate electron density to the adjacent pi-system via hyperconjugation. Examples of electron donating substituents include O—, $NR_2$, $NH_2$, OH, OR, NHC(O)R, OC(O)R, aryl, and vinyl substituents.

As used herein, the term "unsaturated bond" refers to a carbon-carbon double bond or a carbon-carbon triple bond.

As used herein, the term "protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are described, for example, in "Protective Groups in Organic Chemistry," Theodora W. Greene (John Wiley & Sons, Inc., New York, 1991. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. "Hydroxy protecting groups" refers to those protecting groups useful for protecting hydroxy groups (—OH).

As used herein, "forming a reaction mixture" refers to the process of bringing into contact at least two distinct species such that they mix together and can react. It should be appreciated, however, the resulting reaction product can be produced directly from a reaction between the added reagents or from an intermediate from one or more of the added reagents which can be produced in the reaction mixture.

As used herein, a "leaving group" refers to groups that maintain the bonding electron pair during heterolytic bond cleavage. For example, a leaving group is readily displaced during a nucleophilic displacement reaction. Suitable leaving groups include, but are not limited to, chloride, bromide, mesylate, tosylate, triflate, 4-nitrobenzenesulfonate, 4-chlorobenzenesulfonate, 4-nitrophenoxy, pentafluorophenoxy, etc. One of skill in the art will recognize other leaving groups useful in the present invention.

As used herein, a "deprotection agent" refers to any agent capable of removing a protecting group. The deprotection agent will depend on the type of protecting group used. Representative deprotection agents are known in the art and can be found in Protective Groups in Organic Chemistry, Peter G. M. Wuts and Theodora W. Greene, 4th Ed., 2006.

Unless defined otherwise, any feature within any aspect or embodiment of the disclosure may be combined with any feature within any other aspect or embodiment of the invention, and such combination are encompassed in the present disclosure. This also applies, but not exclusively, to endpoints of ranges disclosed herein. For instance, if a given substance is disclosed as existing in a composition in a concentration range of X-Y % or A-B %, the present disclosure is to be understood as explicitly disclosing not only the ranges X-Y % and A-B %, but also the ranges X-B %, A-Y % and, in as far as numerically possible, Y-A % and B-X %. Each of these ranges, and range combinations, are contemplated, and are to be understood as being directly and unambiguously disclosed in the present application.

Unless stated otherwise, the designation of a range in the present application using a hyphen ("-") separating two bracketing values X and Y, or two bracketing ratios, is to be understood as meaning and disclosing the specified range in which both endpoint values X and Y are included. The same applies to a range expressed as "from X to Y". Accordingly, the expressions of ranges as "X-Y", "of X to Y", "from X to Y", "of X-Y" and "from X-Y" are to be understood equivalently as meaning and disclosing a range encompassing the end value X, all values (including decimals) between X and Y, as well as the end value Y.

As used herein the term "about" when referring to a particular value, e.g., an endpoint or endpoints of a range, encompasses and discloses, in addition to the specifically recited value itself, a certain variation around that specifically recited value. Such a variation may for example arise from normal measurement variability, e.g., in the weighing or apportioning of various substances by methods known to the skilled person. The term "about" shall be understood as encompassing and disclosing a range of variability above and below an indicated specific value, said percentage values being relative to the specific recited value itself, as follows: The term "about" may encompass and disclose variability of ±5.0%. The term "about" may encompass and disclose variability of ±4.5%. The term "about" may encompass and disclose variability of ±4.0%. The term "about" may encompass and disclose variability of ±3.5%. The term "about" may encompass and disclose variability of ±3.0%. The term "about" may encompass and disclose variability of ±2.5%. The term "about" may encompass and disclose variability of ±2.0%. The term "about" may encompass and disclose variability of ±1.5%. The term "about" may encompass and disclose variability of ±1.0%. The term "about" may encompass and disclose variability of ±0.5%. The term "about", in reference to the particular recited value, may encompass and disclose that exact particular value itself, irrespective of any explicit mention that this exact particular value is included; even in the absence of an explicit indication that the term "about" includes the particular exact recited value, this exact particular value is still included in the range of variation created by the term "about", and is therefore disclosed in the present application. Unless stated otherwise, where the term "about" is recited before the first endpoint of a numerical range, but not before the second endpoint of that range, this term, and the variability it implies in scope and disclosure, refers to both the first endpoint of the range and the second endpoint of the range. For instance, a recited range of "about X to Y" should be read as "about X to about Y". The same applies for a recited range of ratios. For instance, a recited range of weight ratios of "about X:Y-A:B" should be read as a weight ratio of "(about X):(about Y)-(about A):(about B)".

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

It will be readily understood that the aspects of the present disclosure, as generally described herein, and illustrated in the figures, can be arranged, substituted, combined, separated, and designed in a wide variety of different configurations, all of which are explicitly contemplated herein.

Furthermore, the particular arrangements shown in the FIGURES should not be viewed as limiting. It should be understood that other embodiments may include more or less of each element shown in a given FIGURE. Further, some of the illustrated elements may be combined or omitted. Yet further, an example embodiment may include elements that are not illustrated in the FIGURES.

Photon Upconversion Systems

The present disclosure features a photon upconversion system, including:

a sensitizer having a structure of Formula (I)

(I)

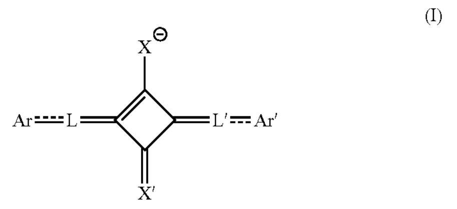

wherein:

X and X' are each independently selected from O, S, Se, and Te,

L is $(CRR')_n$, wherein:

R at each occurrence is independently H, halogen, $C_{1-10}$ alkyl, or $C_{1-10}$ haloalkyl, R' at each occurrence is absent, or independently H, halogen, $C_{1-10}$ alkyl, or $C_{1-10}$ haloalkyl, and n is an integer selected from 0 (in which case L is absent and Ar is directly conjugated to the cyclobutene via a single bond), 1, 2, or 3;

L' is absent (in which case Ar' is directed conjugated to the cyclobutene via a double bond), or $(CR)_m$—$(CRR')_p$ (where the direction of $(CR)_m$—$(CRR')_p$ is left to right in the structure of Formula (I)), wherein R at each occurrence is independently H, halogen, $C_{1-10}$ alkyl, or $C_{1-10}$ haloalkyl, R' at each occurrence is absent, or independently H, halogen, $C_{1-10}$ alkyl, or $C_{1-10}$ haloalkyl, and m is 1; and p is an integer selected from 0, 1, or 2; and Ar and Ar' are each independently selected from aryl and heteroaryl, wherein said aryl and heteroaryl are each optionally substituted with 1, 2, 3, or 4 substituents independently selected from amino, $C_{1-10}$ alkyl, aryl, halo, OH, wherein each of said amino, $C_{1-10}$ alkyl, and aryl is optionally substituted with 1, 2, 3, or 4 substituents independently selected from amino, halo, $C_{1-10}$ alkyl, $C_{1-6}$ haloalkyl, and OH; wherein one of Ar and Ar' is positively charged; and an emitter, wherein the sensitizer absorbs an energy from an incident radiation, and the emitter accepts the energy from the sensitizer via triplet-triplet energy transfer, and emits at a lower wavelength than the incident radiation via a triplet-triplet annihilation process.

The structure of Formula (I) can be free of carboxylic acid substituents, ester substituents, and/or cyano substituents, In some embodiments, the sensitizer of Formula (I) does not include any heavy atoms. In some embodiments, the photon upconversion system does not include any heavy atoms. As used herein, a "heavy atom" refers to elements having an atomic number of greater than 18, excluding where X and X' are each independently Te or Se.

In some embodiments, the sensitizer of Formula (I) does not include any metals. In some embodiments, the photon upconversion system does not include any metal atoms. As used herein, a "metal atom" refers to elements having atomic numbers of 3, 4, 11-13, 19-32, 27-51, 55-84, and 87-116 (atomic numbering system adopted by the International Union of Pure and Applied Chemistry).

In some embodiments, the sensitizer of Formula (I) does not include halogen atoms. In certain embodiments, the photon upconversion system does not include halogen atoms.

The emitter can have a triplet energy level within at least about 0.13 eV, at room temperature, of a triplet energy level of the sensitizer. In some embodiments, the emitter has a triplet energy level within at least about 5 kT of a triplet energy level of the sensitizer. The emitter can have a triplet energy level within at least about 0.13 eV higher than, at room temperature, a triplet energy level of the sensitizer. In some embodiments, the emitter has a triplet energy level higher by at least about 5 kT of a triplet energy level of the sensitizer.

In some embodiments, the sensitizer can have a narrow absorption spectrum. For example, the sensitizer can have a full width at half maximum absorption of 40 nm or less (e.g., 35 nm or less, 30 nm or less, 25 nm or less, 20 nm or less, or 15 nm or less). In some embodiments, the sensitizer has a full width at half maximum absorption of from 10 nm (e.g., from 15 nm, from 20 nm, from 25 nm, from 30 nm, or from 35 nm) to 40 nm (e.g., to 35 nm, to 30 nm, to 25 nm, to 20 nm, or to 15 nm).

The sensitizer can have little overlapping absorption with the absorption spectrum of the emitter, such that the sensitizer absorbs a different portion of incident radiation relative to the emitter's absorption. Therefore, a larger proportion of the incident radiation can be used in a device that includes the photon upconversion system. For example, in some embodiments, the sensitizer absorbs less than 10% (e.g., less than 8%, less than 5%, less than 3%) of the emitter's absorption spectrum (i.e., the overlap of the sensitizer's absorption spectrum with the absorption spectrum of the emitter is less than 10% (e.g., less than 8%, less than 5%, less than 3%) of the emitter's absorptions spectrum).

The incident radiation can be non-coherent (e.g., non-layer radiation) or coherent. For example, the incident radiation can be sunlight, a lamp source, a heat source, and can include, for example, ultraviolet, visible, and/or infrared radiations. In some embodiments, the incident radiation is coherent and can range from 10 nm to 1 mm in wavelength.

The triplet-triplet energy transfer process of the photon upconversion system can proceed via a bimolecular Dexter energy transfer process.

The photon upconversion system can have an anti-Stokes shift of 0.1 eV or more (e.g., 0.2 eV or more, 0.3 eV or more, 0.4 eV or more, or 0.5 eV or more). In some embodiments, the photon upconversion system has a triplet-triplet upconversion quantum efficiency of more than 0% (e.g., more than 5%, more than 10%, more than 15%, more than 20%, more than 25%, more than 30%, more than 40%, or more than 45%) and/or less than or equal to 50% (e.g., less than 45%, less than 40%, less than 35%, less than 30%, less than 25%, less than 20%, less than 15%, less than 10%, or less than 5%).

In some embodiments, L is $(CRR')_n$ in Formula (I), and R at each occurrence is independently H or $C_{1-10}$ alkyl; R' at each occurrence is absent (if the carbon to which R is connected to has a double bond, i.e., —C(R)═), or independently H or $C_{1-10}$ alkyl; and n is an integer selected from 0 and 1. In some embodiments, n is 0.

In some embodiments, L' is absent, or $(CR)_m$—$(CRR')_p$, wherein R at each occurrence is independently H or $C_{1-10}$ alkyl; R' at each occurrence is absent (if the carbon to which R is connected to has a double bond), or independently H or $C_{1-10}$ alkyl; m is 1; and p is an integer selected from 0 and 1. In some embodiments, p is 0.

In some embodiments, Ar and Ar' in Formula (I) are each independently selected from aryl and heteroaryl, wherein said aryl and heteroaryl are each optionally substituted with 1, 2, 3, or 4 substituents independently selected from $C_{1-10}$ alkyl, a primary amino, $C_{1-10}$ alkylamino, and a di($C_{1-10}$ alkyl)amino. In some embodiments, Ar and Ar' are each independently selected from benzil, anthracyl, pyrenyl, azulenyl, pyridinyl, imidazolyl, carbazolyl, pyrrolyl, thiophenyl, quinolinyl, indolyl, benzindolyl, acridinyl, thiazolyl, benzothiazolyl, selenazolyl, and benzoselenazolyl, each optionally substituted with 1, 2, 3, or 4 substituents independently selected from amino, $C_{1-10}$ alkyl, aryl, halo, OH, wherein each of said amino, alkyl, and aryl is optionally substituted with 1, 2, 3, or 4 substituents independently selected from amino, halo, and OH. In some embodiments, when Ar and/or Ar' is heteroaryl, the heteroaryl can contain at least one nitrogen atom in the heteroaryl ring system, and the nitrogen atom is substituted with 1 or 2 $C_{1-10}$ alkyl groups. In some embodiments, one of Ar and Ar' is aryl substituted with $N(C_{1-10}\ alkyl)_2$, and the remaining Ar or Ar' is an aryl substituted with $=N^+(C_{1-10}\ alkyl)_2$, such that one of Ar or Ar' is positively charged. In some embodiments, Ar and/or Ar' is heteroaryl containing a nitrogen atom in the heteroaryl ring, wherein one of Ar or Ar' contains a nitrogen atom substituted with $C_{1-10}$ alkyl, and the remaining Ar or Ar' contains a positively charged nitrogen atom substituted with 2 $C_{1-10}$ alkyl groups, such that one of Ar or Ar' is positively charged.

In some embodiments, the sensitizer is selected from:

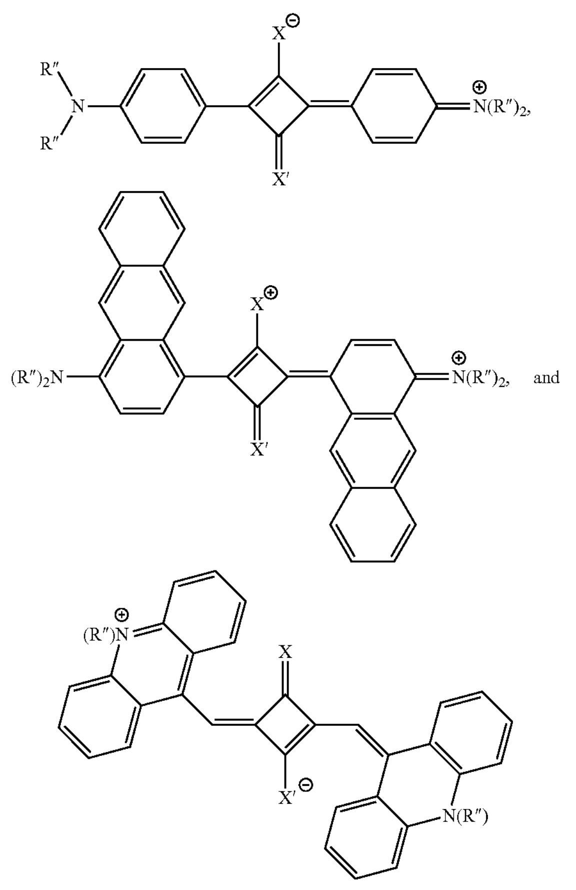

wherein R" at each occurrence is independently $C_{1-10}$ alkyl; and

X and X' are each independently selected from S and O.

In some embodiments, X and X' are each S.

In any of the above-mentioned embodiments, the sensitizer can have a delocalized electronic structure, such that the electron density on the double bonds can be delocalized throughout the electronically conjugated structure of Formula (I). One of Ar and Ar' can positively charged in any given resonance structure representation. Thus, the sensitizer of the present disclosure can have a symmetric structure. In some embodiments, the sensitizer has C2-symmetry. In some embodiment, the C2-symmetry axis bisects the X and X' substituents, as well as the carbon atoms to which the X and X' are attached to, in the cyclobutene core. Without wishing to be bound by theory, it is understood that one resonance structure of the sensitizer is shown in the chemical structures above, but that the sensitizer has delocalized electrons such that the sensitizer is symmetric (e.g., C2-symmetric).

In some embodiments, the emitter of the photon upconversion system is selected from rubrene, TiPS-anthracene, 1-chloro-9,10-bis(phenylethynyl)anthracene, 2-chloro-9,10-bis(phenylethynyl)anthracene, and violanthrone-79. The emitter can be devoid of boron-containing compounds. For example, the emitter can be devoid of BODIPY and its derivatives.

The sensitizers of the present disclosure can be readily synthesized by a person of ordinary skill in the art. For example, referring to Scheme 1, amino-aryl- or amino-containing heteroaryl-substituted squaraines can be synthesized by heating a mixture of an amino-substituted aryl or amino-containing heteroaryl with squaric acid in a solvent or solvent system. The resulting squaraine product has a positive charge on one of the amino-aryl or amino-containing heteroaryl substituents. Similarly, referring to Scheme 2, a mixture of methylated amino-substituted aryl or amino-containing heteroaryl with squaric acid can be heated in a solvent or solvent system to provide a squaraine substituted with amino-aryl or an amino-containing heteroaryl via an alkylenyl group, The resulting squaraine product has a positive charge on one of the amino-aryl or amino-containing heteroaryl substituents. The solvent or solvent system can be suitable to removal of water, for example, by distillation. In some embodiments, the solvent includes n-butanol, toluene, xylene, benzene, or any combination thereof. In some embodiments, the solvent is a mixture of n-butanol and toluene. The mixture of amino-substituted aryl or amino-containing heteroaryl with squaric acid can be heated at a temperature of 60° C. or more to 150 or less. In some embodiments, the mixture of amino-substituted aryl or amino-containing heteroaryl with squaric acid in the solvent or solvent system is heated at a reflux temperature of the solvent or solvent system. In some embodiments, the reaction is carried out under inert atmosphere (e.g., nitrogen, argon). In some embodiments, the reaction is carried out in air.

Scheme 1. Synthesis of directly attached aryl/heteroaryl-substituted squaraines.

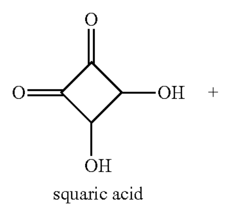

squaric acid

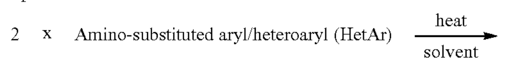

-continued

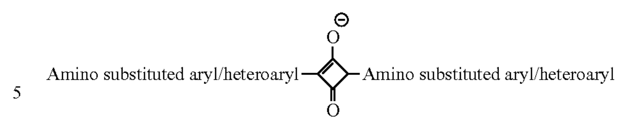

one amino group of one of aryl/heteroaryl is positively charged

Scheme 2. Synthesis of squaraines having aryl/heteroaryl substitutes connected to squaraine via an alkenylene.

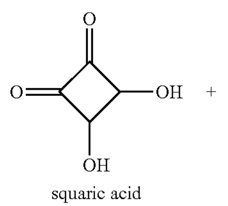

squaric acid

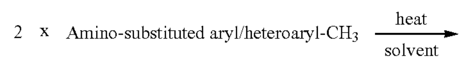

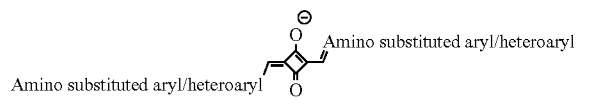

The substituted squaraines can be converted to thiosquaraines and selenosquaraines using Lawesson's reagent and its selenium analog (Woollins' reagent"). Without wishing to be bound by theory, it is believed that tellurium squaraine derivatives can be synthesized using the tellurium analog of Lawesson's reagent. s Scheme 3. Conversion of squaraines to thiosquaraines.

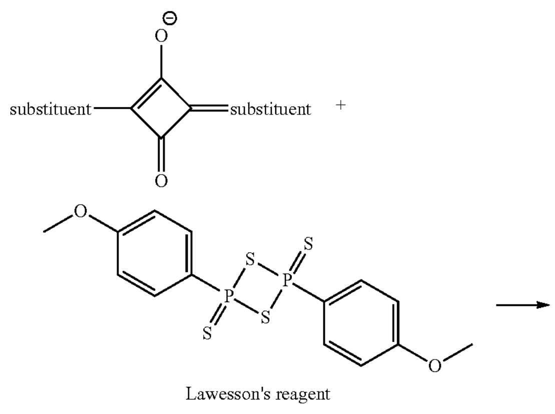

Lawesson's reagent

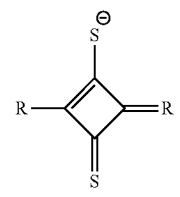

Scheme 4. Conversion of squaraine to selenosquaraine.

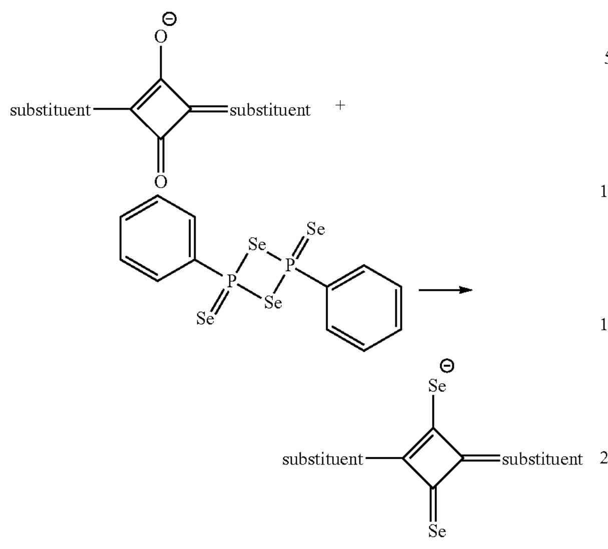

The synthesis of squaraines is described, for example, in Hu et al., Advances in Synthesis and Application of Near-Infrared Absorbing Squaraine Dyes, RSC Adv., 2013, 3, 7667-7676; and K. Y. Law and F. C. Bailey, Squaraine, Characterization, and Optical Properties of a Class of Novel Unsymmetrical Squaraines: [4-(Dimethylamino)phenyl](4'-methoxyphenyl)squaraine and its Derivatives, *J. Org. Chem.* 1992, 57, 12, 3278-3286; incorporated herein by reference in its entirety. The use of Lawesson's reagent is described, for example, in Ozturk et al., Use of Lawesson's Reagent in Organic Synthesis, Chem. Rev. 2007, 107, 5210-5278, incorporated herein by reference in its entirety.

Devices

The photon upconversion system described herein can be incorporated into devices. In some embodiments, the device is a photovoltaic device, a solar luminescent concentrator, a photocatalytic device, a sensor, a bioimaging material, or an anti-counterfeit system. In some embodiments, the photon upconversion system can be used for bioimaging. Flexible and micropatternable triplet-triplet annihilation upconversion thin films for photonic device integration and anticounterfeiting applications are described, for example, in Hagstrom, A. L., et. al. *ACS Applied Materials and Interfaces,* 10(10), 8985-8992, incorporated herein by reference in its entirety. In some embodiments, the excitation and emission wavelengths can be greater than 600 nm, such that it is in the transparent window for biological tissue, and the photon upconversion system can be used in in vivo imaging. Bioimaging applications and techniques are described, for example, in Liu, Q. et al., *ACS Applied Materials and Interfaces,* 10(12), 9883-9888, incorporated herein by reference in its entirety.

In some embodiments, the photon upconversion system is in the form of a coating. In some embodiments, the photon upconversion system is incorporated within a polymer (e.g., dispersed in a polymer, homogeneously or heterogeneously). The polymer can be an elastomer, such as polyurethane, polycaprolactone, ethylene oxide/epichlorohydrin copolymers, and the like. In certain embodiments, the device can be coupled to a solar cell.

For example, the photon upconversion layers of the present disclosure can be added to a photovoltaic to capture subgap photons and convert them into above gap photons that can then be utilized by the cell, leading to an overall efficiency enhancement for the same amount of light. For example, the photon upconversion system of the present disclosure can be spectrally well suited to enhance the current of a SubPc:$C_{60}$ solar cell, with the sensitizer absorption outside of the absorption window of the cell and the emitter emission at the maximum external quantum efficiency (EQE) response for the cell.

Referring to FIG. 1, in some embodiments, a device 100 includes a current collector 110; an organic photovoltaic layer 120; a semi-transparent collector 130; an upconversion layer 140; and a back reflector 150. In some embodiments, the current collector is transparent to incident light. The organic photovoltaic layer can absorb incident light having an energy level greater than band gap energy of the organic photovoltaic layer. The upconversion layer can absorb incident light having an energy of less than the band gap energy of the organic photovoltaic layer, and transfer the energy to the organic photovoltaic layer 120 via triplet-triplet annihilation upconversion. In some embodiments, a window and/or insulating layer can be present between layers 130 and 140 and/or between layers 140 and 150.

In Example 1, below, a completely heavy atom-free red-to-yellow triplet-triplet annihilation (TTA) photon upconversion system using a thionated squaraine sensitizer was demonstrated both in fluid solution and in a solid-state composite architecture. The thiosquaraine [2-(4-(dibutylamino)phenyl)-4-(4-(dibutyliminio)cyclohexa-2,5-dien-1-ylidene)-3-thioxocyclobut-1-enethiolate] exhibited an intense red absorption band, no measurable room-temperature fluorescence, and a native triplet lifetime on the order of 20 μs. This triplet was readily quenched ($k_Q=1.4\times10^9$ $M^{-1}$ $s^{-1}$) upon sensitizing the triplet excited state of rubrene as a model upconversion emitter. A 0.27 eV anti-Stokes shift was observed, with selective 685 nm excitation of the thiosquaraine resulting in upconverted rubrene fluorescence centered at 570 nm. The system showed an upconversion quantum yield of ~1.5% in deaerated toluene solution. This quantum yield was defined based on a maximum 50% quantum yield for TTA upconversion. This system exhibited upconversion under filtered (650 nm longpass) simulated solar illumination and an intensity transition from quadratic to linear optical power dependence at ~150 W/$cm^2$ under 685 nm laser diode illumination. This thiosquaraine system was also used to demonstrate red-to-yellow photon upconversion in a solid-state polymer composite, a prerequisite for light-harvesting device integration. In contrast to traditional TTA upconversion photosensitizers incorporating cost-prohibitive precious metals or photolabile arylhalide groups, an easily-tunable squaraine dye which served as a promising red-absorbing heavy atom-free upconversion sensitizer for increased scalability and photostability is described herein.

Example 2 describes a red-to-blue triplet-triplet annihilation upconversion with a heavy-atom-free thiosquaraine sensitizer.

EXAMPLES

Example 1. Heavy Atom-Free Red-To-Yellow Photon Upconversion in a Thiosquaraine Composite Presented herein is a metal-free and entirely heavy atom-free TTA upconversion system utilizing a strongly-absorbing thionated squaraine dye as the triplet sensitizer to convert low-energy red photons to higher-energy yellow photons. This heavy atom-free upconversion system operates under filtered non-coherent, simulated solar illumination. The squaraines were synthesized through simple, single-step reactions, illustrated in FIG. 2. The triplet state of the thiosquaraine was readily quenched by introducing rubrene in deaerated toluene solution, indicating efficient TTET, a key step to photon upconversion. For solar photovoltaic applications, upconversion systems that can be processed as thin-film solid-state coatings are desirable for device integration. As such, the thiosquaraine sensitizer was also used to demonstrate photon upconversion from in a thin-film composite architecture.

Figure 2:
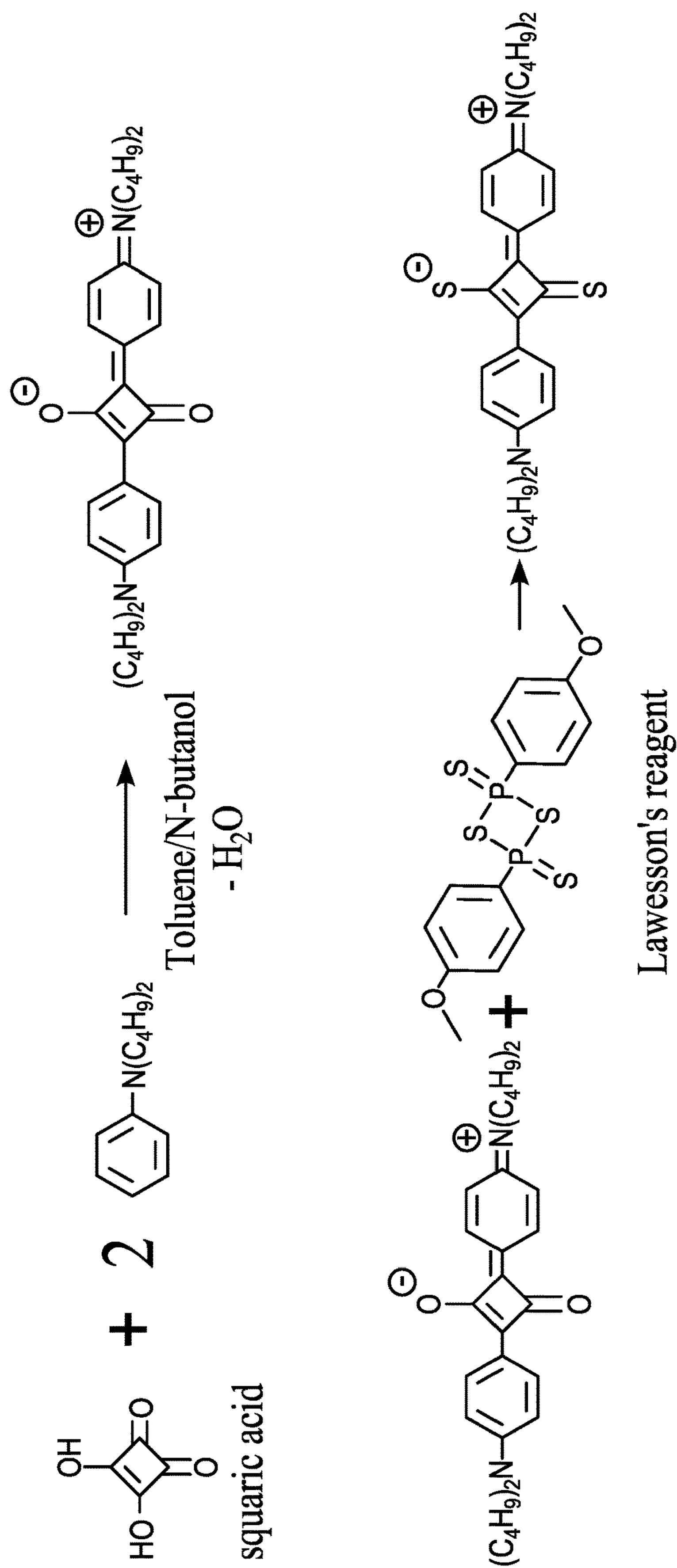
FIG. 2 is an embodiment of a method of synthesizing a squaraine and a method of synthesizing an embodiment of a sensitizer of the present disclosure.

FIG. 2 shows the reaction scheme of the squaraine and thiosquaraine. The full synthetic procedure is described below.

Squaric acid (99%) and Lawesson's reagent (97%) were purchased from Sigma-Aldrich® and used without further purification. Rubrene (>99%) was purchased from TCI Chemicals and used without further purification. An epichlorohydrin/ethylene oxide copolymer (65% epichlorohydrin) was purchased from Scientific Polymer Products, Inc. Anhydrous toluene was purchased from various suppliers and distilled under argon. Anhydrous THF (99%) was purchased from Sigma-Aldrich®.

Figure 3:
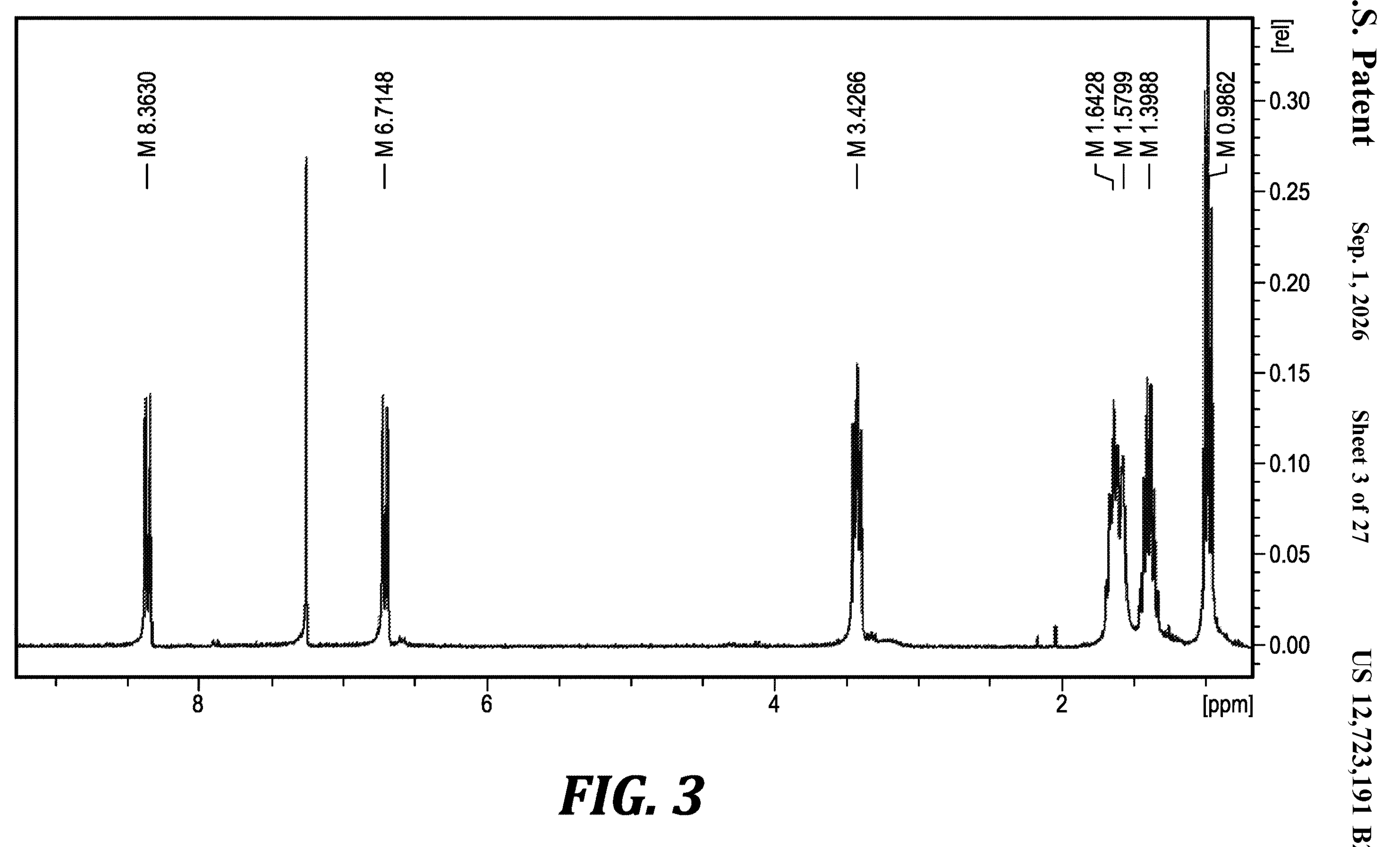
FIG. 3 is a nuclear magnetic resonance spectrum of an embodiment of a squaraine compound.

Synthesis of 2-[4-(dibutylamino)phenyl]-4-[4-(dibutyliminio)cyclohexa-2,5-dien-1-ylidene]-3-oxocyclobut-1-en-1-olate: the parent squaraine was synthesized by combining squaric acid (FIG. 2) and dibutylaniline in a round-bottom flask equipped with a Dean-Stark apparatus. The mixture was dissolved in 50 mL of 1:1 toluene/N-butanol then stirred under reflux for 5 hours. The solvent was removed, and the crude material was purified by column chromatography on silica gel. The structure was confirmed via $^1$H-NMR (FIG. 3).

Figure 4:
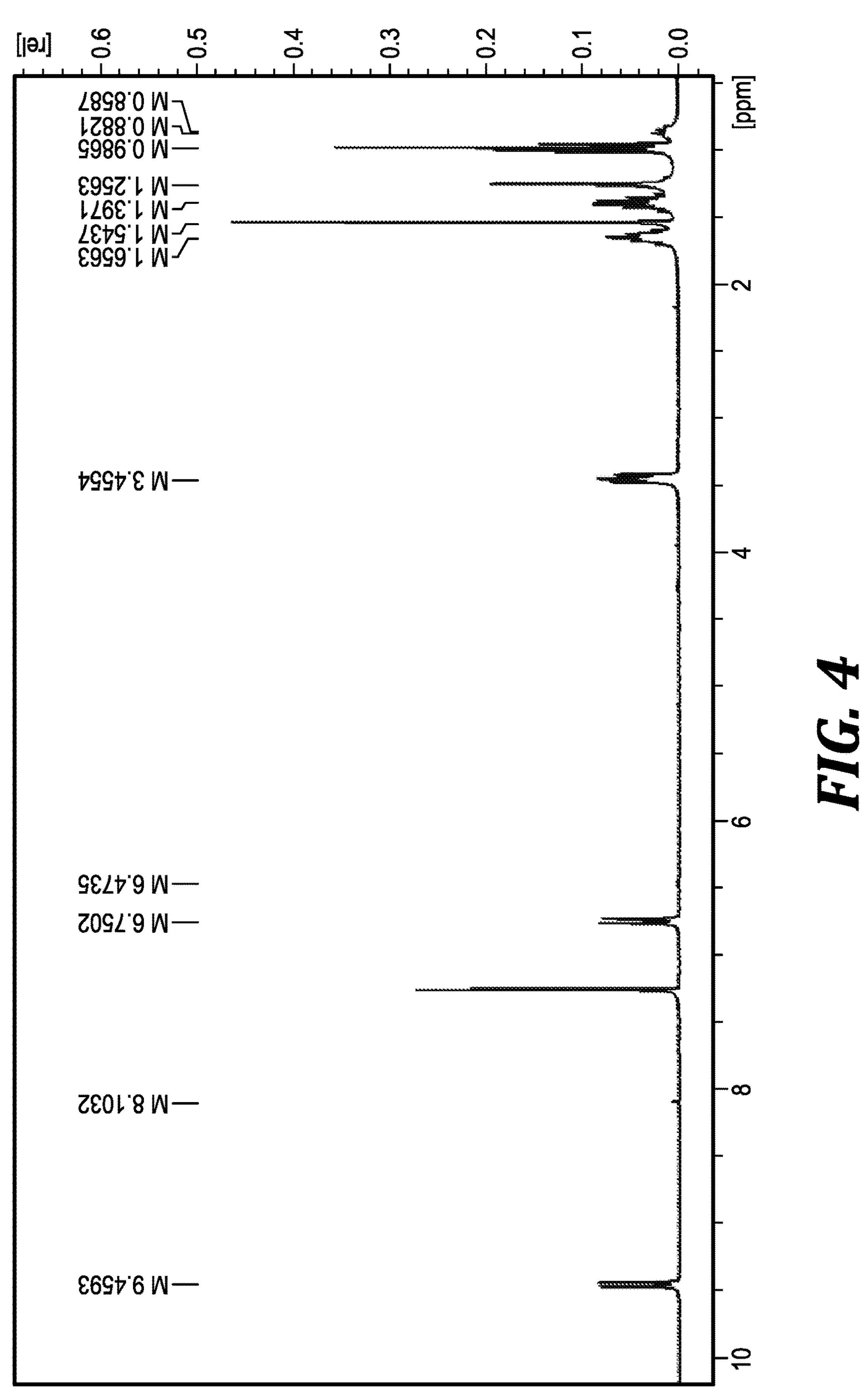
FIG. 4 is a nuclear magnetic resonance spectrum of an embodiment of a sensitizer of the present disclosure.

Synthesis of 2-(4-(dibutylamino)phenyl)-4-(4-(dibutyliminio)cyclohexa-2,5-dien-1-ylidene)-3-thioxocyclobut-1-enethiolate (thiosquaraine): Thiosquaraine was synthesized by combining the parent squaraine with Lawesson's reagent in a 0.7:1 mol ratio. The mixture was dissolved in toluene in an argon glovebox and stirred at room temperature for 45 minutes, over which time the color of the solution changed from blue to green. The crude product was purified by column chromatography on silica gel. The structure was confirmed via $^1$H-NMR (FIG. 4).

Sample preparation: Samples were prepared and sealed in an argon glovebox using dried and degassed toluene. Sample concentrations ranged from 6 to 100 μM for the thiosquaraine and from 0.01 to 0.5 mM for the rubrene.

Film preparation: Approximately 1 mg of epichlorohydrin/ethylene oxide copolymer was dissolved in 3 mL of THF. 100 μL of a 0.95 mM thiosquaraine solution and 100 μL of a 20 mM rubrene solution (both in toluene) were added to 3 mL of the polymer/THF solution. The polymer solution was drop cast onto glass slides and dried in an argon glovebox. For anaerobic spectroscopic characterization, films were placed in a small vacuum chamber and evacuated.

Steady-state optical characterization: Ground-state absorption spectra were collected using a Cary-5000 UV-vis-NIR spectrometer. Steady-state photoluminescence (PL) and photoinduced absorption (PIA) were acquired on a home-built spectrometer, as previously described in Corp, K. L.; Schlenker, C. W., Ultrafast Spectroscopy Reveals Electron-Transfer Cascade That Improves Hydrogen Evolution with Carbon Nitride Photocatalysts. *J. Am. Chem. Soc.* 2017, 139, 7904-7912, incorporated herein in its entirety, using amplitude-modulated excitation and phase-sensitive detection. Samples were irradiated with a modulated (200 Hz) 50 mW 685 nm laser diode (ThorLabs, HL6750MG).

Transient Absorption (TA) Spectroscopy: Samples were irradiated with the 700 nm output of an optical parametric amplifier (Coherent, Inc./Light Conversion OPerA Solo) that was pumped by a 1 kHz Ti:sapphire amplifier (Libra-HE, Coherent, Inc.). Incident photon density was $4.6\times10^{14}$ photons/cm$^3$/pulse. Transient absorption spectra were acquired using white-light probe pulses (2 kHz, EOS, Ultrafast Systems Inc.) from a supercontinuum laser based on a photonic crystal fiber (Leukos—Limoges, France), which is electronically delayed from the pump. Spectra were collected with a CMOS sensor and InGaAs fiber-coupled multichannel photodiode array spectrometer and plotted as the differential optical density, $\Delta OD=\log_{10}[I_{0\ sample}/I_{ex\ sample}\times I_{ex\ ref}/I_{0\ ref}]$. To minimize any potential influence of sample degradation, kinetics traces were recorded with random time steps. Spectra were measured in a 2 mm path length quartz cuvette sealed under argon and with continuous stirring. Surface Xplorer software (Ultrafast Systems Inc.) was used to collect and process spectra and OriginPro was used to analyze and plot the data.

Time-resolved photoluminescence: Time-resolved PL spectra were collected using a Hamamatsu streak camera (C10910) with a slow-sweep unit (M10913-01). Samples were irradiated with the 700 nm output of a Coherent, Inc./Light Conversion OPerA Solo optical parametric amplifier (OPA) that was pumped with 50 fs pulses from a 1 kHz Ti:sapphire amplifier (Libra-HE, Coherent, Inc.) with an average incident photon density of $1.4\times10^{14}$ photons/cm$^3$/pulse.

Global analysis: To model time-resolved spectral decay parameters, global analyses were performed using Glotaran, a graphical user interface for the R-package TIMP, a problem solving platform for fitting superposition models. Global analysis is a method to analyze the superposition of Evolution Associated Difference Spectra (EADS) that appear in transient spectroscopy, weighted by their concentration over time. The overall transient spectrum, $\psi(t, \lambda)$, at time t is represented as a sum of concentration-weighted spectra over the total number of components such that, $\psi(t, \lambda)=\Sigma c_i(t)\sigma_i(\lambda)$, where $c_i(t)$ and $\sigma_i(\lambda)$ correspond respectively to the time-dependent, wavelength-independent concentration and the wavelength-dependent, time-independent EADS of the $i^{th}$ species. The number of components for global analysis of thiosquairane and thiosquaraine:rubrene TA data was selected using singular value decomposition. No parameter constraints were placed on the sequential decay model.

Figure 5:
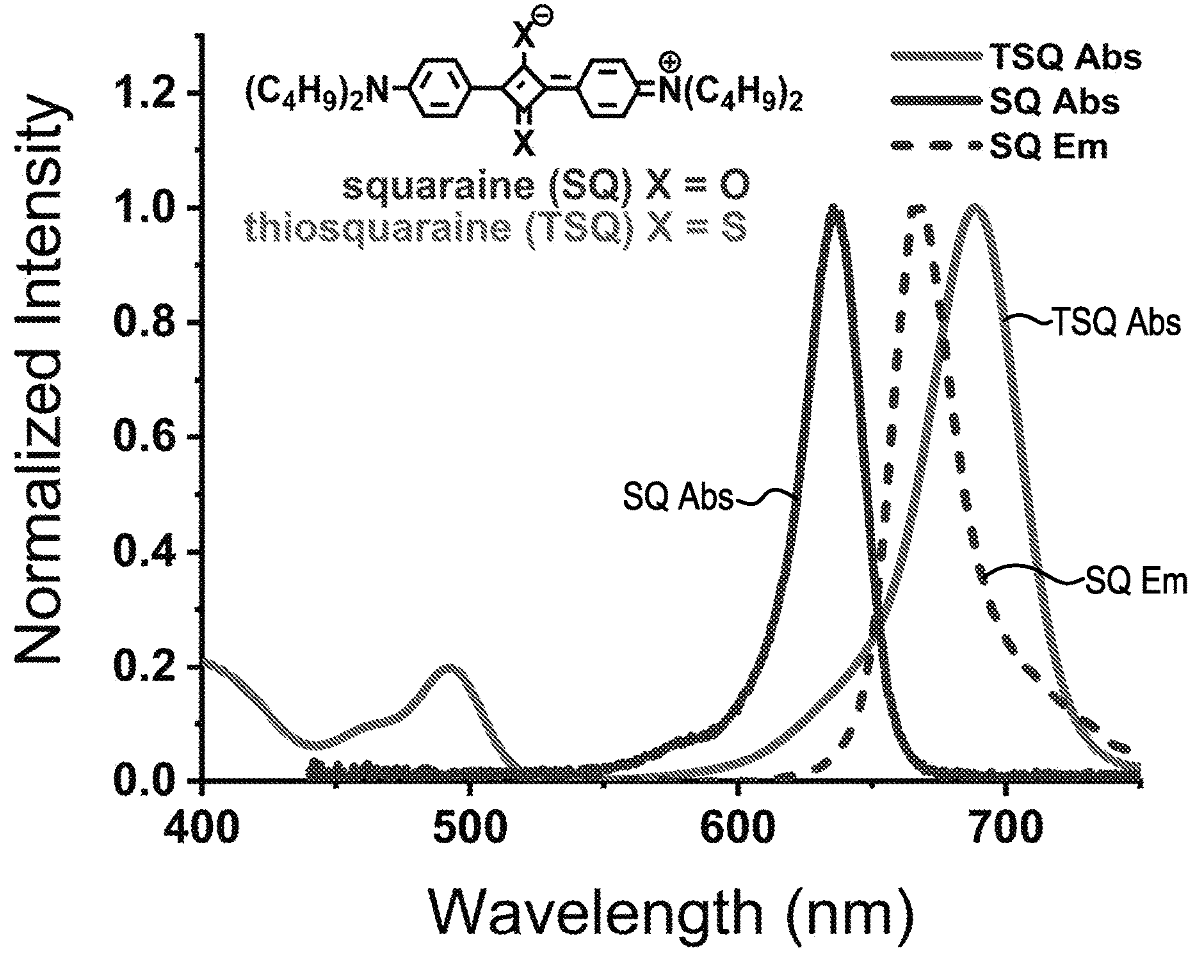
FIG. 5 is an absorbance (solid line) and room temperature emission spectra (dashed line) of an embodiment of a squaraine (SQ) and the absorbance spectrum (solid line) of thiosquaraine (TSQ) in toluene. No room-temperature emission from TSQ was observed. The chemical structures of the squaraines are displayed in the inset.
Figure 6A:
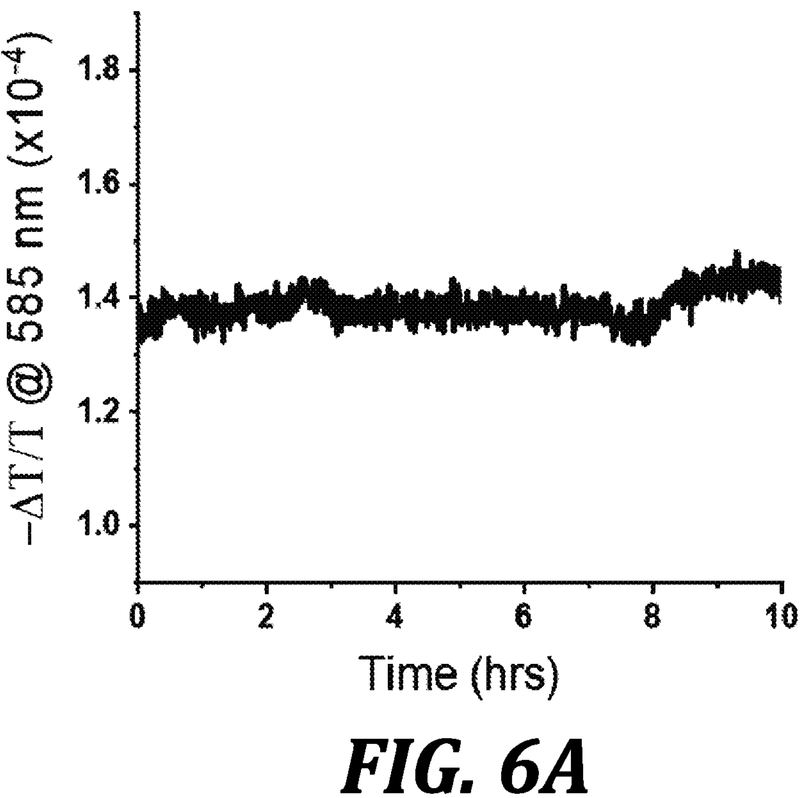
FIG. 6A is single wavelength over time monitoring of the $^3$TSQ induced absorption signal of an isolated thiosquaraine chromophore in toluene, with no rubrene added, at 585 nm over a period of at least 10 hours of pump illumination. The intensity of the triplet thiosquaraine ($^3$TSQ) photoinduced absorption signal is unchanged over this extended period, demonstrating the intrinsic photostability of the molecule in deaerated solution. The trace was done under 685 nm excitation at 75 mW/cm$^2$.
Figure 6B:
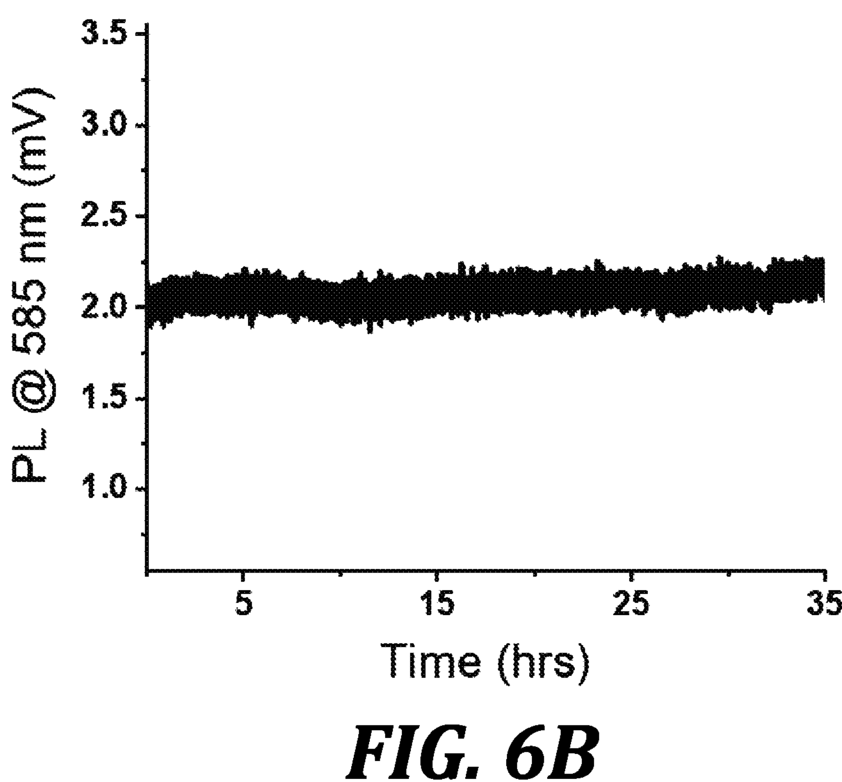
FIG. 6B is a single wavelength over time monitoring of the upconverted fluorescence signal detected at 585 nm of an isolated thiosquaraine chromophore in toluene, with no rubrene added, over a period of at least 35 hours of pump illumination. The intensity of the triplet thiosquaraine ($^3$TSQ) photoinduced absorption signal is unchanged over this extended period, demonstrating the intrinsic photostability of the molecule in deaerated solution. The trace was done under 685 nm excitation at 75 mW/cm$^2$.

The sensitizer, 2-(4-(dibutylamino)phenyl)-4-(4-(dibutyliminio)cyclohexa-2,5-dien-1-ylidene)-3-thioxocyclobut-1-enethiolate, which is referred to herein as thiosquaraine or TSQ, exhibited an intense absorption band ($1.57\times10^5$ $M^{-1}$ $cm^{-1}$) in the red portion of the visible spectrum, seen in FIG. 5. The absorbance maximum was red-shifted from 636 nm in the parent squaraine to 685 nm upon thionation. Evidence for enhanced intersystem crossing was apparent in the lack of fluorescence at room temperature from TSQ, in contrast to a fluorescence quantum yield of $\Phi_f$=0.90 that was measure for the unthionated parent squaraine. The fluorescence spectrum and decay kinetics of the thiosquaraine were observed at 80 K and are shown in FIGS. 6A and 6B. The structures of the parent and thionated squaraines are also displayed in FIG. 5.

Figure 6C:
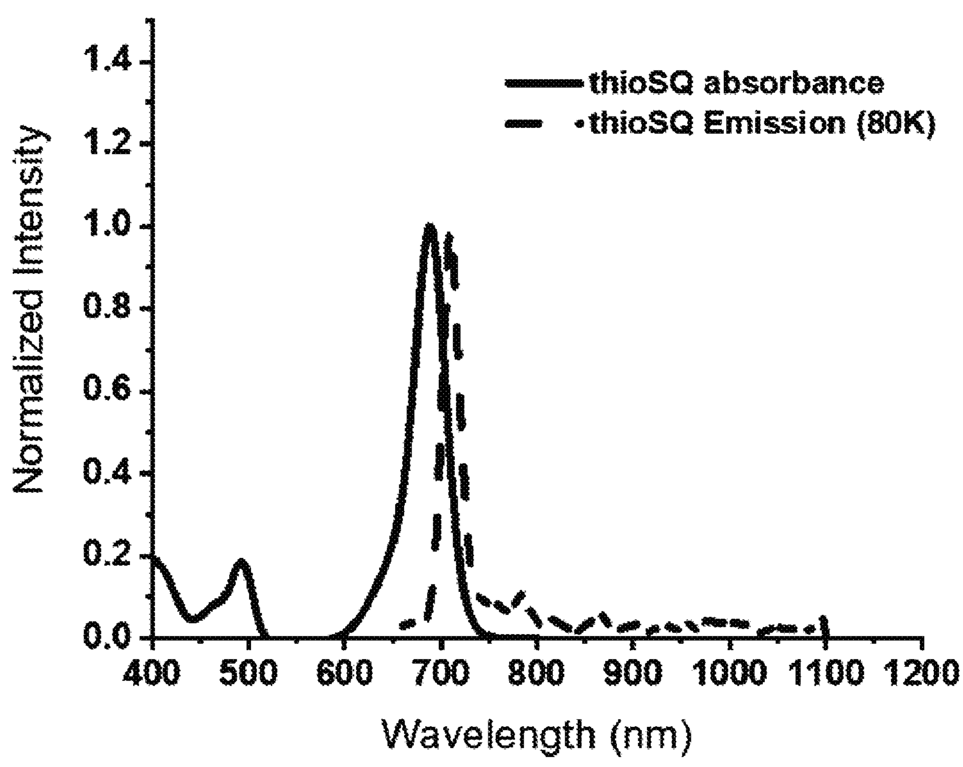
FIG. 6C is an absorbance and photoluminescence spectrum of a nitrogen purged embodiment of a sensitizer of the present disclosure (a thiosquaraine) in a glassy 2-methyl-THF matrix at 80 K, where fluorescence is observed.
Figure 6D:
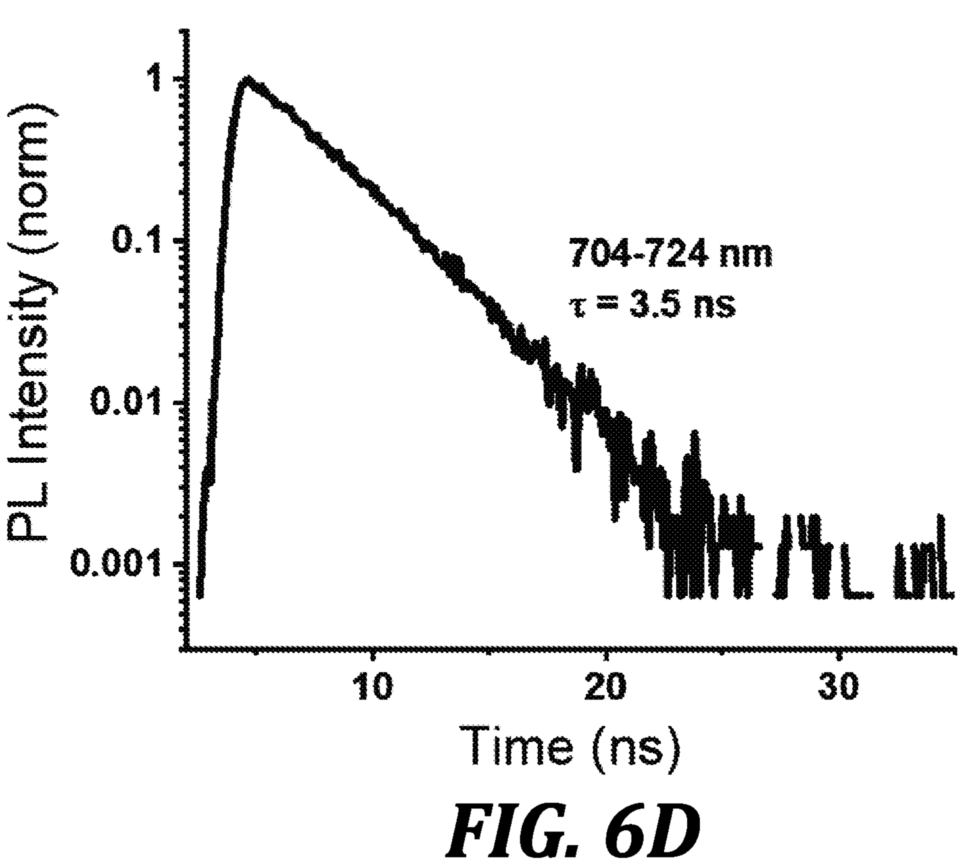
FIG. 6D is a plot of the kinetics of an embodiment of a sensitizer of the present disclosure (a thiosquaraine)'s emission at 80 K, in a glassy 2-methyl-THF matrix, showing a 3.5 ns lifetime. The short lifetime, along with the small Stokes shift, indicated that emission is from the singlet state.
Figure 6E:
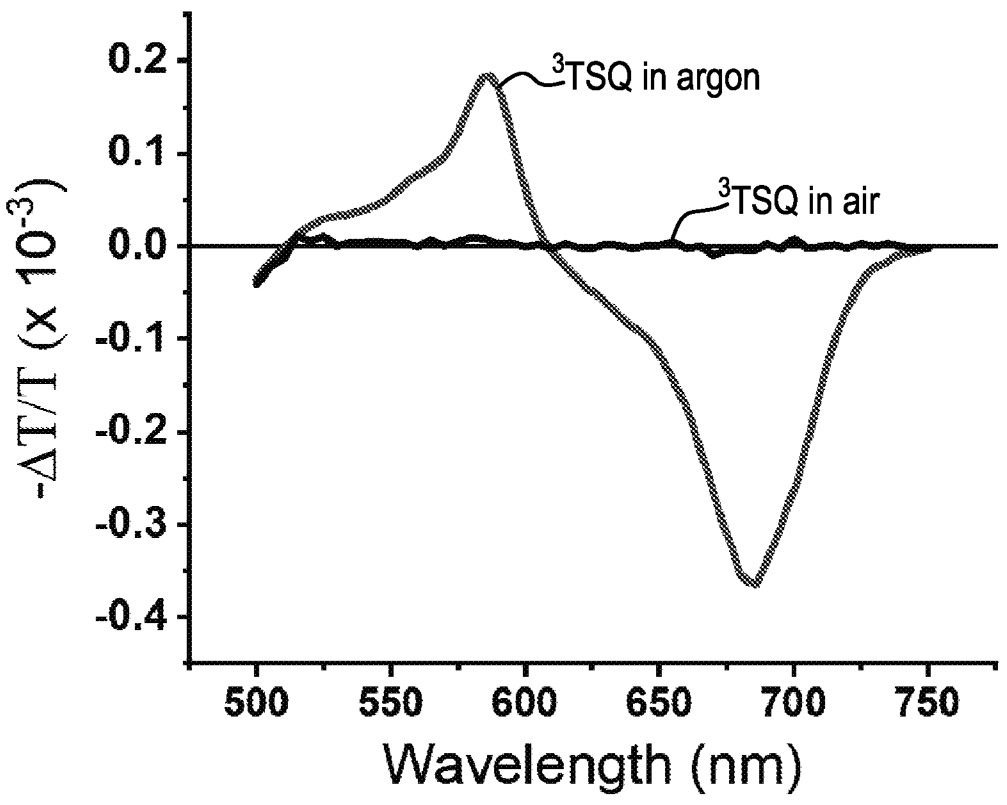
FIG. 6E is a series of quasi-steady-state photoinduced absorption (PIA) spectra of an embodiment of a sensitizer of the present disclosure (a thiosquaraine) in toluene. Under anaerobic conditions (red, $^3$TSQ in argon) there is a strong $T_1$-$T_n$ absorption at $\lambda_{probe}$~590 nm and a corresponding $S_0$-$S_1$ bleaching signature at $\lambda_{probe}$~685 nm. These features are significantly quenched in aerobic conditions (black, $^3$TSQ in air).

Photoinduced absorption (PIA) spectroscopy is a quasi-steady-state pump-probe photomodulation spectroscopy that monitors the differential transmission (ΔT) of a sample due to absorbance from long-lived, generally μs to ms, photoinduced excited-states, such as triplets and meta-stable charged species. Referring to FIGS. 6C and 6D, when plotted relative to the sample's total optical transmission (T) at a given probe wavelength (λ), the normalized negative differential transmittance −(ΔT/T) is roughly equivalent to the differential absorption that is induced by the pump beam. Positive values for the quantity −(ΔT/T) correspond to photoinduced absorption features, while negative −(ΔT/T) values correspond to increases in transmission, or photoinduced bleaching. PIA measurements of the thiosquaraine in degassed toluene showed an induced absorption band near 590 nm (FIG. 6E), which was indicative of the thiosquaraine $T_1$-$T_n$ photoinduced absorption, and a characteristic negative peak corresponding to bleaching of the singlet ground state absorption at probe wavelengths near 685 nm. The 590 nm PIA and the concomitant bleach signal are both quenched in aerobic environments. This quenching was presumably due to the sensitization of singlet oxygen, indicating relatively efficient triplet formation on the thionated chromophore. No thiosquaraine phosphorescence was observed, even in the presence of ethyl iodide (an external heavy atom source) at low temperature. Phosphorescence would afford a quantitative measure of the TSQ $T_1$ triplet energy. However, the singlet oxygen sensitization behavior of the molecule indicates that the triplet energy is above 1 eV.

Figure 7:
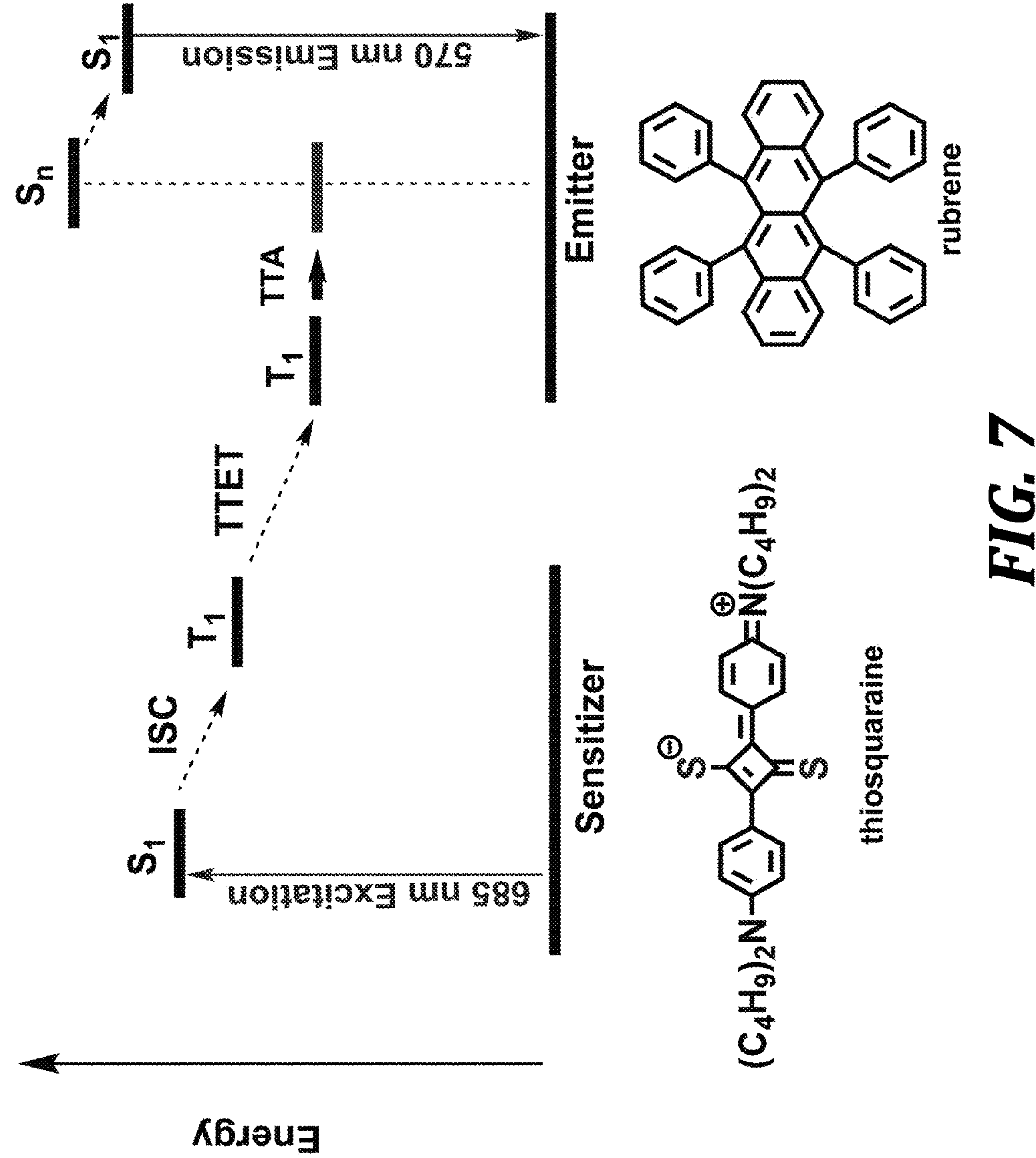
FIG. 7 is a schematic representation of an energy diagram of an embodiment of a photon upconversion system of the present disclosure.
Figure 8:
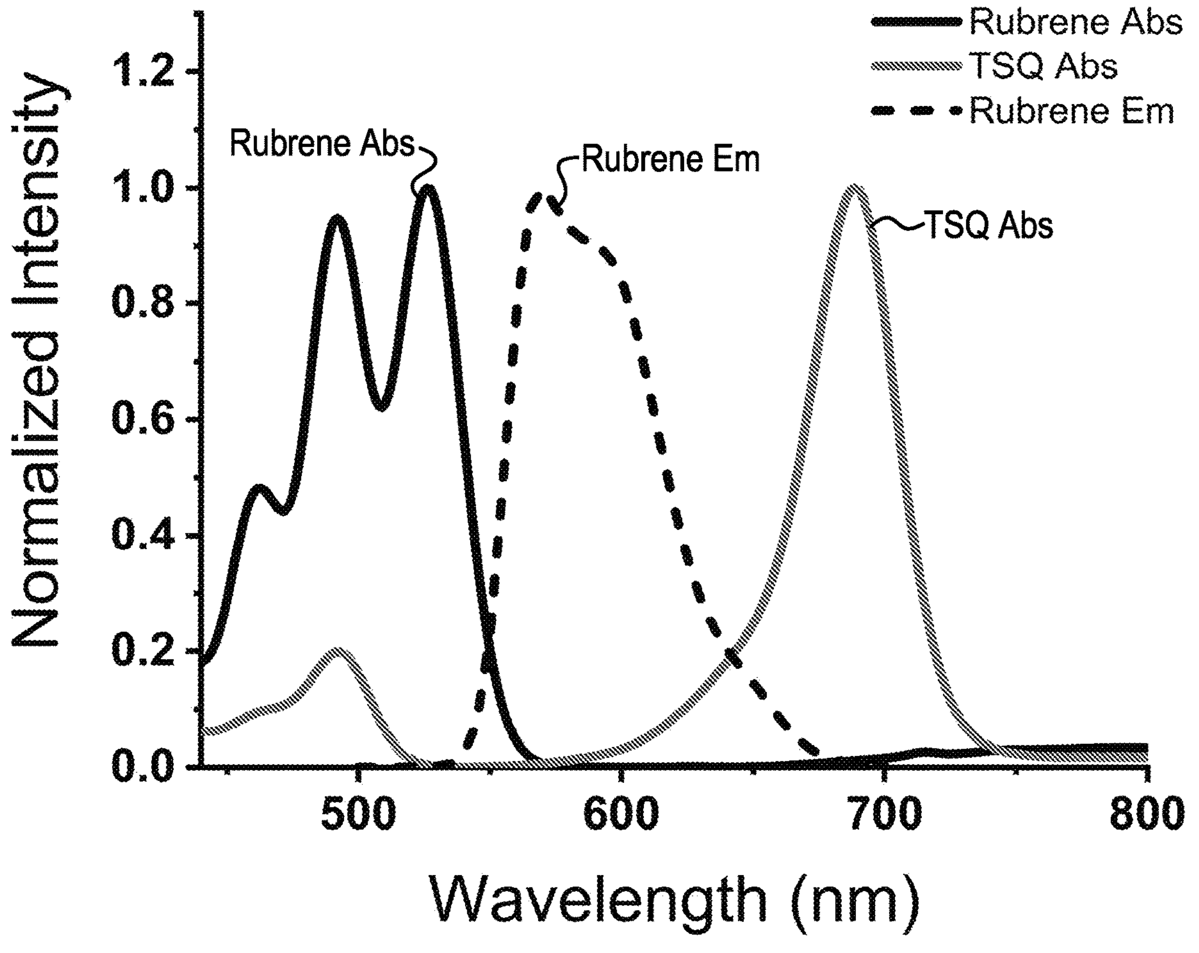
FIG. 8 is an absorption (solid black line) and emission (dashed black line) spectra of rubrene compared to the absorption spectrum of an embodiment of a sensitizer of the present disclosure (solid grey line).

Because the PIA results indicated the thiosquaraine triplet was quenched by oxygen, rubrene was selected as a model emitter molecule for the upconversion system (FIG. 7). Rubrene is a polycyclic aromatic hydrocarbon that has a triplet energy of $T_1$=1.12 eV and a $\Phi_f$ value that is near unity in solution. These properties make rubrene a suitable emitter for NIR-to-visible upconversion schemes. The ground-state absorption and emission spectra for rubrene are shown in FIG. 8, overlaid with the thiosquaraine ground-state absorption for reference. The absorbance of rubrene exhibited a peak near 525 nm, which was sufficiently spectrally distinct from the TSQ absorption to allow the selective excitation of the two chromophores independently. Perhaps more importantly, the rubrene fluorescence, which was represented by the dashed black trace in FIG. 8, exhibited only a slight spectral overlap in the region between 600-675 nm with the TSQ absorption band. Minimizing this spectral overlap was important to help curtail parasitic Förster energy transfer back to the TSQ chromophore from the rubrene singlet excited state produced by upconversion.

Figure 9:
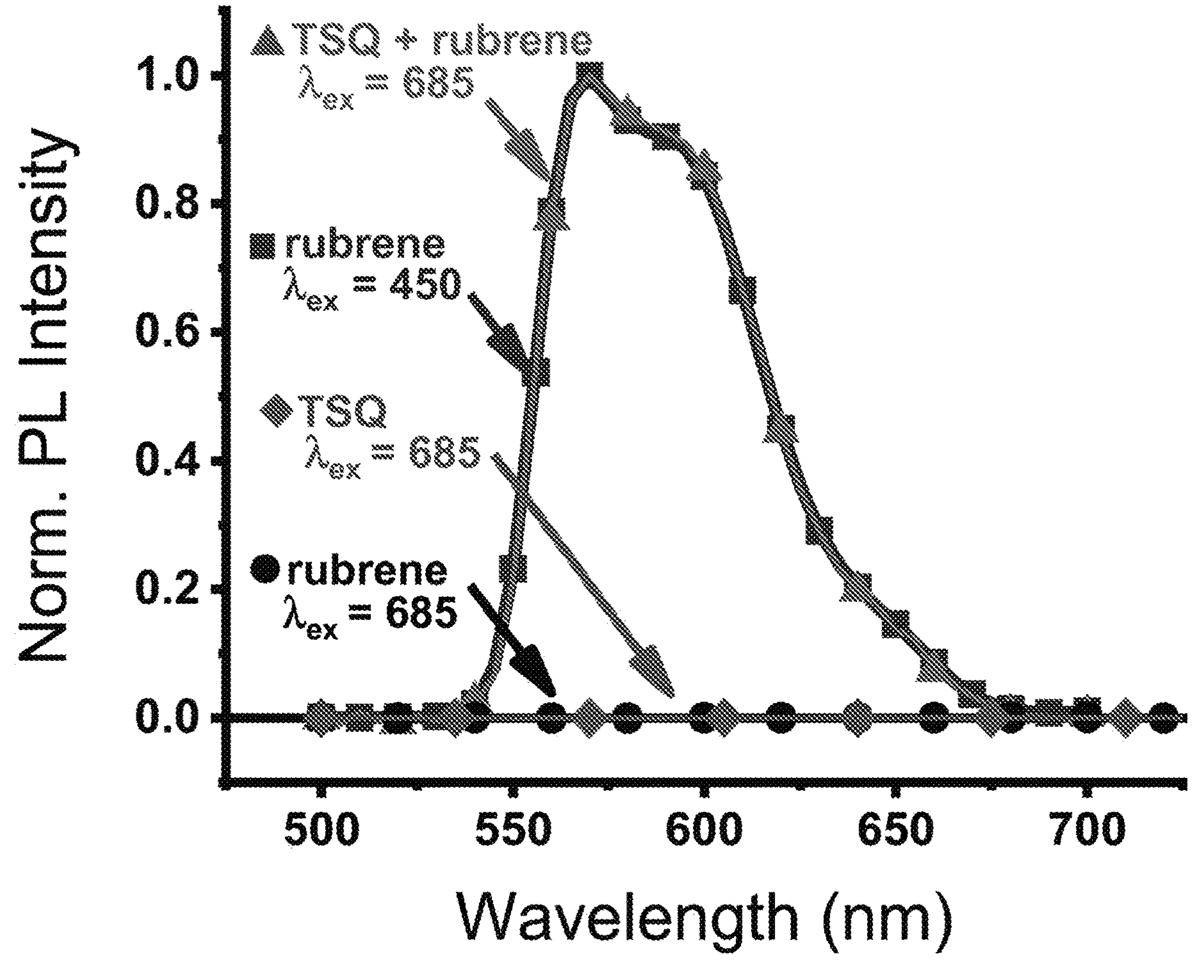
FIG. 9 is a fluorescence photoluminescence spectrum showing that in an embodiment of a photon upconversion system, selective excitation of an embodiment of a sensitizer of the present disclosure (a thiosquaraine) at 685 nm led to upconverted fluorescence from the rubrene component. This fluorescence was identical to the fluorescence observed when rubrene is excited at 450 nm. No fluorescence is observed from either individual molecule when excited in isolation at $\lambda_{ex}$=685 nm.

Selectively exciting the thiosquaraine molecule in the presence of rubrene resulted in upconverted fluorescence that was spectrally indistinguishable from the native rubrene singlet emission (FIG. 9, $\lambda_{ex}$=685 nm). The anti-Stokes shift was calculated to be 0.27 eV based on intensity weighted averages of the upconverted emission and sensitizer absorption spectra. For the excitation levels used in this study, no room-temperature fluorescence from either component was observed when the components were pumped at 685 nm in isolation from the complementary upconversion component. This was seen in FIG. 9, wherein no spectral features were observed when excited at 685 nm, unless both components were present in solution. Similarly, in a cuvette, under 685 nm excitation luminescence was only observable in the rubrene/TSQ solution. This lack of emission was important because it demonstrated that the rubrene luminescence that was observed in the upconversion system was in no way due to two-photon absorption on rubrene at the illumination intensities used in this study. The upconversion quantum yield was determined to be 0.015 in toluene, measured relative to a methylene blue reference ($\Phi_f$=0.091, ethanol) with excitation at 685 nm.

Figure 10:
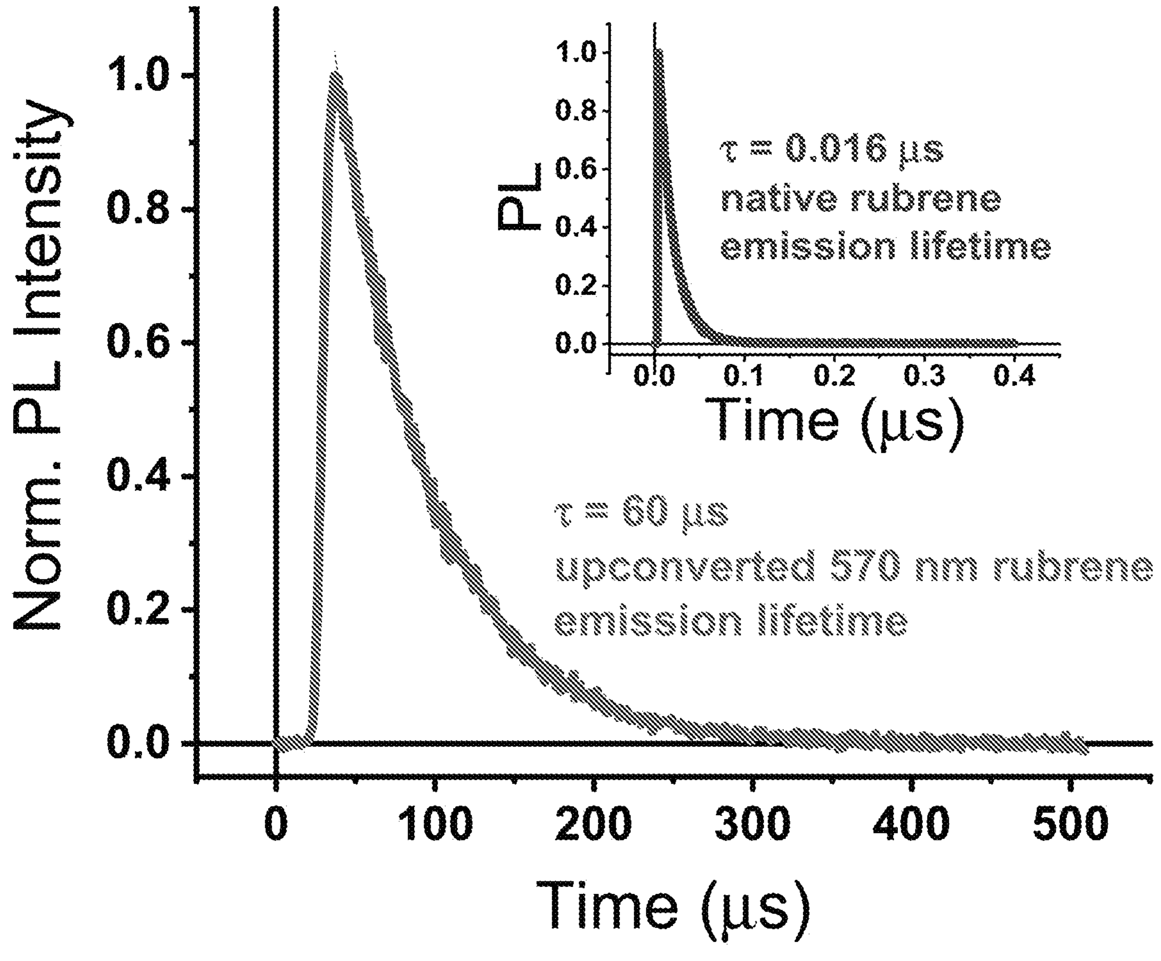
FIG. 10 is a graph showing lifetime data of an upconverted rubrene fluorescence, indicating a lifetime value of $\tau$=60 μs. The inset shows that the native rubrene fluorescence decayed with a lifetime value of $\tau$=0.016 μs when excited at 470 nm in isolation.

While FIG. 9 clearly demonstrated that the upconverted emission and the native rubrene emission are spectrally indistinguishable, the temporal response of these two signals were markedly different. To study their disparate kinetics, the decay time for the upconverted rubrene emission was monitored and compared to that of the native rubrene emission. The lifetime of the upconverted emission was significantly longer than the native rubrene fluorescence lifetime. In the upconversion sample, an increase in the rubrene-centered luminescence decay time constant to a value of τ=60 μs was observed, in contrast to a value of τ=0.016 μs for the isolated rubrene fluorescence decay in solution (FIG. 10). These results indicated that the decay time for the rubrene-centered emission in the upconversion sample was not governed by the radiative lifetime of the $S_1/S_0$ transition. Rather, the decay time of the upconverted emission depends on the rubrene triplet excited state decay time.

Figure 11A:
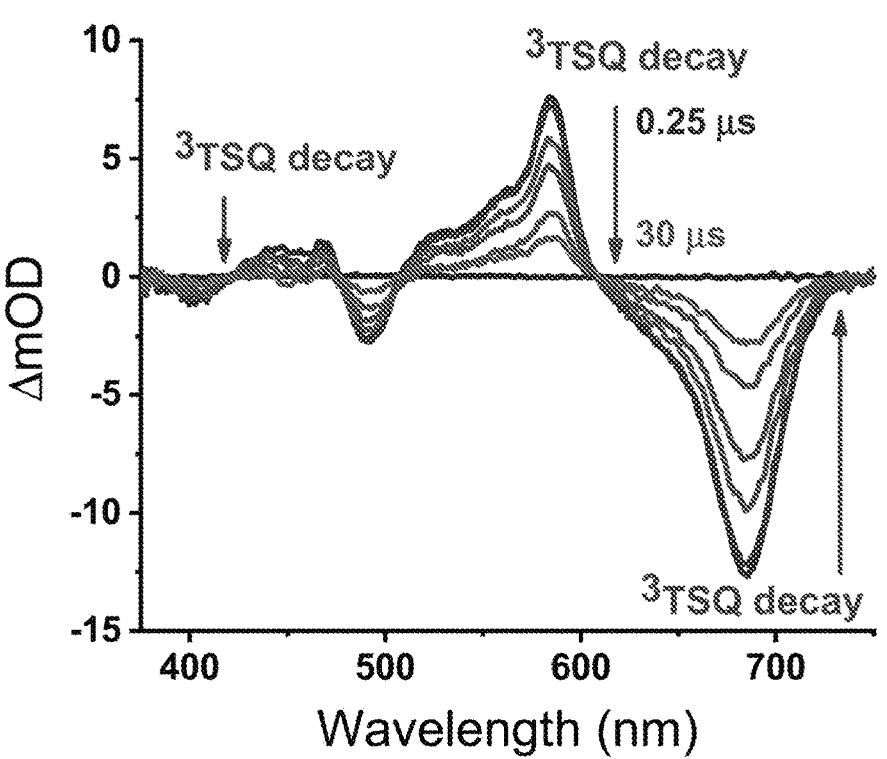
FIG. 11A is a graph showing transient absorption spectra of an embodiment of a sensitizer of the present disclosure (a thiosquaraine) in toluene, showing an induced absorption feature at 590 nm associated with the triplet.
Figure 11B:
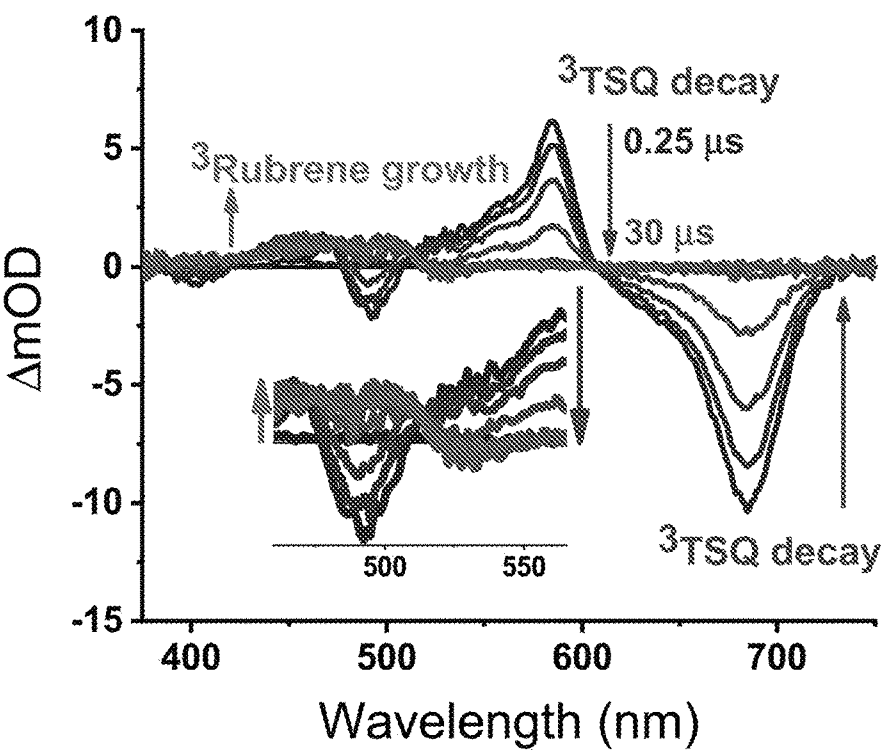
FIG. 11B is a graph showing transient absorption spectra of an embodiment of a sensitizer of the present disclosure (a thiosquaraine) in the presence of rubrene. A new induced absorption was observed from 480-510 nm associated with the rubrene triplet.
Figure 11C:
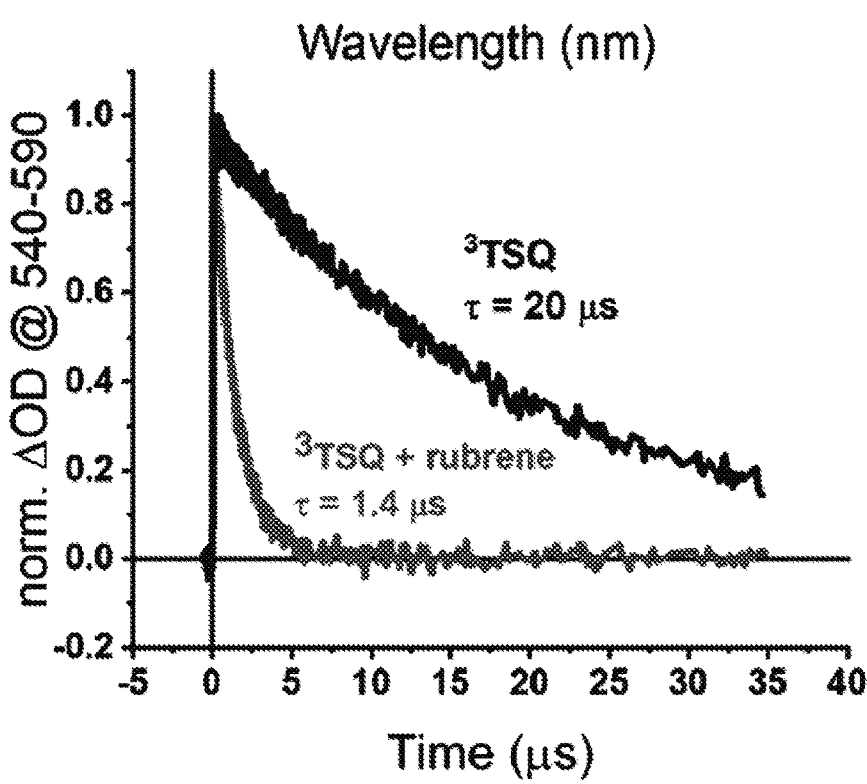
FIG. 11C is a graph showing the kinetics of the triplet absorption of an embodiment of a sensitizer of the present disclosure (a thiosquaraine) with and without the presence of rubrene, indicating dynamic quenching of the thiosquaraine triplet by rubrene.
Figure 11D:
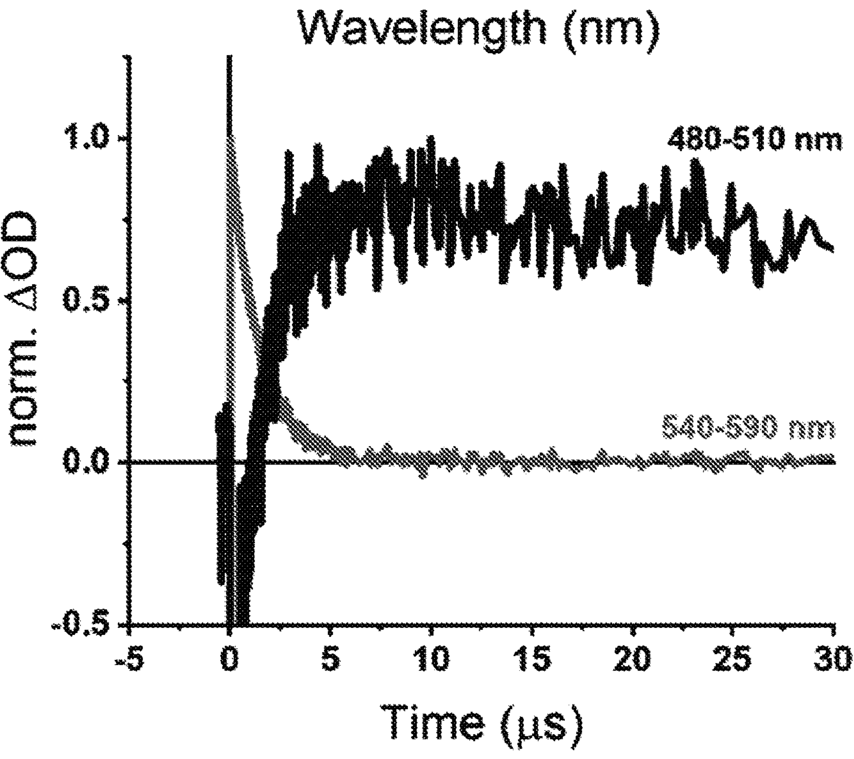
FIG. 11D is a graph showing the kinetics of an embodiment of a sensitizer triplet of the present disclosure (a thiosquaraine) in the presence of rubrene compared to the kinetics of the rubrene triplet absorption.

In order to more carefully assess the excited state dynamics of the thiosquaraine upconversion system, a kinetic analysis based on ns to μs broadband-probe transient absorption spectroscopy was used. Transient absorption (TA) is a pump-probe spectroscopy which can monitor similar excited state absorption features to those revealed in the PIA spectroscopy but with the added advantage of reporting on kinetic evolution of the system directly in the time-domain. Similar dynamic information could be qualitatively gleaned from modulation frequency-dependent PIA spectroscopy measurements. Nevertheless, broadband TA often affords the added advantage of kinetically resolving characteristic spectral fingerprints that would otherwise be intractable to spectrally disentangle. Transient absorption measurements of the neat thiosquaraine shown in FIG. 11A exhibited a nearly identical induced absorption feature to that which observed in cw-PIA studies at probe wavelengths near 590 nm. This induced absorption decayed with a time constant of 20 μs (FIG. 11C). Adding just 0.05 mM rubrene significantly decreased the time constant of this feature to 1.4 μs (FIG. 11C), indicating a marked dynamic quenching of the TSQ triplet state. Additionally, the presence of rubrene led to a new induced absorption feature from 480-510 nm, consistent with the rubrene triplet excited state, shown in FIG. 11B. This feature did not fully decay on the 35 μs timescale of the experiment (FIG. 11D). The inset of FIG. 11B showed a clear isosbestic point between the tail of the feature at 590 nm and the new feature at 495 nm. An isosbestic point was characteristic of interconversion between two species and provides strong evidence that TTET occurred from the TSQ triplet state ($^3$TSQ) to rubrene triplet state ($^3$Rubrene).

Figure 11E:
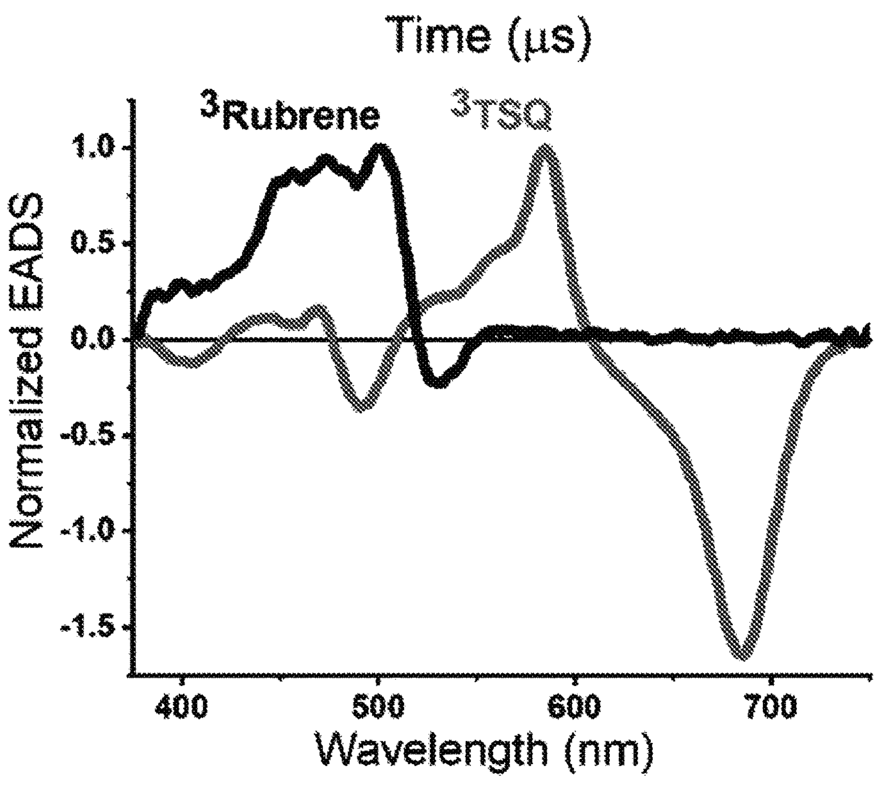
FIG. 11E is a graph of a normalized evolution associated difference spectra (EADS) of an embodiment of a sensitizer triplet of the present disclosure (a thiosquaraine) and the rubrene triplet from global analysis.
Figure 11F:
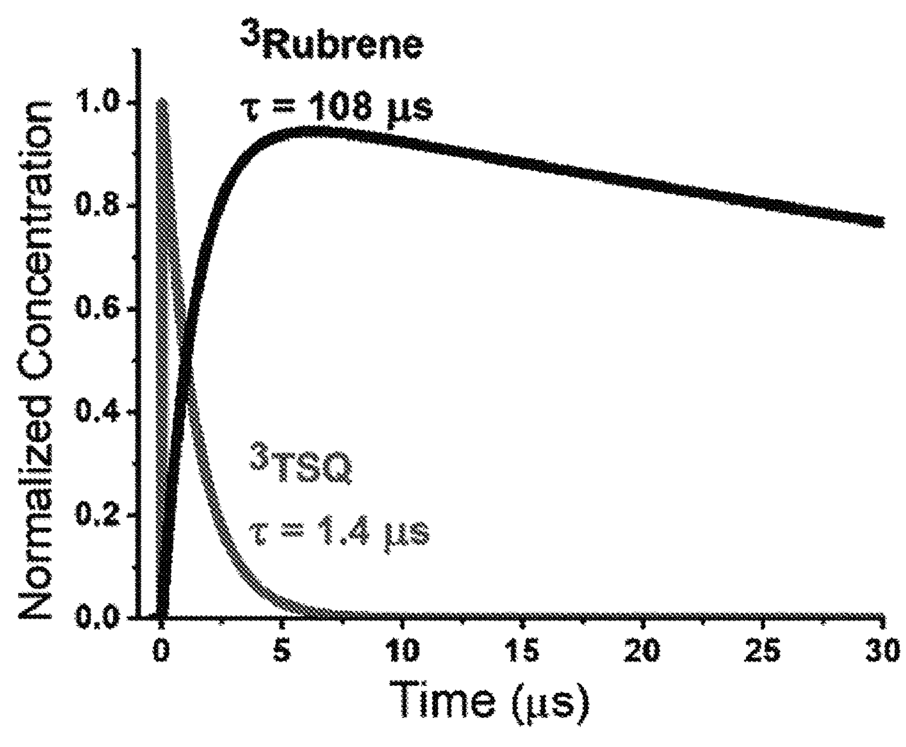
FIG. 11F is a graph of the kinetics of the rubrene triplet and a sensitizer triplet of the present disclosure (a thiosquaraine) from global analysis.
Figure 12A:
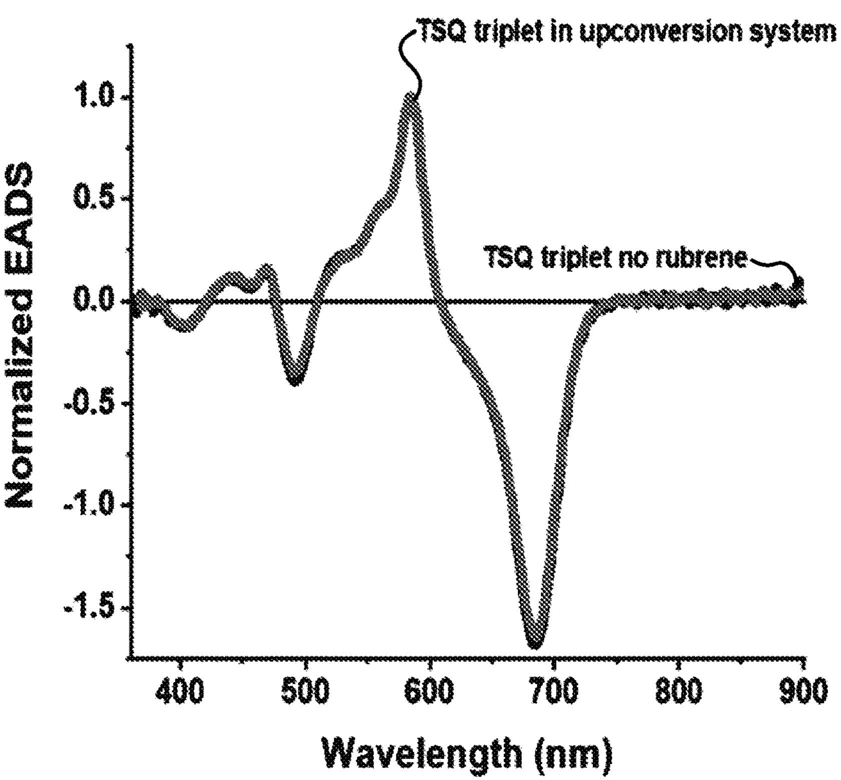
FIG. 12A is a graph of a sensitizer triplet of the present disclosure (a thiosquaraine) component extracted from global analysis from both datasets with and without rubrene. The triplet components are identical, regardless of the presence of rubrene.
Figure 12B:
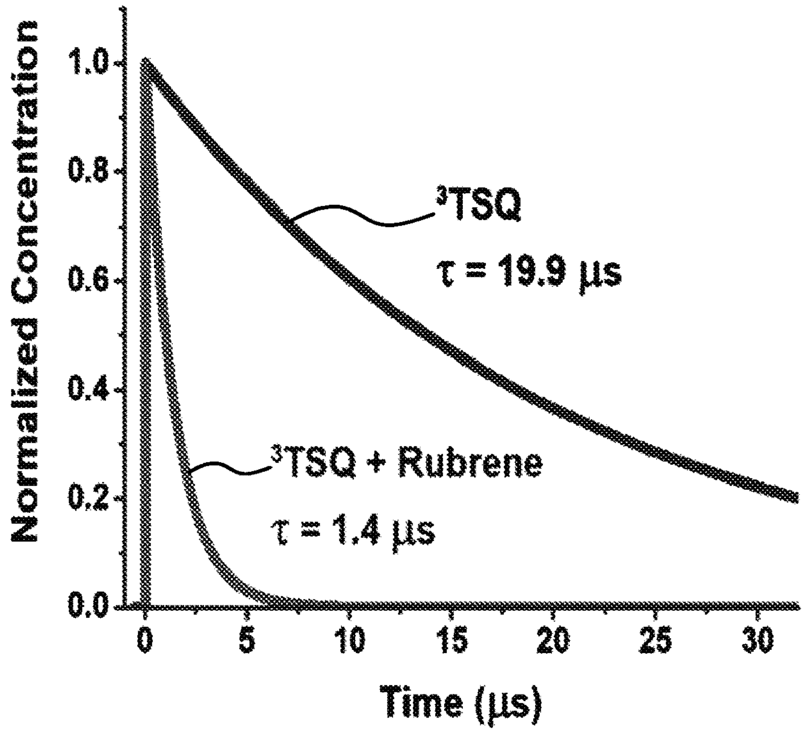
FIG. 12B is a graph of global analysis fits of the thiosquaraine triplet absorption both with and without rubrene, showing the dynamic quenching of the sensitizer triplet of the present disclosure (a thiosquaraine) state when rubrene is present. The thiosquaraine triplet lifetime was significantly quenched in the presence of rubrene.

While the isosbestic point that was observed in the ns to μs TA spectra for the thiosquarane upconversion samples reported qualitatively on the triplet energy transfer process, as described above, global analysis could provide quantitative information on the kinetics for this process. Global analysis fitting of the thiosquaraine/rubrene TA spectral evolution revealed the two spectral features shown in FIG. 11E, the first belonging to the thiosquaraine triplet and the second belonging to the rubrene triplet. The EADS corresponding to the thiosquaraine triplet was identical to the spectrum observed in the absence of rubrene, shown in FIG. 11E. The kinetic fits from global analysis showed the crossover time between the decay of the thiosquaraine triplet state and the rise of the rubrene triplet absorption (FIG. 11F and FIG. 12A). This allowed the extraction of a time constant for the decay of the TSQ triplet and the rise of the rubrene triplet associated with the energy transfer process of τ=1.4 μs (FIG. 12B). Through global analysis, the species associated with the rubrene triplet excited state was shown to decay with a 108 μs lifetime.

Figure 13A:
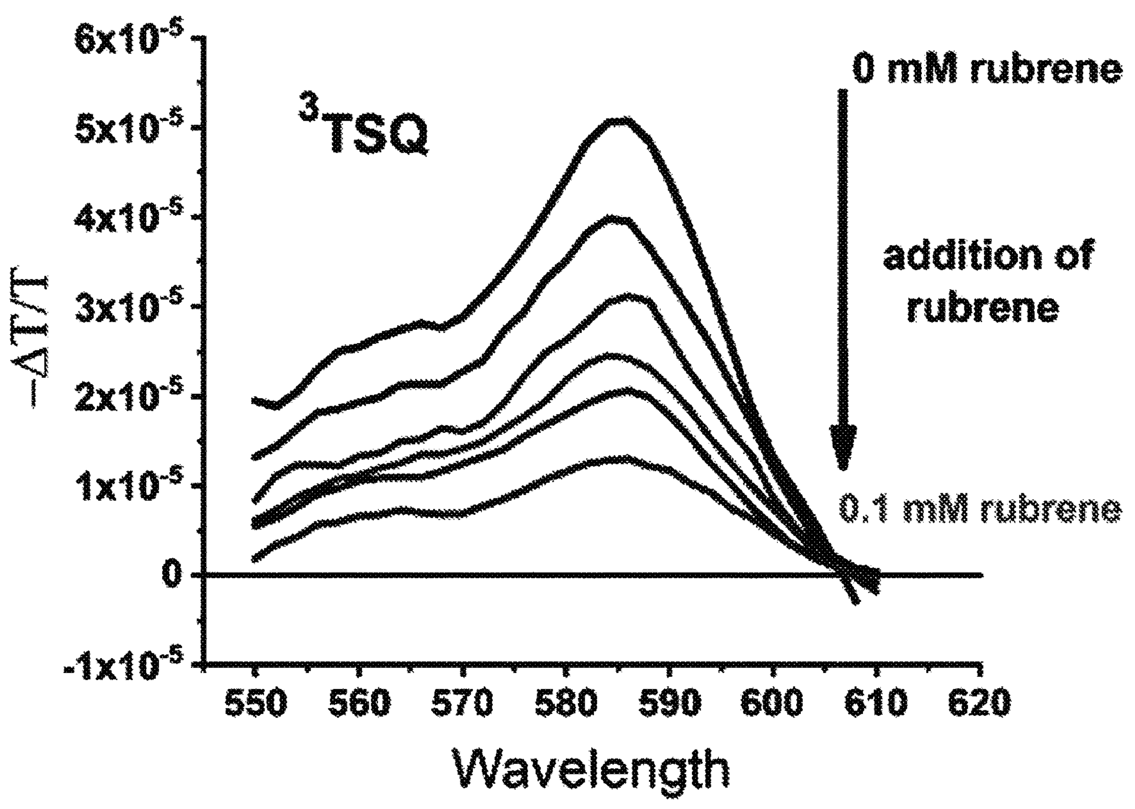
FIG. 13A is a quasi-steady-state photoinduced absorption (PIA) spectra of an embodiment of a sensitizer of the present disclosure (a thiosquaraine) with rubrene concentrations ranging from 0 to 0.1 mM, revealing quenching of the thiosquaraine triplet. Spectra collected with photomodulation frequencies of 200 Hz.
Figure 15A:
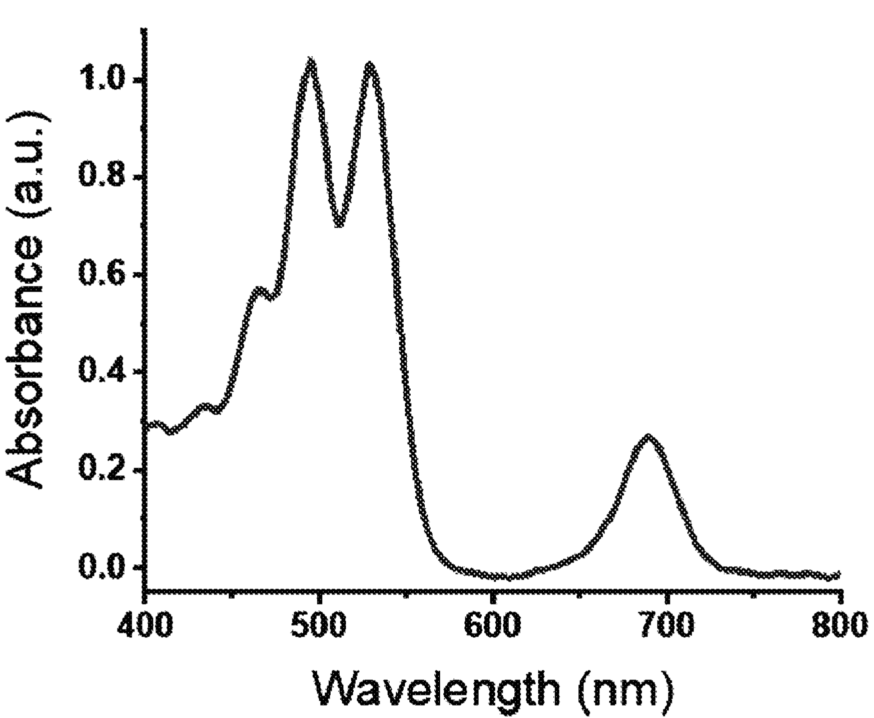
FIG. 15A an absorbance spectrum of an embodiment of a thiosquaraine/rubrene film in an ethylene oxide-epichlorohydrin (EO-EPI) copolymer.
Figure 15B:
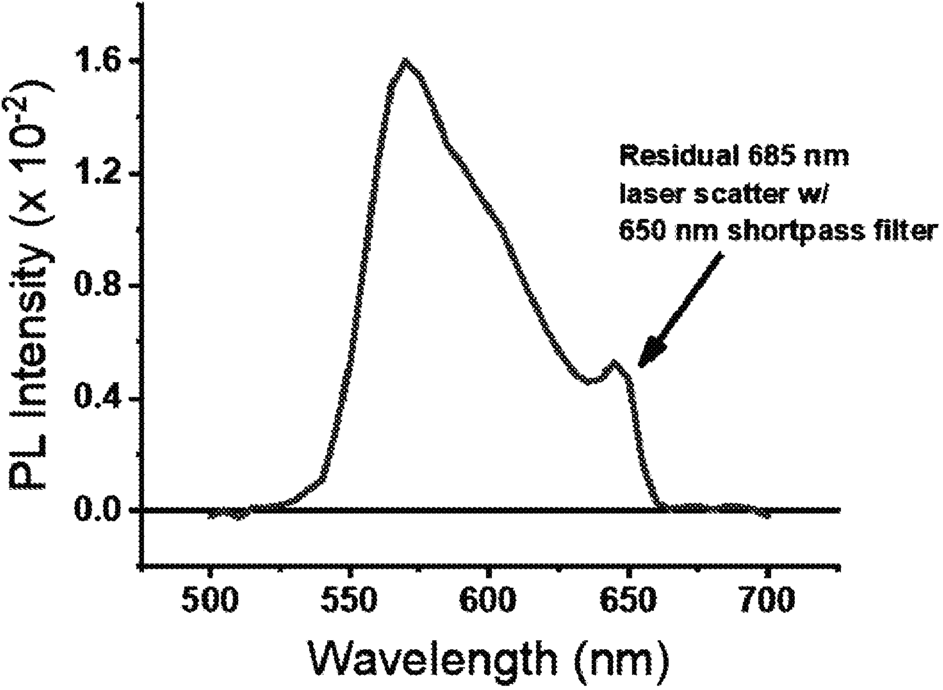
FIG. 15B an emission spectrum of an embodiment of a thiosquaraine rubrene EO-EPI film.

Having established the dynamic nature of the quenching process and the $^3$TSQ lifetime in the absence of an external quencher, the concentration-dependence of the quenching was measured to determine the quenching rate constant ($k_Q$) for the triplet energy transfer process. Stern-Volmer analysis is frequently used to quantitatively measure the quenching of the sensitizer triplet state by an annihilator molecule. For upconversion systems, especially those relying on metal complexes as sensitizers, phosphorescence quenching is most frequently used for Stem-Volmer analysis. No measurable phosphorescence was observed from the thiosquaraine molecule, which makes it intractable to perform a traditional Stem-Volmer quenching analysis based on luminescence quenching to determine $k_Q$. Nevertheless, similarly to the TA measurements, adding rubrene quenched the $^3$TSQ induced absorption in the quasi-steady state photoinduced absorption measurement as well, shown in FIG. 13A. This effect allows the use of intensity quenching of this $^3$TSQ induced absorption signature for a modified Stem-Volmer analysis (FIG. 15B), as outlined in Equations 1 and 2:

$$\left(\frac{\Delta T}{T}\right)_0 / \left(\frac{\Delta T}{T}\right) = 1 + K_{SV}[Q] \quad \text{Eq. 1}$$

$$K_{SV} = k_Q * \tau_{\ ^3TSQ} \quad \text{Eq. 2}$$

Figure 13B:
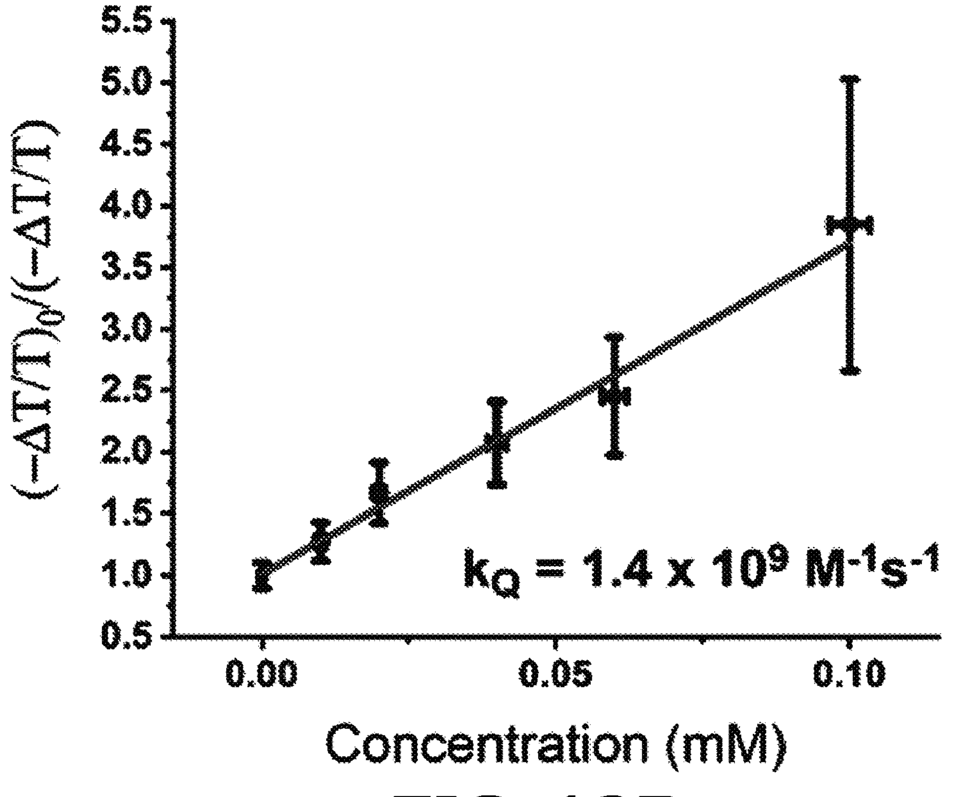
FIG. 13B is a plot of a Stem-Volmer analysis of the PIA quenching data in FIG. 13A, showing a thiosquaraine triplet quenching rate constant of $k_Q=1.4\times10^9\ M^{-1}\ s^{-1}$.

Here, $(\Delta T/T)_0$ is the native $^3$TSQ absorption intensity in the absence of rubrene, $(\Delta T/T)$ is the $^3$TSQ absorption intensity at each rubrene concentration, $K_{SV}$ is the Stem-Volmer quenching constant, and [Q] is the concentration of the quencher. $K_{SV}$ is a product of $k_Q$, the quenching constant, and $\tau^3$TSQ, the triplet lifetime, taken from transient absorption (τ=20 μs, FIG. 11C). Thus, using the ratio of intensities of the photoinduced absorption triplet signal, with and without rubrene, and the native triplet lifetime a value for the $^3$TSQ quenching constant of $k_Q=1.4\times10^9$ $M^{-1}$ $sec^{-1}$ was recovered (FIG. 13B). For this system, such a value for $k_Q$ is roughly associated with diffusion-controlled quenching dynamics.

Figure 13C:
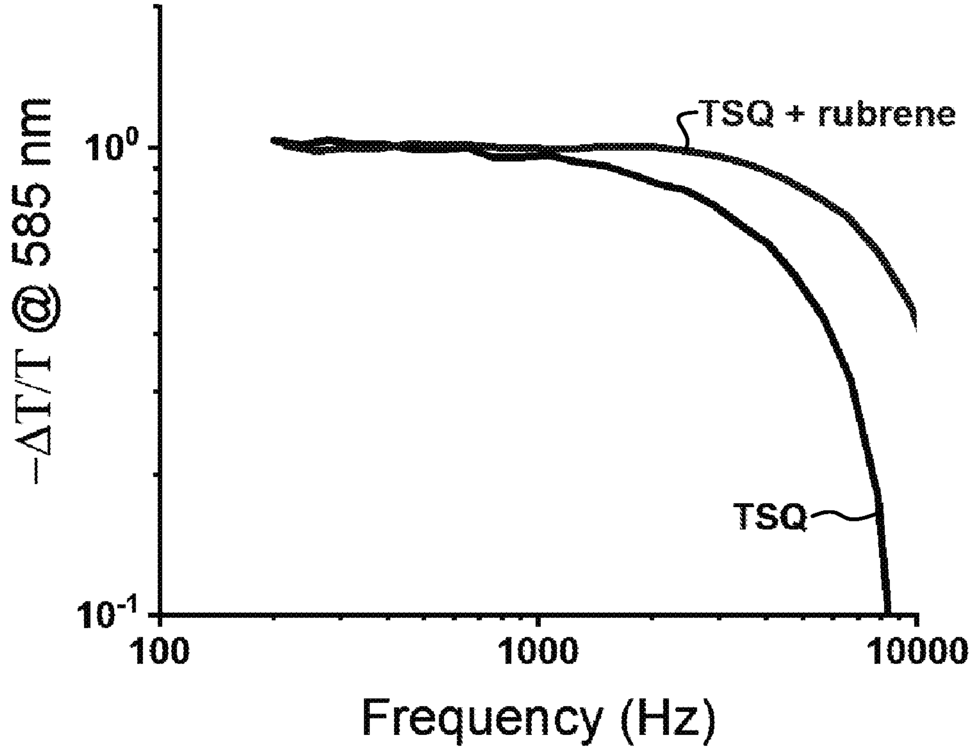
FIG. 13C is a graph of frequency modulation dependence data of an embodiment of a sensitizer triplet of the present disclosure (a thiosquaraine) as monitored in the quasi-steady state method of photoinduced absorption. For this data, the probe wavelength was set to 585 nm and the modulation frequency of the 685 nm pump was varied. The monitored photoinduced absorption signal would have a flat response until the modulation frequency became too fast for the population of photoexcited chromophores to decay within the modulation cycle of the optical excitation. At this point the amplitude of the PIA signal diminishes with increasing modulation frequency. Thus, spectral features with a longer lifetime exhibited a roll-off behavior at lower frequencies than those with shorter lifetimes. The frequency role-off occurred at lower frequencies for the isolated thiosquaraine than for thiosquaraine in the presence of rubrene, indicating that the presence of rubrene shortens the lifetime of the thiosquaraine triplet.

FIG. 13C shows the frequency modulation dependence of the thiosquaraine triplet absorption, monitored with a probe wavelength 585 nm. As the frequency of the photomodulation increased, a drop off in signal was expected. This drop-off happens at lower frequencies for species that have longer lifetimes. When in the presence of rubrene, the frequency response was flattened with respect to the native thiosquaraine triplet response, suggesting a shorter lifetime in the presence of rubrene Since the cw-PIA measurements required the sample to be stable over an extended period of measurement time, typically anywhere between 30 minutes and 12 hours of illumination depending on the required signal-to-noise ratio, the photostability of $^3$TSQ absorption signal was also monitored by tracking its intensity as a function of illumination time. As shown in FIG. 6A, the $^3$TSQ absorption signal exhibited robust photostability, with no loss in upconversion intensity over a period of at least 10 hours of illumination in deaerated solution. A similar experiment was run for the upconverted emission, showing photostability over a period of time in excess of 35 hours of illumination (FIG. 6B).

As the TTA photon upconversion process outputted one high-energy photon from two input low-energy photons, the upconverted emission intensity would have a quadratic dependence on the incident power density in the weak annihilation limit. However, as the pseudo-first order rate constant of the triplet acceptor decay became much larger than the rate constant of the second order TTA process, the emission intensity would exhibit a linear relationship to incident power density. This saturation limit is important for determining the most efficient power density for the upconversion process, as well as for evaluating the practicality of a system for solar applications, where the incident power density was low.

Figure 14:
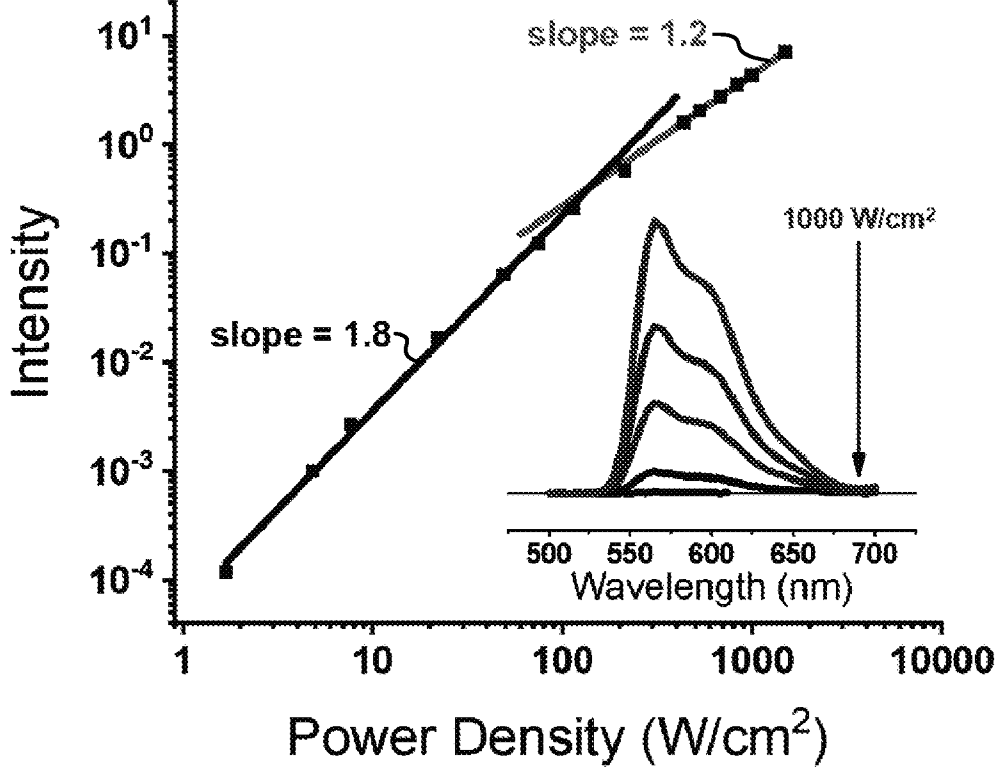
FIG. 14 is graph of power dependence of the upconverted fluorescence detected at 585 nm under variable intensity 685 nm illumination for an embodiment of a photon upconversion system of the present disclosure. The sample exhibited a crossover point from nearly-quadratic to nearly-linear power dependence at roughly 150 $W/cm^2$.

The power dependence of the upconverted rubrene fluorescence shown in FIG. 14 was measured in the presence of thiosquaraine as a function of 685 nm incident optical power density. The luminescence intensity of the upconversion sample exhibits a quadratic power dependence below roughly 150 W/cm$^2$ optical power density, where a crossover point into the strong annihilation limit is evident in the double-logarithmic plot in FIG. 14. While the strong annihilation region represents the range of input laser fluences wherein the upconversion process is the most efficient, upconverted fluorescence was observed when the sample is excited by a solar simulator with a 650 nm longpass filter on the output.

For facile integration into a solid-state photovoltaic device, it is generally ideal that the upconversion system be active in a thin-film architecture. TTA upconversion relies on Dexter energy transfer, which fundamentally operates via an electron exchange mechanism. Therefore, TTA upconversion requires some degree of direct orbital overlap among the relevant chromophores. In practical terms, this means that a thin-film composite that supports TTA upconversion must accommodate molecular mobility so that the collisional events necessary for the electron exchange process can occur. Therefore, most strategies for transferring an upconversion system to the solid-state involve dispersion within an elastic polymer matrix. Several such materials, including polyurethanes, polyacrylates, and ethylene oxide-epichlorohydrin (EO-EPI) copolymers, have been investigated previously as hosts for solid-state upconversion systems. Here, an EO-EPI copolymer was selected as a host matrix for the thiosquaraine/rubrene system based on chemical compatibility and film processing considerations. A representative absorption spectrum of the resulting upconversion film is displayed in FIG. 15A. Solid-state photon upconversion was readily apparent from the thin-film sample following illumination of the thiosquaraine component with 685 nm laser diode. The spectrum of the thin-film upconversion emission was reported in FIG. 15B. This spectrum was measured with a 650 nm shortpass filter following the sample and before the detector. Due to the slightly scattering nature of the thin-film sample and the nominal 10 nm FWHM bandwidth of the excitation beam, a slight shoulder appeared on the red edge of the thin-film upconversion profile, which was due to scattering of the laser diode. The solid-state luminescence from this thin-film upconversion platform was intense enough to be readily observed by eye, even in an aerobic environment, conditions in which one might initially anticipate oxygen quenching. Nevertheless, strong red-to-yellow photon upconversion in air for these completely heavy atom-free thin-films was observed.

Herein is presented a successful TTA photon upconversion platform that utilized a molecular, heavy atom-free, thionated squaraine dye sensitizer that was capable of promoting intense thin-film upconversion luminescence, even under aerobic conditions. Given the broad electronic diversity that was accessible through chemical functionalization of the squaraine platform, devices based on this thin-film demonstration can gain viability as a model testbed for developing metal-free organic sensitizers for solar upconversion applications.

The highly-tunable squaraine motif can be modified to push the absorption well into the near-infrared (NIR). For solar applications, the ideal triplet sensitizers would absorb in the deep red to NIR, as this region of the solar spectrum is poorly utilized by traditional semiconductor materials used in photovoltaics and emerging thin-film materials such as organometal halide perovskites. In comparison to the system herein, some success has also been achieved using thionation to increase the intersystem crossing efficiency of perylene diimides (PDI). The PDI absorption can be shifted into the NIR by extending the size of the fused ring system. However, this massive π-extension can lead to substantial aggregation and severe materials processing challenges. While adding sterically-blocking bulky substituents is an effective strategy for circumventing this problem, such modifications are unattractive for TTA upconversion due to the orbital overlap and molecular collisions that are required for the Dexter energy transfer process to occur, particularly in a thin-film architecture. On the other hand, the squaraine absorption features are predominately achieved by the push-pull nature of its intramolecular charge-transfer type transitions. As such, achieving NIR absorption with a functionalized squaraine sensitizer need not negatively impact its processing. Correspondingly, the thiosquaraines of the present disclosure can be used to implement NIR photon upconversion in multiple potential applications, from photodetectors and solar cells to imaging and sensing.

Additional information on the upconversion quantum yield calculation, photoinduced absorption spectra, additional global analysis, modulation dependence, stability tests and materials characterization are provided below.

Upconversion Quantum Yield Measurements:

The photon upconversion quantum yield, $\Phi_{UC}$, was determined using the established relationship for relative emission quantum yield expressed in Eq. 3.

$$\Phi_{UC} = \Phi_{std}\frac{E}{A}\frac{A_{std}}{E_{std}}\frac{\eta^2}{\eta_{std}^2} \quad \text{(Eq. 3)}$$

Figure 16:
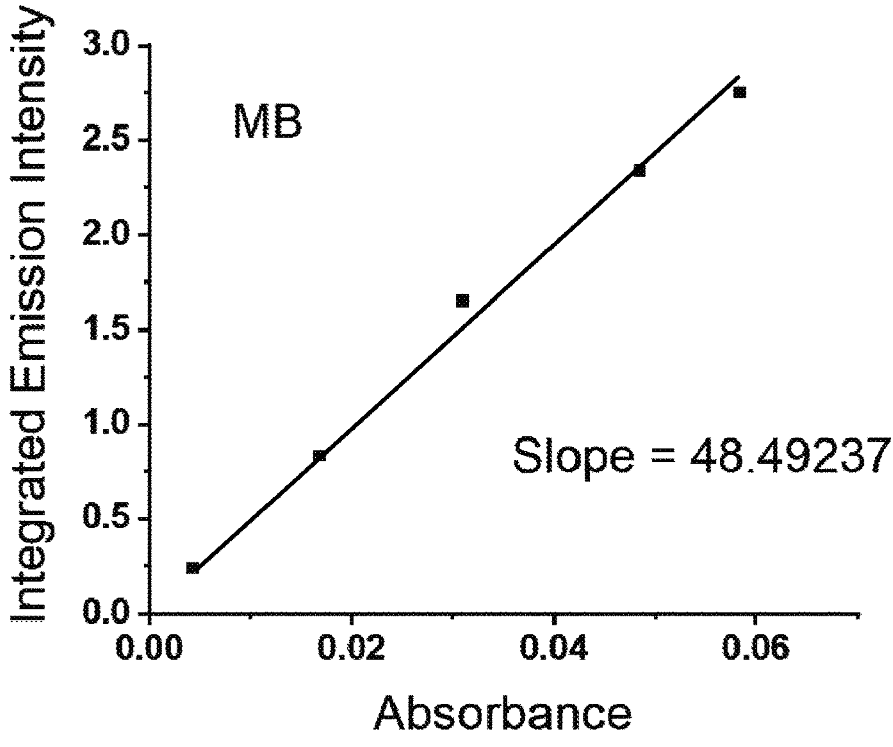
FIG. 16 is a plot of absorbance vs. emission plot of methylene blue (MB) quantum yield standard, the slope of which was used in Equation 3 for calculating the relative quantum yield.

Here $\Phi_{UC}$ is the unknown upconversion yield that is to be determined relative to the fluorescence quantum yield of a standard sample, $\Phi_{std}$, under predetermined conditions, E, A, and η represent, respectively, the integrated emission, the optical density at the excitation wavelength, and the refractive index for the upconversion sample (no subscript) and the standard sample ("std" subscript). In this case, the standard used was methylene blue, which has a quantum yield of 0.091 in ethanol. The value of $\Phi_{std}$ for the methylene blue standard was confirmed through direct measurement in an integrating sphere under the measurement conditions. In order to reduce error in the relative determination of the $\Phi_{UC}$ value, methylene blue's absorption and emission were measured at various concentrations ranging from 1.3-13.3 μM. The slope from the linear regression of the integrated emission intensity vs. absorption at 685 nm (FIG. 16) was used in place of $A_{std}/E_{std}$. The absorption and emission of the upconversion system were measured in deaerated toluene.

Since TTA upconversion is a 2-to-1 photon process, the maximum quantum yield of photons in vs. photons out is 0.5 (50%). In some cases, when Eq. 3 is used for upconversion quantum efficiency measurements, a factor of 2 is added to report the upconversion quantum efficiency out of 100%. The number is reported herein as is out of 50%, but in an adjusted quantum efficiency calculation with a maximum of 100% the quantum yield is 0.03 (3%).

Example 2. Red-To-Blue Triplet-Triplet Annihilation Upconversion with a Heavy-Atom-Free Thiosquaraine Sensitizer Photon upconversion is a photophysical process that produces higher energy photons from lower energy photons. Triplet-triplet annihilation (TTA) or triplet fusion is a mechanism of upconversion in which a sensitizer molecule is excited, undergoes intersystem crossing to the triplet state, and subsequently undergoes triplet-triplet energy transfer (TTET) to an acceptor molecule. Two acceptor triplets can then annihilate, deactivating one to the ground state and promoting one to an excited singlet state in an overall spin-allowed process. This excited singlet then fluoresces at an energy higher than the incident photon excitation. TTA photon upconversion has potential applications in photovoltaics, photocatalysis, bioimaging, and sensing.

One important factor that determines whether a TTA upconversion system is suitable for a given application is the anti-Stokes shift, or the energy difference between the excitation and upconverted emission wavelengths. In photovoltaics, photons are upconverted to the band edge of the active material, and any additional energy is lost through thermalization (SQ ref). However, in applications such as photocatalysis to generate solar fuels, high energy blue or ultraviolet photons are often needed to drive the photochemical reactions. In this respect, larger anti-Stokes shifts are preferable, with TTA upconversion providing the opportunity to drive these reactions with lower energy photons prevalent in incident solar flux.

Larger anti-Stokes shifts are preferable for applications such as solar-driven photocatalysis, where TTA could provide the opportunity to use low energy photons rather than the high energy blue or ultraviolet photons these photochemical reactions often require. However, upconversion systems with large anti-Stokes shifts typically have the trade-off of low upconversion efficiencies, resulting from the energy losses in the various energy transfer steps entailed in TTA upconversion. Many studies have focused on reducing the sensitizer singlet-triplet energy loss to optimize the anti-Stokes shift, but it is also important to be mindful of the energy difference between the sensitizer and emitter triplet energies. Too large of an energy difference is a large energy loss in the upconversion process, but too small of an energy difference or an inverted energy difference will cause the triplet energy transfer to occur by an entropic rather than enthalpic driving force.

Figure 17:
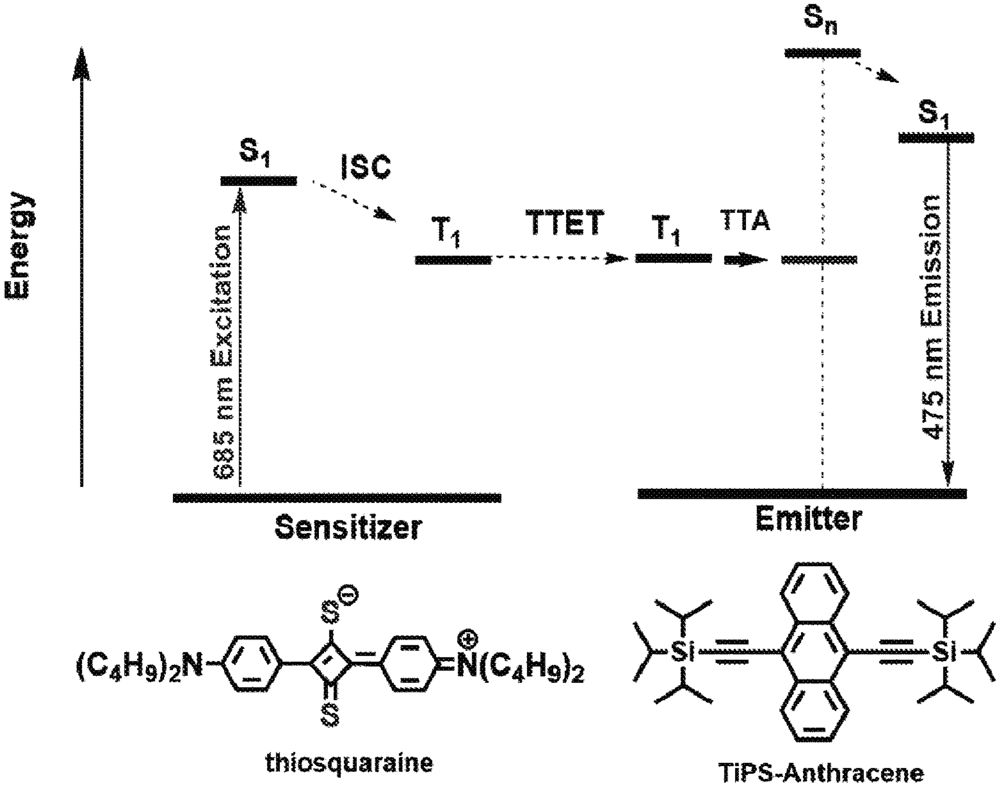
FIG. 17 is a schematic representation of an embodiment of a triplet-triplet annihilation (TTA) upconversion mechanism. The excitation wavelength of an embodiment of a photon upconversion system was 685 nm. The peak of the upconverted emission was at 475 nm. The chemical structures of embodiments of the sensitizer and the emitter of the present disclosure are shown.

Most traditional TTA photon upconversion systems have relied on heavy metal complexes or heavy atoms to induce the necessary spin orbit coupling in the sensitizer molecules. The inclusion of these heavy metals makes the systems costly and provides a barrier to widespread application. Described in Example 1 is an all-organic TTA upconversion system utilizing a thionated squaraine dye as the sensitizer. Inclusion of sulfur on the squaraine core reorders the lowest energy singlet states, opening a channel for intersystem crossing. Here an increased anti-Stokes shift for the thiosquaraine upconversion system is shown, by demonstrating red-to-blue upconversion from the thiosquaraine to TiPS-anthracene (FIG. 17). This system had an excitation-to-peak-emission anti-Stokes shift of 0.94 eV at the deepest red excitation, which is believed to have the largest anti-Stokes shift reported in a heavy-atom-free system to date. In fact, this system is one of the few examples where <700 nm excitation can be used to produce <500 nm emission.

This emitter had a triplet energy ≥1.41 eV, which was 120 meV greater than the calculated thiosquaraine triplet energies. Thus, this increased anti-Stokes shift pushed the energetic limits of the thiosquaraine system and appeared to involve an endothermic triplet-triplet energy transfer process that could be thermally activated. This study provides a better understanding of the energetic landscape of the thiosquaraine sensitizer, which allows for advantageous pairings with annihilator molecules.

Figure 18:
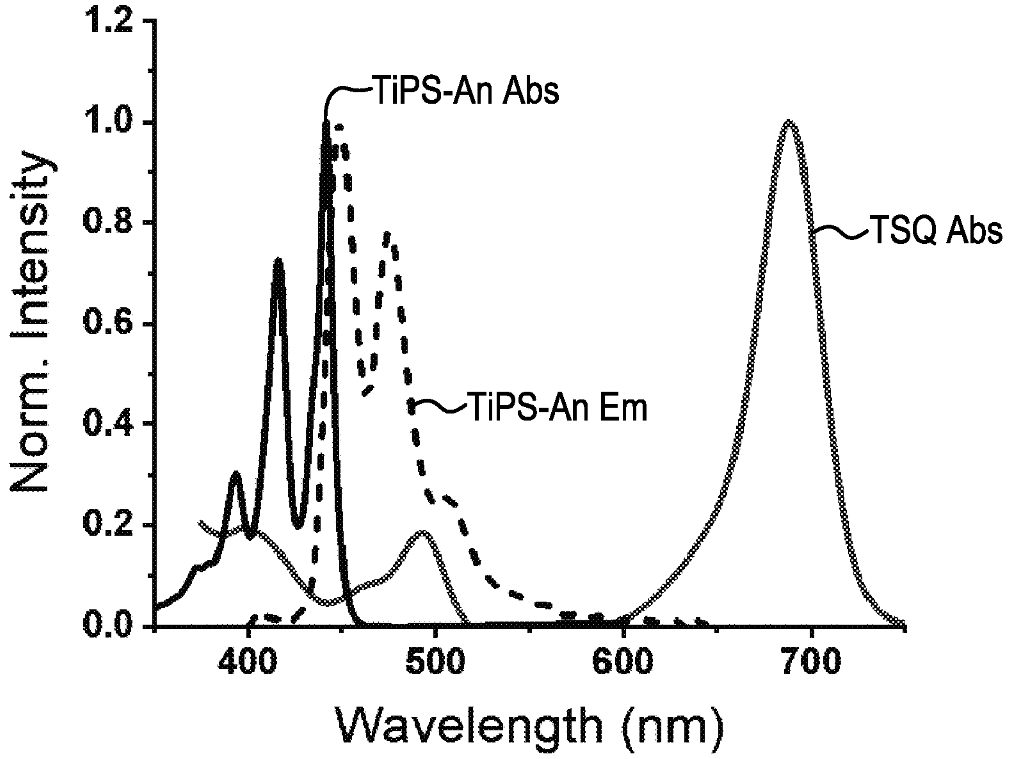
FIG. 18 an absorption and emission spectrum of an embodiment of an emitter of the present disclosure (TiPS-anthracene) compared with the absorption spectrum of an embodiment of the sensitizer of the present disclosure.

Referring to FIG. 18, the thiosquaraine (TSQ) sensitizer exhibits an intense absorption band ($1.57\times10^5$ $M^{-1}$ $cm^{-1}$) in the deep red at 685 nm. Example 1 demonstrated efficient triplet energy transfer from the thiosquaraine sensitizer to rubrene, which emits yellow ($\lambda_{max}$=570 nm). When selecting an emitter to extend the anti-Stokes shift of the upconverted emission, 9,10-bis[(triisopropylsilyl)ethynyl]anthracene (TiPS-Anthracene or TiPS-An) was chosen. TiPS-An has an emission max at 450 nm in dilute solution, so it was a good candidate to increase the anti-Stokes shift of the thiosquaraine system.

Additionally, since no phosphorescence is observed from the TSQ to determine the triplet energy, TiPS-An could serve as a potential upper bound for exploring the energetics of the thiosquaraine triplet. The triplet energy of TiPS-An ($E_T$≥1.41 eV) was sufficiently above that of rubrene ($E_T$=1.12 eV), to merit exploration.

Figure 19:
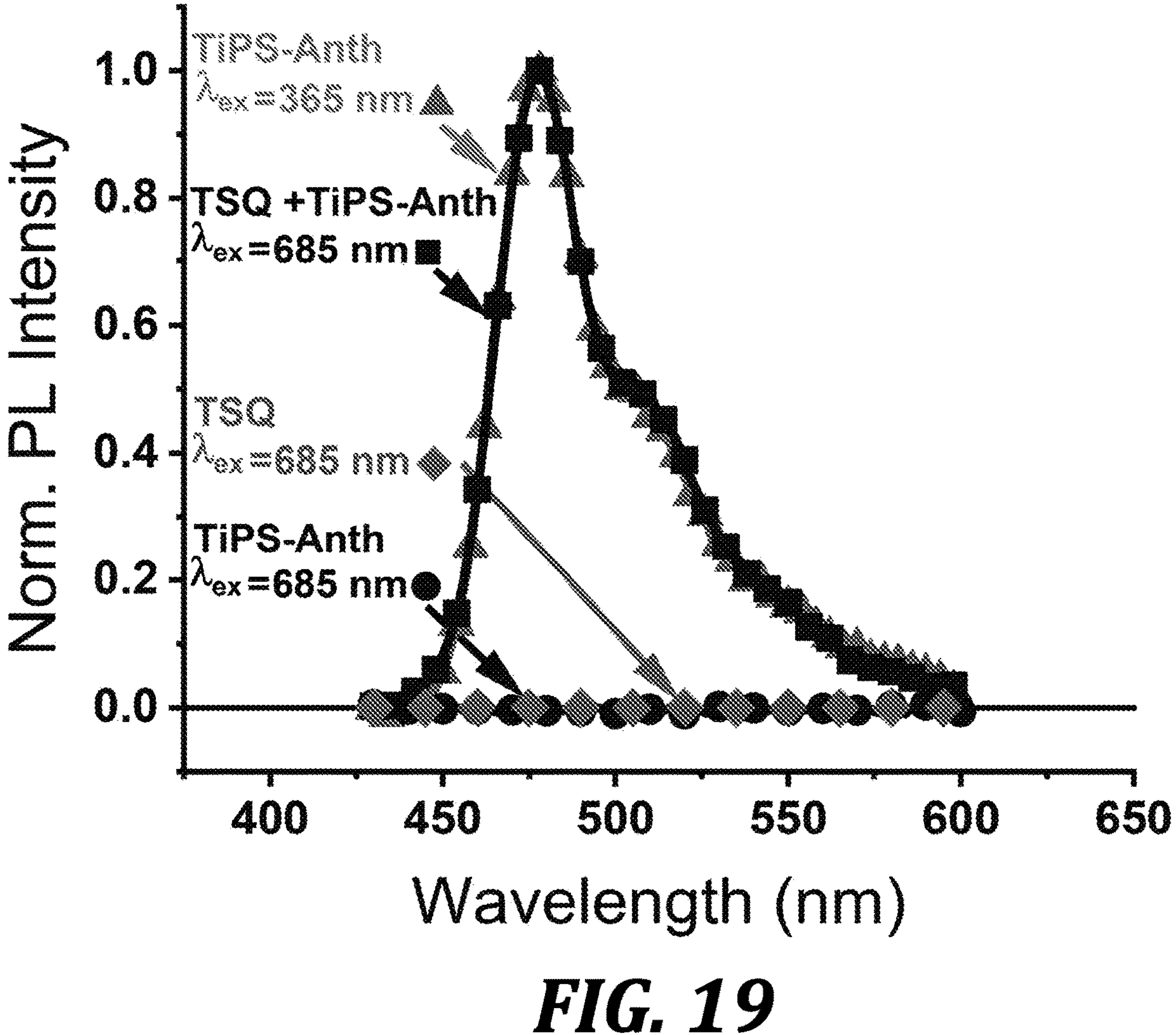
FIG. 19 is a photoluminescence spectrum of selective excitation of an embodiment of a thiosquaraine sensitizer at 685 nm leading to upconverted fluorescence from an embodiment of an emitter component (rubrene). This fluorescence was the same to the fluorescence observed when TiPS-An is excited at 365 nm. No fluorescence was observed from either individual molecule when excited in isolation at $\lambda_{ex}$=685 nm.

FIG. 19 shows that selectively exciting the thiosquaraine molecule at 685 nm in solution with TiPS-An results in upconverted fluorescence that is spectrally indistinguishable from the native TiPS-An singlet emission ($\lambda_{ex}$=365 nm) at the same concentration. The anti-Stokes shift was calculated to be 0.65 eV, an increase of 0.38 eV over the system of Example 1, based on intensity-weighted averages of the upconverted emission and sensitizer absorption spectra. This method of calculating the anti-Stokes shift was used in an effort to standardize these measurements across the field of TTA upconversion. However, it is worth noting that there are still considerable variations in the method used to calculate the anti-Stokes shift, resulting in inconsistent reporting. For example, if a peak-to-peak upconversion margin the anti-Stokes shift between the absorption peak ($\lambda_{ex}$=685 nm) and the emission peak ($\lambda_{em}$=475 nm) was used, the anti-Stokes shift would be 0.80 eV. If the deepest red excitation ($\lambda_{ex}$=740 nm) and the emission max ($\lambda_{em}$=475 nm) are used, the anti-Stokes shift increased to 0.94 eV, which is on par with the highest reported anti-Stokes shifts in metal complex-containing upconversion systems and is believed to be higher than any anti-Stokes shifts observed for heavy-atom-free systems. In fact, this is one of very few examples of >700 nm excitation resulting in <500 nm emission.

FIG. 19 also shows that no spectral features were observed when excited at 685 nm unless both components were present in solution. This lack of emission was important because it demonstrated that the upconverted TiPS-An luminescence was in no way due to two-photon absorption on TiPS-An at the illumination intensities used in this study. Blue upconverted emission resulting from the red excitation was observed.

As is typical of TTA upconversion systems, the upconverted fluorescence exhibited significantly different kinetics than that of the native emitter fluorescence. In the upconversion sample, a decay constant of 98 μs was observed for the TiPS-An centered fluorescence. TiPS-An had a reported decay constant of 6.6 ns, but at high concentrations such as those used in this study, the fluorescence lifetime was extended due to self-absorption effects. The upconverted TiPS-An fluorescence exhibited a slow rise time in comparison to the nearly instant rise observed in Example 1. The rise time of the upconverted TiPS-An fluorescence fitted to about 19 μs, which was nearly the lifetime of the thiosquaraine triplet (20 μs). This provided further evidence that the triplet energy transfer was slow, potentially due to the energetic barrier.

Figure 20A:
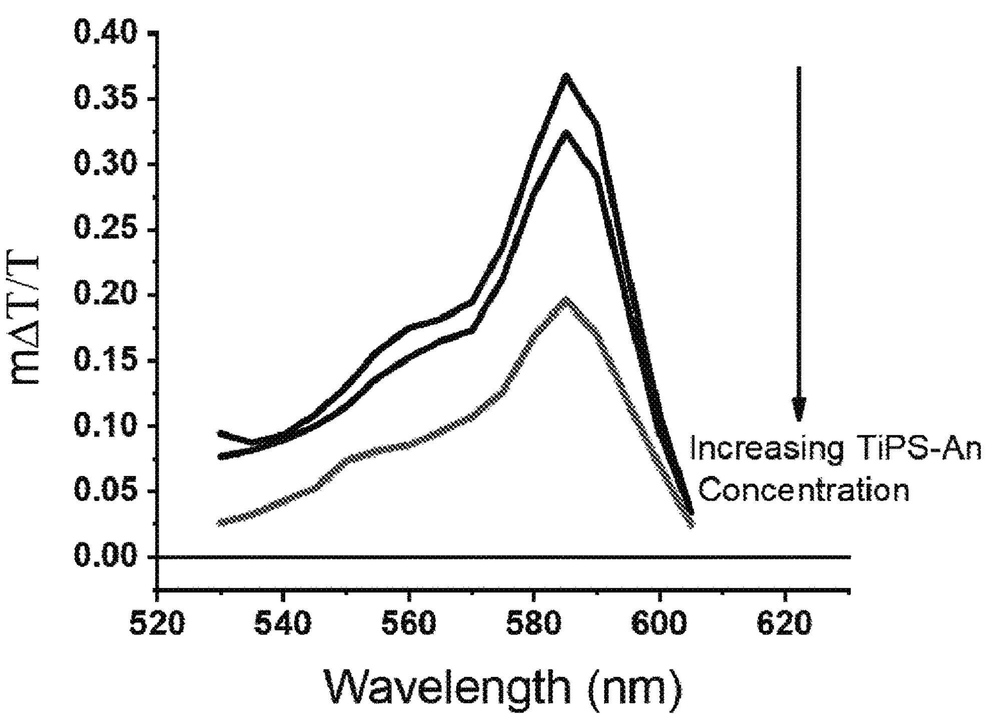
FIG. 20A is a quasi-steady-state photoinduced absorption (PIA) spectra of an embodiment of a sensitizer triplet of the present disclosure (thiosquaraine triplet, $^3$TSQ) at varying emitter (TiPS-An) concentrations. Large concentrations (gray trace) showed minimal quenching of the $^3$TSQ feature. More significant quenching was observed at the solubility limit, however, the photoluminescence data.
Figure 20B:
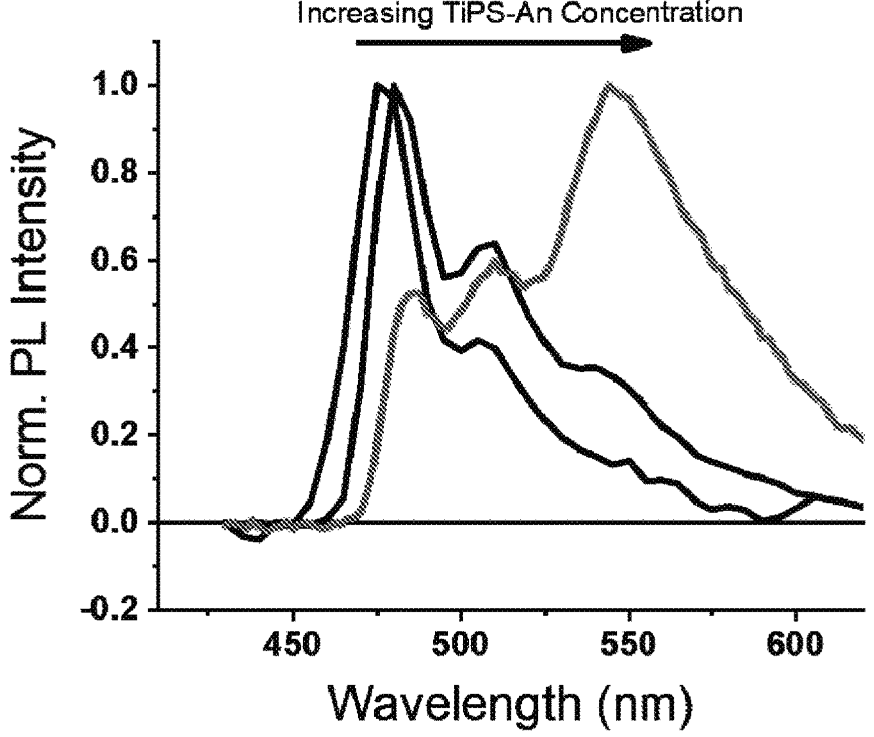
FIG. 20B is a series of photoluminescence spectra showing that at increasing concentration the acceptor aggregated, and the energetic landscape changed.
Figure 20C:
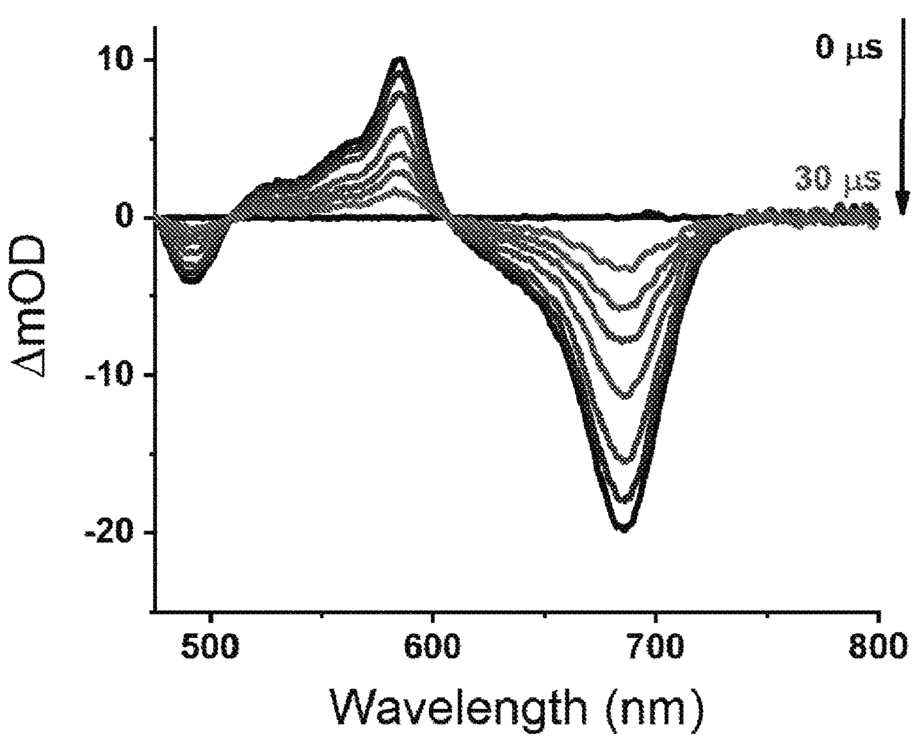
FIG. 20C is a transient absorption spectra of an embodiment of a sensitizer of the present disclosure (a thiosquaraine) in the presence of an embodiment of emitter of the present disclosure (TiPS-An).
Figure 20D:
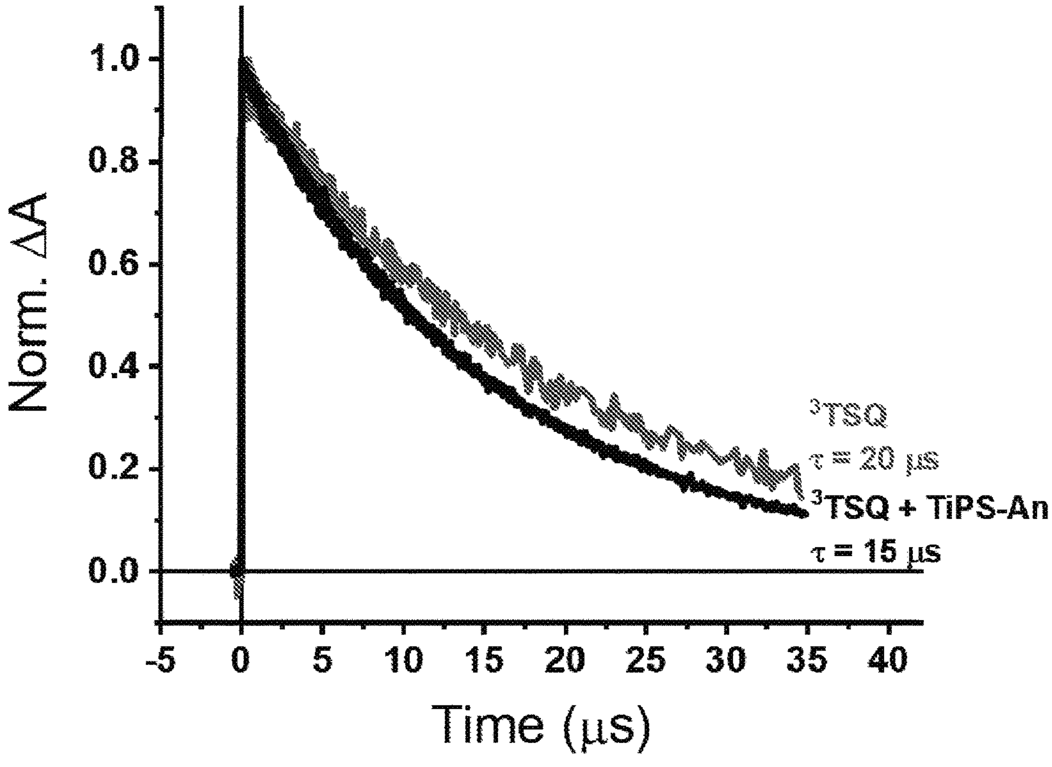
FIG. 20D is a graph showing kinetic traces of the triplet absorption with and without the emitter of FIG. 20C (TiPS-An), showing minimal quenching of the triplet lifetime due to the presence of TiPS-An.

Both time-resolved (transient absorption) and quasi-steady state (photoinduced absorption) measurements were undertaken to quantitatively study the extent of quenching of the TSQ triplet by the addition of TiPS-An. Both measurements showed that the quenching efficiency was diminished compared to the TSQ/rubrene system ($k_Q$=$1.4\times10^9$ $M^{-1}$ $s^{-1}$), where the acceptor triplet energy was lower. In the quasi-steady state measurement, the intensity of the $^3$TSQ feature was only marginally diminished, even when large concentrations (~20 mM) of acceptor are used (FIG. 20A). Significant quenching was only observed at the solubility limit of the molecule, where photoluminescence data indicated that aggregation had caused a bathochromic shift in the excited state energy. At this concentration, the luminescence maximum shifted from 475 nm to 550 nm and the luminescence spectrum was broadened, as shown in FIG. 20B. The time-resolved data also indicated a diminished quenching efficiency. Again, at large concentrations of acceptor, only a small amount of quenching was seen in the $^3$TSQ lifetime, with the lifetime decreasing only to 15 μs from the 20 μs native triplet lifetime (FIGS. 20C and 20D). If, in fact, the TiPS-An triplet energy was above that of the TSQ triplet energy, it was possible that the quenching was masked by reverse triplet-triplet energy transfer processes. No evidence for reverse triplet-triplet energy transfer was observed in the transient absorption.

Figure 21A:
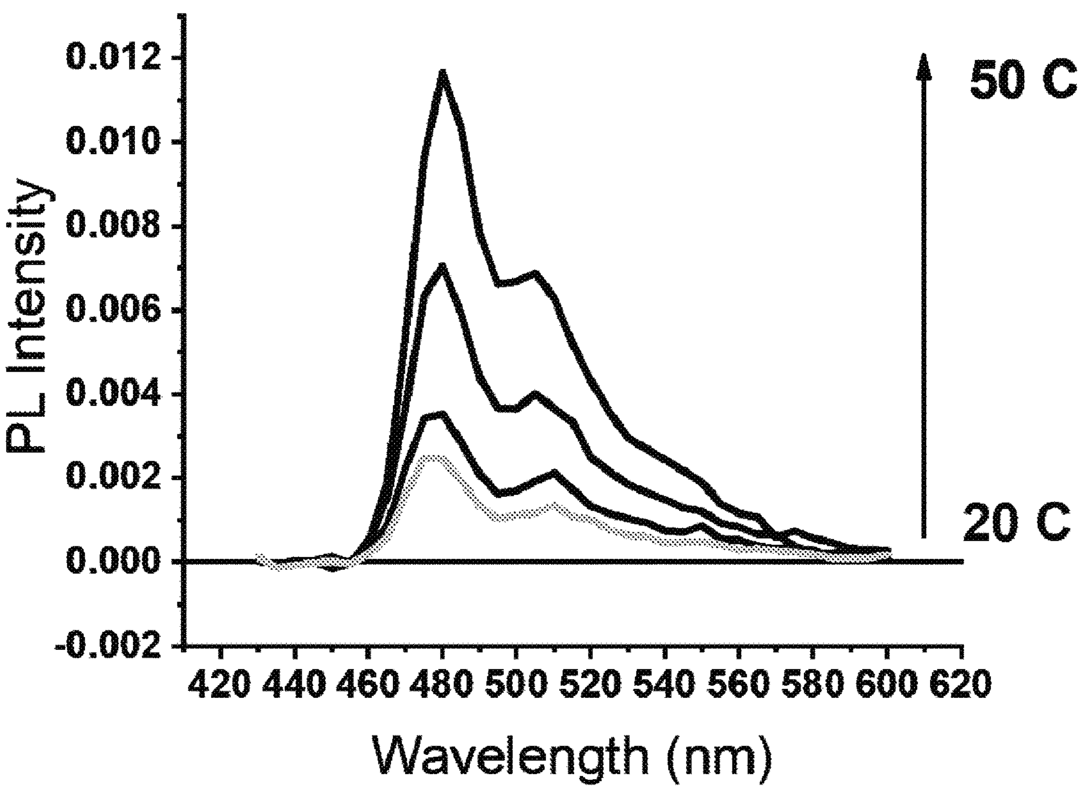
FIG. 21A is a series of photoluminescence spectra showing temperature dependent luminescence traces for an embodiment of thiosquaraine sensitizer and an embodiment of a TiPS-An emitter upconversion system. As the temperature increases from 20° C. to 50° C., the luminescence intensity increased by nearly an order of magnitude.
Figure 21B:
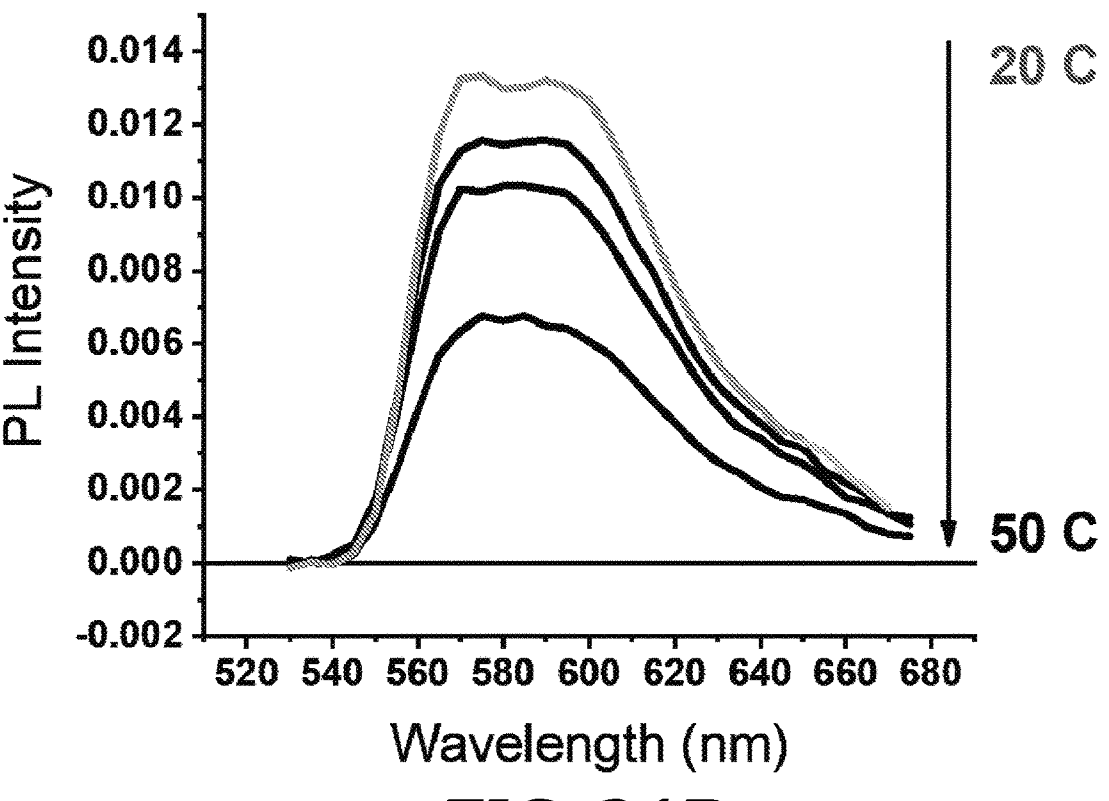
FIG. 21B is a series of photoluminescence spectra showing the temperature dependent luminescence traces for an embodiment of thiosquaraine sensitizer and an embodiment of a rubrene emitter upconversion system. This system shows opposite behavior from the TSQ/TiPS-An system of FIG. 21A. As the temperature increased from 20° C. to 50° C., the luminescence intensity decreases.

To explore whether the triplet-triplet energy transfer process was indeed endothermic between TSQ and TiPS-An, the temperature dependence of the upconverted emission was measured. Over a range of 20° C. to 50° C., the TiPS-An upconverted emission increased in intensity with increasing temperature (FIG. 21A). This was in contrast with the rubrene upconversion intensity, which decreased with increasing temperature over the same range (FIG. 21B). This data indicated that the increased temperature facilitated additional triplet-triplet energy transfer between the TSQ and TiPS-An through thermal population, and this process outcompeted the increased non-radiative decay channels opened through the temperature increase.

Figure 22:
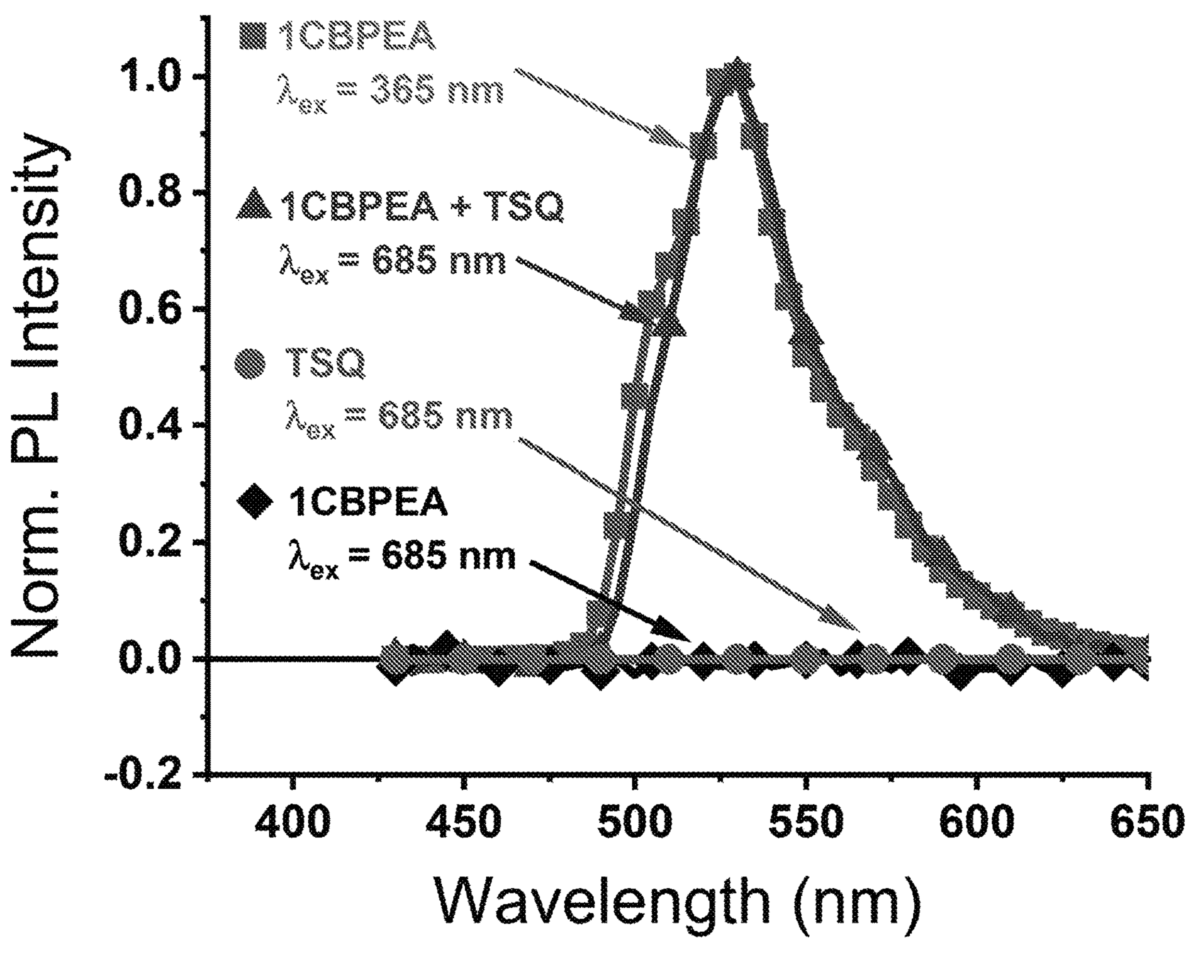
FIG. 22 is a photoluminescence spectra of a photon upconversion system including an embodiment of a sensitizer of the present disclosure with a 1CBPEA emitter.

Thus, TiPS-Anthracene gives insight into the energetic landscape of the thiosquaraine, and sets a bound for the energetic shifts possible with this system. Furthermore, since red-to-blue is achievable, red-to-green photon upconversion systems are possible as well, and can be demonstrated, for example, with 1CBPEA, as shown in FIG. 22.

By example and without limitation, embodiments are disclosed according to the following enumerated paragraphs:

A1. A photon upconversion system, comprising:

a sensitizer having a structure of Formula (I)

(I)

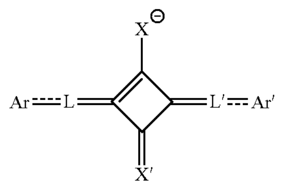

wherein:

X and X' are each independently selected from O, S, Se, and Te,

L is $(CRR')_n$, wherein:

R at each occurrence is independently H, halogen, $C_{1-10}$ alkyl, or $C_{1-10}$ haloalkyl, R' at each occurrence is absent, or independently H, halogen, $C_{1-10}$ alkyl, or $C_{1-10}$ haloalkyl, and n is an integer selected from 0, 1, 2, or 3:

L' is absent, or $(CR)_m$—$(CRR')_p$, wherein

R at each occurrence is independently H, halogen, $C_{1-10}$ alkyl, or $C_{1-10}$ haloalkyl, R' at each occurrence is absent, or independently H, halogen, $C_{1-10}$ alkyl, or $C_{1-10}$ haloalkyl, and m is 1; and p is an integer selected from 0, 1, or 2; and Ar and Ar' are each independently selected from aryl and heteroaryl, wherein said aryl and heteroaryl are each optionally substituted with 1, 2, 3, or 4 substituents independently selected from amino, $C_{1-10}$ alkyl, aryl, halo, OH, wherein each of said amino, $C_{1-10}$ alkyl, and aryl is optionally substituted with 1, 2, 3, or 4 substituents independently selected from amino, halo, $C_{1-10}$ alkyl, $C_{1-6}$ haloalkyl, and OH; wherein one of Ar and Ar' is positively charged; and an emitter, wherein the sensitizer absorbs an energy from an incident radiation, and the emitter accepts the energy from the sensitizer via triplet-triplet energy transfer, and emits at a lower wavelength than the incident radiation via a triplet-triplet annihilation process.

A2. The photon upconversion system of Paragraph A1, wherein the photon upconversion system does not comprise heavy atoms.

A3. The photon upconversion system of Paragraph A1, wherein the photon upconversion system is metal-free.

A4. The photon upconversion system of any one of the preceding Paragraphs, wherein the photon upconversion system does not comprise halogen atoms.

A5. The photon upconversion system of any one of the preceding Paragraphs, wherein the emitter comprises a triplet energy level within at least about 0.13 eV, at room temperature, of a triplet energy level of the sensitizer.

A6. The photon upconversion system of any one of the preceding Paragraphs, wherein the emitter comprises a triplet energy level within at least about 5 kT of a triplet energy level of the sensitizer.

A7. The photon upconversion system of any one of the preceding Paragraphs, wherein the sensitizer has a full width at half maximum absorption of 40 nm or less.

A8. The photon upconversion system of any one of the preceding Paragraphs, wherein the sensitizer absorbs less than 10% of the emitter's absorption spectrum.

A9. The photon upconversion system of any one of the preceding Paragraphs, wherein the incident radiation is non-coherent.

A10. The photon upconversion system of any one of Paragraphs A1 to A8, wherein the incident radiation is coherent.

A11. The photon upconversion system of any one of the preceding Paragraphs, wherein the triplet-triplet energy transfer comprises a bimolecular Dexter energy transfer process.

A12. The photon upconversion system of any one of the preceding Paragraphs, wherein the photon upconversion system comprises an anti-Stokes shift of 0.1 eV or more.

A13. The photon upconversion system of any one of the preceding Paragraphs, further comprising a triplet-triplet upconversion quantum efficiency of more than 0% and/or less than or equal to 50%.

A14. The photon upconversion system of any one of the preceding Paragraphs, wherein X and X' are each independently S or O.

A15. The photon upconversion system of any one of the preceding Paragraphs, wherein X and X' are each S.

A16. The photon upconversion system of any one of the preceding Paragraphs, wherein L is $(CRR')_n$, wherein:

R at each occurrence is independently H or $C_{1-10}$ alkyl,

R' at each occurrence is absent, or independently H or $C_{1-10}$ alkyl, and n is an integer selected from 0 and 1.

A17. The photon upconversion system of any one of the preceding Paragraphs, wherein L' is absent, or $(CR)_m$—$(CRR')_p$, wherein R at each occurrence is independently H or $C_{1-10}$ alkyl, R' at each occurrence is absent, or independently H or $C_{1-10}$ alkyl;

m is 1; and p is an integer selected from 0 and 1.

A18. The photon upconversion system of any one of the preceding Paragraphs, wherein Ar and Ar' are each independently selected from aryl and heteroaryl, wherein said aryl and heteroaryl are each optionally substituted with 1, 2, 3, or 4 substituents independently selected from $C_{1-10}$ alkyl, a primary amino, $C_{1-10}$ alkylamino, and a di($C_{1-10}$ alkyl)amino.

A19. The photon upconversion system of any one of the preceding Paragraphs, wherein Ar and Ar' are each independently selected from a benzyl, anthracyl, pyrenyl, azulenyl, pyridinyl, imidazolyl, carbazolyl, pyrrolyl, thiophenyl, quinolinyl, indolyl, benzindolyl, acridinyl, thiazolyl, benzothiazolyl, selenazolyl, and benzoselenazolyl, each optionally substituted with 1, 2, 3, or 4 substituents independently selected from amino, $C_{1-10}$ alkyl, aryl, halo, OH, wherein each of said amino, alkyl, and aryl is optionally substituted with 1, 2, 3, or 4 substituents independently selected from amino, halo, and OH.

A20. The photon upconversion system of any one of the preceding Paragraphs, wherein the sensitizer is selected from:

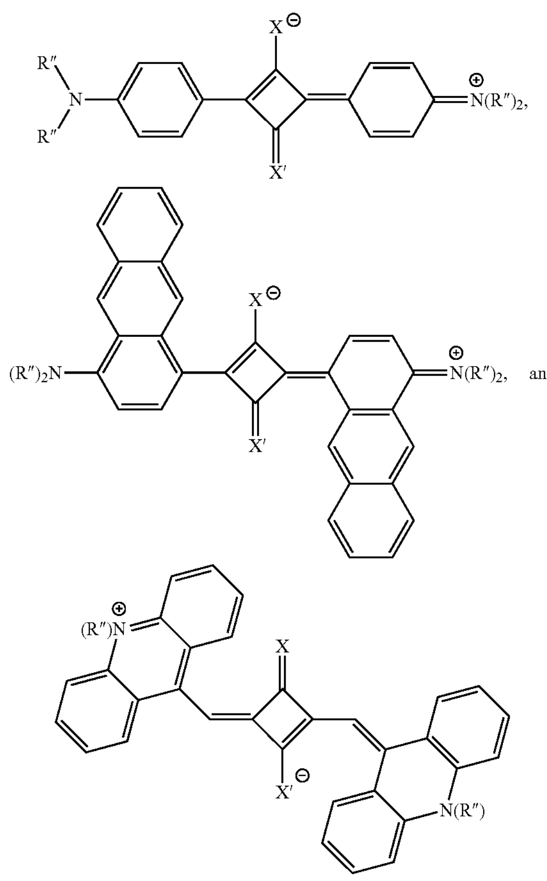

wherein R" at each occurrence is independently $C_{1-10}$ alkyl; and

X and X' are each independently selected from S and O.

A21. The photon upconversion system of any one of the preceding Paragraphs, wherein sensitizer comprises a symmetric structure (e.g., C2-symmetric).

A22. The photon upconversion system of any one of the preceding Paragraphs, wherein the emitter is selected from rubrene, TiPS-anthracene, 1-chloro-9,10-bis(phenylethynyl)anthracene, 2-chloro-9,10-bis(phenylethynyl)anthracene, and violanthrone-79.

A23. The photon upconversion system of any one of the preceding Paragraphs, wherein the emitter does not comprise a boron-containing compound.

A24. A device, comprising the photon upconversion system of any one of preceding Paragraphs.

A25. The device of Paragraph A24, wherein the device is selected from a photovoltaic device, a solar luminescent concentrator, a photocatalytic device, a sensor, a bioimaging material, and an anti-counterfeit system.

A26. The device of Paragraphs A24 or A25, wherein the photon upconversion system is in the form of a coating.

A27. The device of any one of Paragraphs A21 to A23, wherein the photon upconversion system is incorporated within a polymer.

A28. The device of Paragraph A27, wherein the polymer comprises an elastomer.

A29. The device of any one of Paragraphs A24 to A28, wherein the device is further coupled to a solar cell.

A30. The device of any one of Paragraphs A24 to A29, wherein the device comprises:

a current collector;

an organic photovoltaic layer;

a semi-transparent collector;

an upconversion layer; and a back reflector.

A31. The device of Paragraph A30, wherein the current collector is transparent to incident light.

A32. The device of Paragraph A30 or Paragraph A31, wherein the organic photovoltaic layer absorbs incident light having an energy level greater than band gap energy of the organic photovoltaic layer.

A33. The device of any one of Paragraphs A30 to A32, wherein the upconversion layer absorbs incident light having an energy of less than the band gap energy of the organic photovoltaic layer.

While illustrative embodiments have been illustrated and described, it will be appreciated that various changes can be made therein without departing from the spirit and scope of the invention.

The invention claimed is:

1. A photon upconversion system, comprising:

a sensitizer having a structure of Formula (I)

(I)

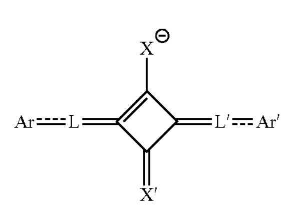

wherein:

X and X' are each independently selected from S, Se, and Te,

L is (CRR')n, wherein:

R at each occurrence is independently H, halogen, C1-10 alkyl, or C1-10 haloalkyl, R' at each occurrence is absent, or independently H, halogen, C1-10 alkyl, or C1-10 haloalkyl, and n is an integer selected from 0, 1, 2, or 3;

L' is absent, or (CR)m-(CRR')p, wherein

R at each occurrence is independently H, halogen, C1-10 alkyl, or C1-10 haloalkyl, R' at each occurrence is absent, or independently H, halogen, C1-10 alkyl, or C1-10 haloalkyl, and m is 1; and p is an integer selected from 0, 1, or 2; and Ar and Ar' are each independently selected from aryl and heteroaryl, wherein said aryl and heteroaryl are each optionally substituted with 1, 2, 3, or 4 substituents independently selected from amino, C1-10 alkyl, aryl, halo, OH, wherein each of said amino, C1-10 alkyl, and aryl is optionally substituted with 1, 2, 3, or 4 substituents independently selected from amino, halo, C1-10 alkyl, C1-6 haloalkyl, and OH; wherein one of Ar and Ar' is positively charged; and an emitter, wherein the sensitizer absorbs an energy from an incident radiation, and the emitter accepts the energy from the sensitizer via triplet-triplet energy transfer, and emits at a lower wavelength than the incident radiation via a triplet-triplet annihilation process.

2. The photon upconversion system of claim 1, wherein the photon upconversion system does not comprise heavy atoms.

3. The photon upconversion system of claim 1, wherein the photon upconversion system is metal-free.

4. The photon upconversion system of claim 1, wherein the photon upconversion system does not comprise halogen atoms.

5. The photon upconversion system of claim 1, wherein the emitter comprises a triplet energy level within at least about 0.13 eV, at room temperature, of a triplet energy level of the sensitizer.

6. The photon upconversion system of claim 1, wherein the emitter comprises a triplet energy level within at least about 5 kT of a triplet energy level of the sensitizer.

7. The photon upconversion system of claim 1, wherein the sensitizer has a full width at half maximum absorption of 40 nm or less.

8. The photon upconversion system of claim 1, wherein the triplet-triplet energy transfer comprises a bimolecular Dexter energy transfer process.

9. The photon upconversion system of claim 1, wherein the photon upconversion system comprises an anti-Stokes shift of 0.1 eV or more.

10. The photon upconversion system of claim 1, further comprising a triplet-triplet upconversion quantum efficiency of more than 0% and/or less than or equal to 50%.

11. The photon upconversion system of claim 1, wherein X and X' are each S.

12. The photon upconversion system of claim 1, wherein L is (CRR')n, wherein:

R at each occurrence is independently H or C1-10 alkyl,

R' at each occurrence is absent, or independently H or C1-10 alkyl, and n is an integer selected from 0 and 1.

13. The photon upconversion system of claim 1, wherein L' is absent, or (CR)m-(CRR')p, wherein R at each occurrence is independently H or C1-10 alkyl, R' at each occurrence is absent, or independently H or C1-10 alkyl;

m is 1; and p is an integer selected from 0 and 1.

14. The photon upconversion system of claim 1, wherein Ar and Ar' are each independently selected from aryl and heteroaryl, wherein said aryl and heteroaryl are each optionally substituted with 1, 2, 3, or 4 substituents independently selected from C1-10 alkyl, a primary amino, C1-10 alkylamino, and a di(C1-10 alkyl)amino.

15. The photon upconversion system of claim 1, wherein Ar and Ar' are each independently selected from a benzyl, anthracyl, pyrenyl, azulenyl, pyridinyl, imidazolyl, carbazolyl, pyrrolyl, thiophenyl, quinolinyl, indolyl, benzindolyl, acridinyl, thiazolyl, benzothiazolyl, selenazolyl, and benzoselenazolyl, each optionally substituted with 1, 2, 3, or 4 substituents independently selected from amino, C1-10 alkyl, aryl, halo, OH, wherein each of said amino, alkyl, and aryl is optionally substituted with 1, 2, 3, or 4 substituents independently selected from amino, halo, and OH.

16. The photon upconversion system of claim 1, wherein the sensitizer is selected from:

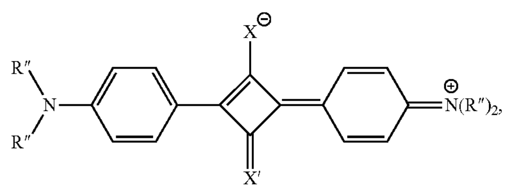

-continued

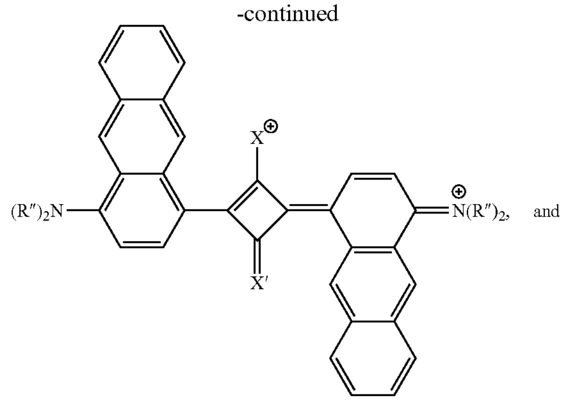

and

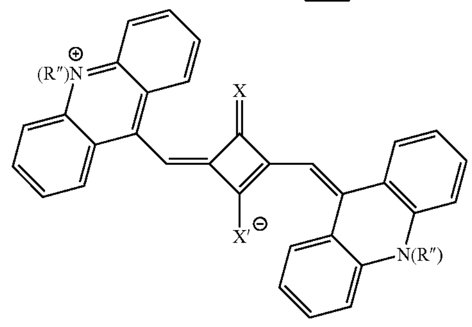

wherein R" at each occurrence is independently C1-10 alkyl; and

X and X' are each S.

17. The photon upconversion system of claim 1, wherein the emitter is selected from rubrene, TiPS-anthracene, 1-chloro-9,10-bis(phenylethynyl)anthracene, 2-chloro-9,10-bis(phenylethynyl)anthracene, and violanthrone-79.

18. A device, comprising the photon upconversion system of claim 1.

19. A sensitizer having a structure of Formula (I)

(I)

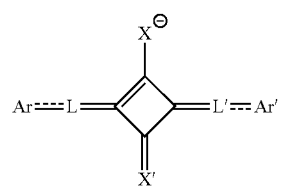

wherein:

X and X' are each independently selected from S, Se, and Te,

L is (CRR')n, wherein:

R at each occurrence is independently H, halogen, C1-10 alkyl, or C1-10 haloalkyl, R' at each occurrence is absent, or independently H, halogen, C1-10 alkyl, or C1-10 haloalkyl, and n is an integer selected from 0, 1, 2, or 3;

L' is absent, or (CR)m-(CRR')p, wherein

R at each occurrence is independently H, halogen, C1-10 alkyl, or C1-10 haloalkyl, R' at each occurrence is absent, or independently H, halogen, C1-10 alkyl, or C1-10 haloalkyl, and m is 1; and p is an integer selected from 0, 1, or 2; and Ar and Ar' are each independently selected from aryl and heteroaryl, wherein said aryl and heteroaryl are each optionally substituted with 1, 2, 3, or 4 substituents independently selected from amino, C1-10 alkyl, aryl, halo, OH, wherein each of said amino, C1-10 alkyl, and aryl is optionally substituted with 1, 2, 3, or 4 substituents independently selected from amino, halo, C1-10 alkyl, C1-6 haloalkyl, and OH; wherein one of Ar and Ar' is positively charged.

* * * * *